(12) United States Patent
Roberts et al.

(10) Patent No.: US 7,759,399 B2
(45) Date of Patent: Jul. 20, 2010

(54) PHARMACEUTICAL COMPOSITIONS

(75) Inventors: Stanley Michael Roberts, Kirsbrook (GB); Maria Gabriella Santoro, Avellino (IT); Vasudev Jadhav, Chapel-en-le-Frith (GB); Alan Michael Happe, Canterbury (GB); Paul Evans, Liverpool (GB); Nicolette Christa Ross, Chicago, IL (US); Timothy James Snape, Ormskirk (GB)

(73) Assignee: Crawford Healthcare Holdings Limited, Cheshire (GB)

( * ) Notice: Subject to any disclaimer, the term of this patent is extended or adjusted under 35 U.S.C. 154(b) by 695 days.

(21) Appl. No.: 10/957,242

(22) Filed: Sep. 27, 2004

(65) Prior Publication Data

US 2006/0252839 A1  Nov. 9, 2006

(30) Foreign Application Priority Data

Mar. 27, 2002 (GB) ................................. 0207232.0
Dec. 16, 2002 (WO) ..................... PCT/GB02/05708
Dec. 16, 2002 (WO) ..................... PCT/GB02/05709

(51) Int. Cl.
*A01N 31/00* (2006.01)
(52) U.S. Cl. ........................................ 514/712; 568/42
(58) Field of Classification Search ................. 514/712; 568/42
See application file for complete search history.

(56) References Cited

U.S. PATENT DOCUMENTS

| | | | | |
|---|---|---|---|---|
| 4,241,221 A * | 12/1980 | Grudzinskas et al. | ........ | 562/470 |
| 4,466,980 A * | 8/1984 | Tanaka et al. | ................ | 514/530 |
| 4,680,288 A * | 7/1987 | Irmscher et al. | ............... | 514/63 |
| 5,892,099 A * | 4/1999 | Maruyama et al. | .......... | 560/121 |
| 6,043,275 A * | 3/2000 | Maruyama et al. | .......... | 514/530 |
| 6,177,592 B1 * | 1/2001 | Koyama et al. | ............. | 562/503 |
| 6,262,293 B1 * | 7/2001 | Tani et al. | ..................... | 560/18 |

FOREIGN PATENT DOCUMENTS

CH          531559   *  1/1973

OTHER PUBLICATIONS

Hozien et al., Journal of Heterocyclic Chemistry, 2000, 37 (4), 943-949.*
Hall et al., Antitumor agents. 21. A proposed mechanism for inhibition of cancer growth by tenulin and helenalin and related cyclopentenones, Journal of Medicinal Chemistry (1977), 20(3), 333-337.*
Harusawa et al., [3,3]Sigmatropic ring expansion of cyclic thionocarbonates. IV. Relationship between ring size of cyclic thiocarbonates and geometry of created double bond in medium- and large-membered thiolcarbonates, Chemical and Pharmaceutical Bulletin, 1991, 39 (7), 1659-67.*

Bogaards et al., Stereoselective Conjugation of Prostaglandin A2 and Prostaglandin J2 with Glutathione, Catalyzed by the Human Glutathione S-Transferases A1-1, A2-2, M1a-1a, and P1-1, Chemical Research in Toxicology (1997), 10(3), 310-317.*
Eschler et al., A new resolution procedure for the preparation of both (R)-(+)- and (S)-(−)-4-tert-butoxycyclopent-2-enone from racemic 4-tert-butoxycyclopent-2-enone and conversion of (R)-(+)-4-tert-butoxycyclopent-2-enone into (R)-(+)-4-acetoxycyclopent-2-enone. {The Title continues below: V}.*
A new method for the determination of the enantiomeric purities of the resolved enones, Journal of Organic Chemistry (1991), 56(15), 4760-4766.*
Levin, A novel and efficient route to prostanoid intermediates, Tetrahedron Letters (1989), 30(1), 13-14.*
European Exam Report, Application No. 03720667.9, Mailed on Jan. 25, 2010.
Eschler, B. M. et al., Journal of Organic Chemistry, 56(15):4760-4766 (1991).

* cited by examiner

*Primary Examiner*—Sikarl A Witherspoon
*Assistant Examiner*—Chukwuma O Nwaonicha
(74) *Attorney, Agent, or Firm*—Mintz, Levin, Cohn, Ferris, Glovsky & Popeo, PC

(57) ABSTRACT

A compound comprising a cyclopentanone, cyclopentenone, cyclohexanone or cyclohexenone group, wherein a first ring carbon atom carries an —SR substituent, R is a substituted or unsubstituted alkyl, alkenyl, alkynyl, aryl, aralkyl, aralkenyl, or aralkynyl group that, optionally, includes at least one heteroatom in its carbon skeleton, the remaining available ring carbon atoms are optionally substituted, and said compound either: —(a) is more soluble in water at a temperature of 20-40° C.; (b) is less lipophilic; and/or, (c) has a greater therapeutic index; or; (d) is less soluble in water at a temperature of 20-40° C.; (e) is more lipophilic; and/or, (f) has a greater therapeutic index; than an equivalent cyclohex-2-en-1-one or cyclopent-2-en-1-one derivative in which a hydrogen atom replaces said —SR group.

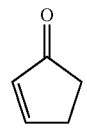

CTC-1 cLogP = −0.03

CTM-49 cLogP = 1.44

Figure 1A:
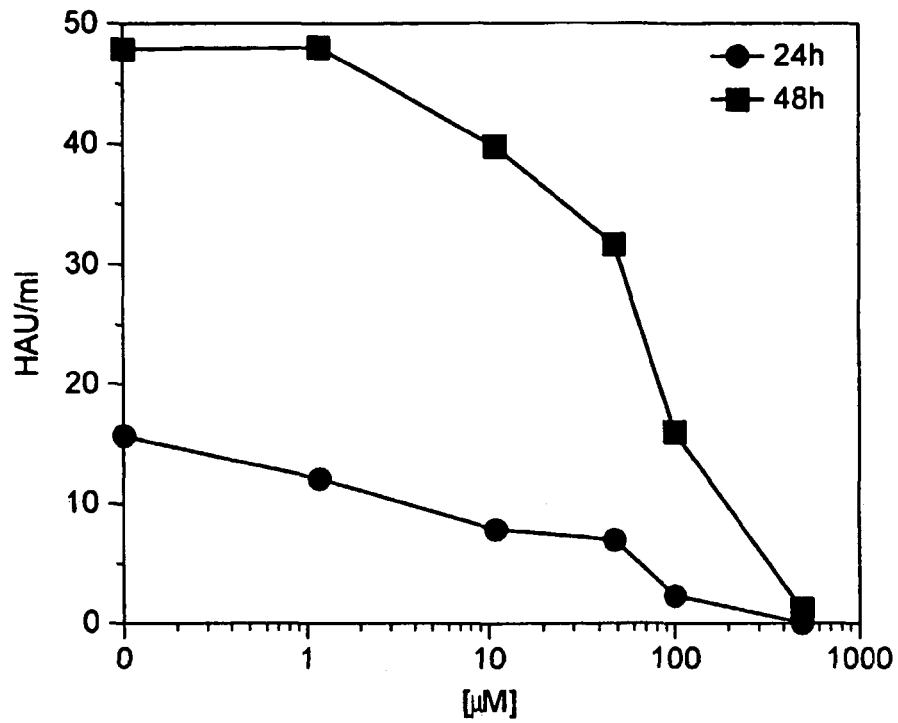
Figure 1B:
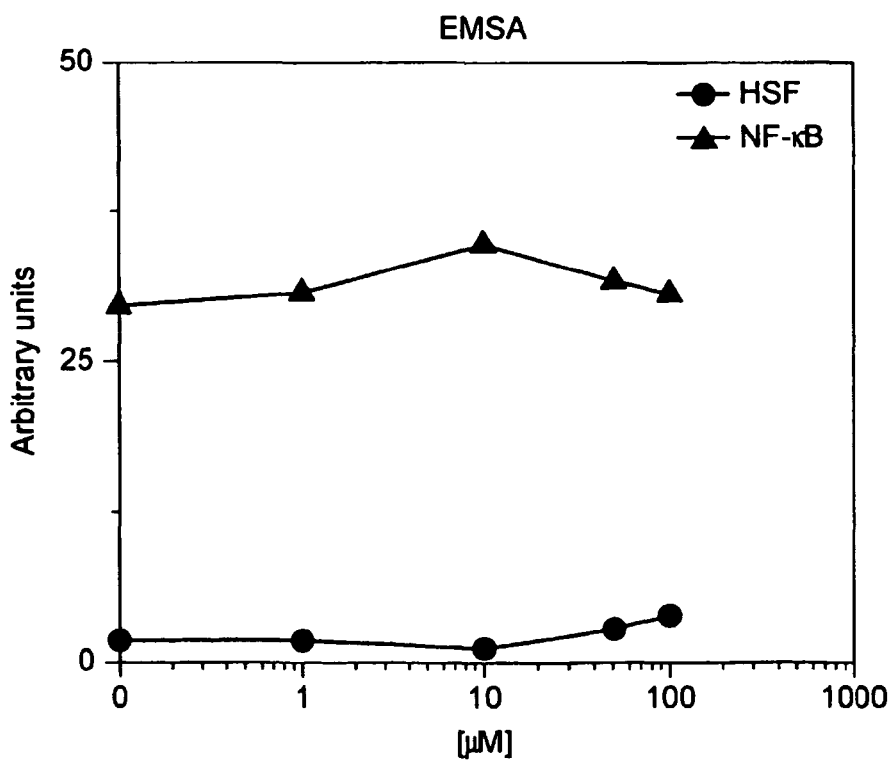
Figure 2A:
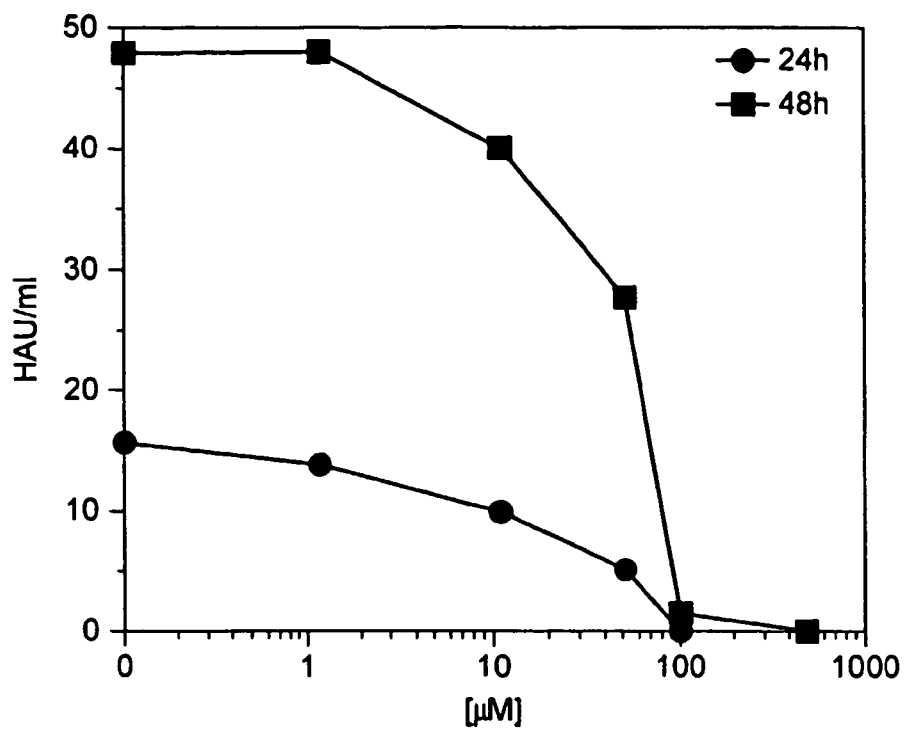
Figure 2B:
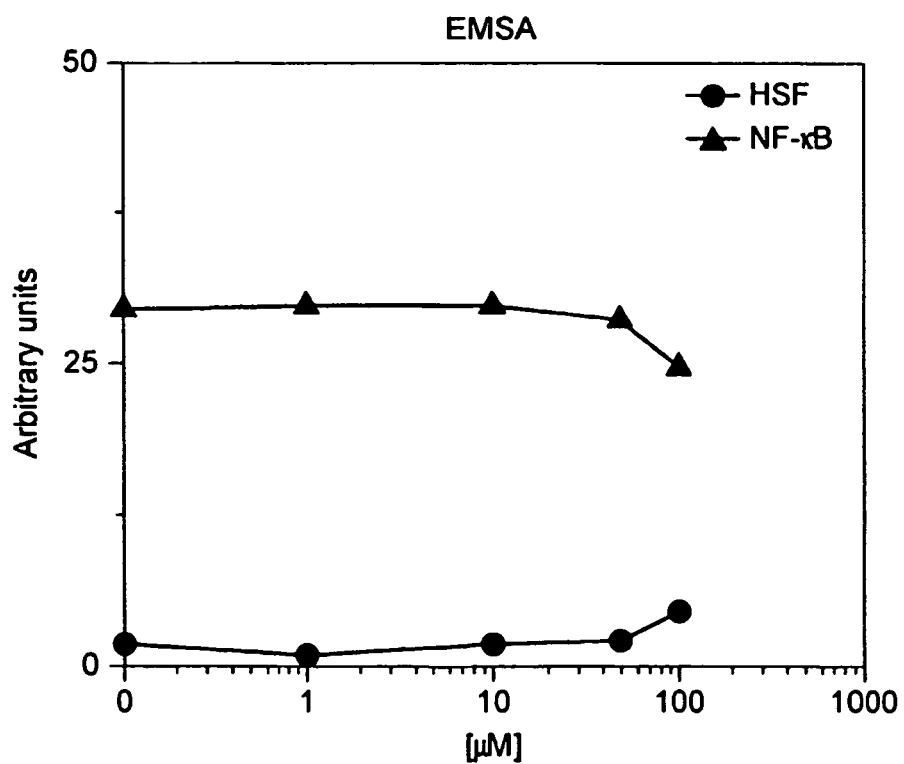
Figure 3A:
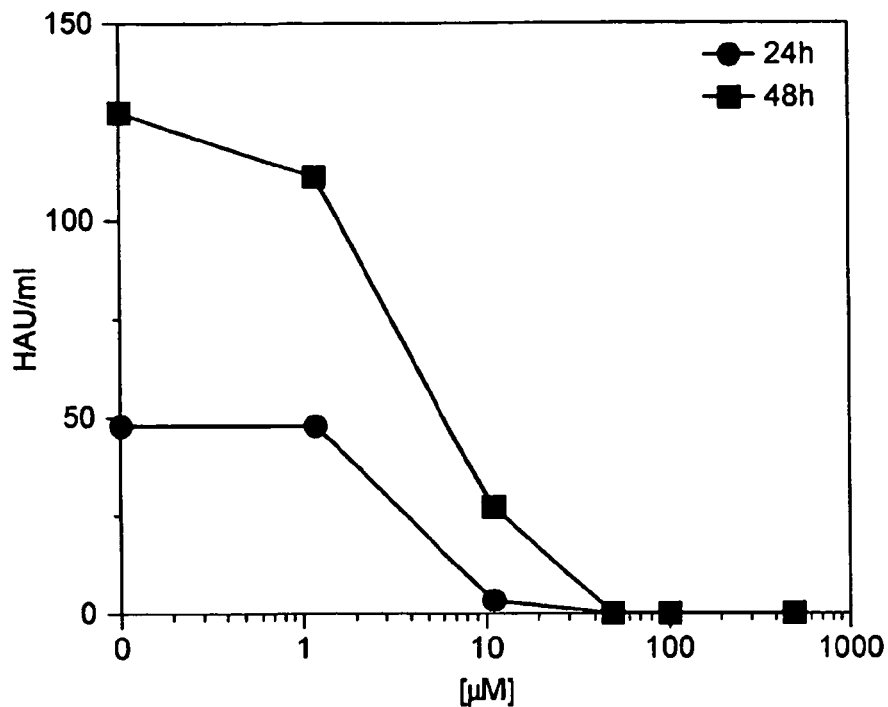
Figure 3B:
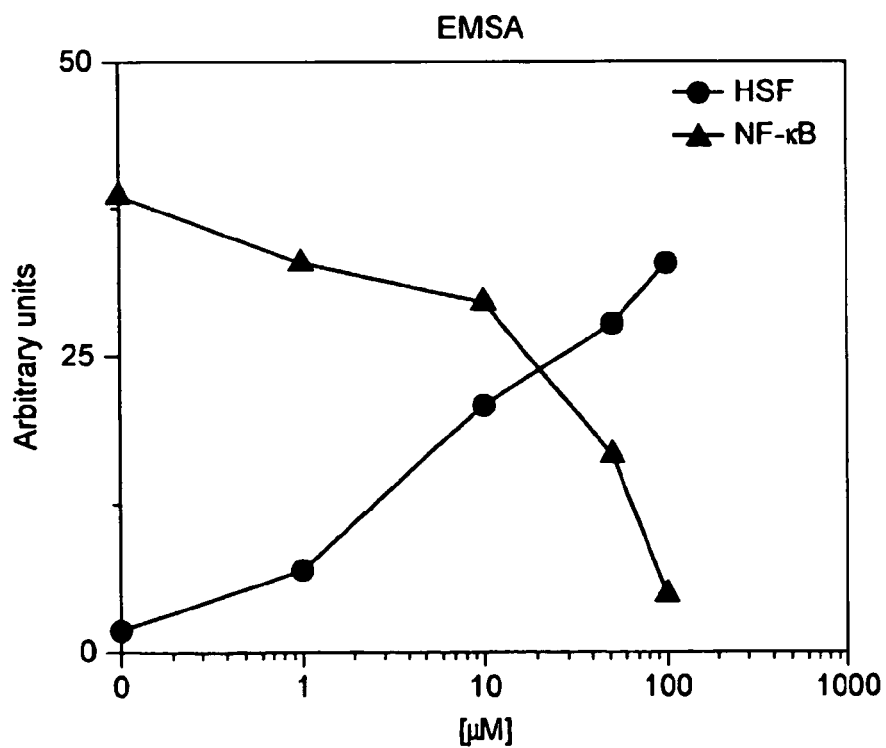
Figure 4A:
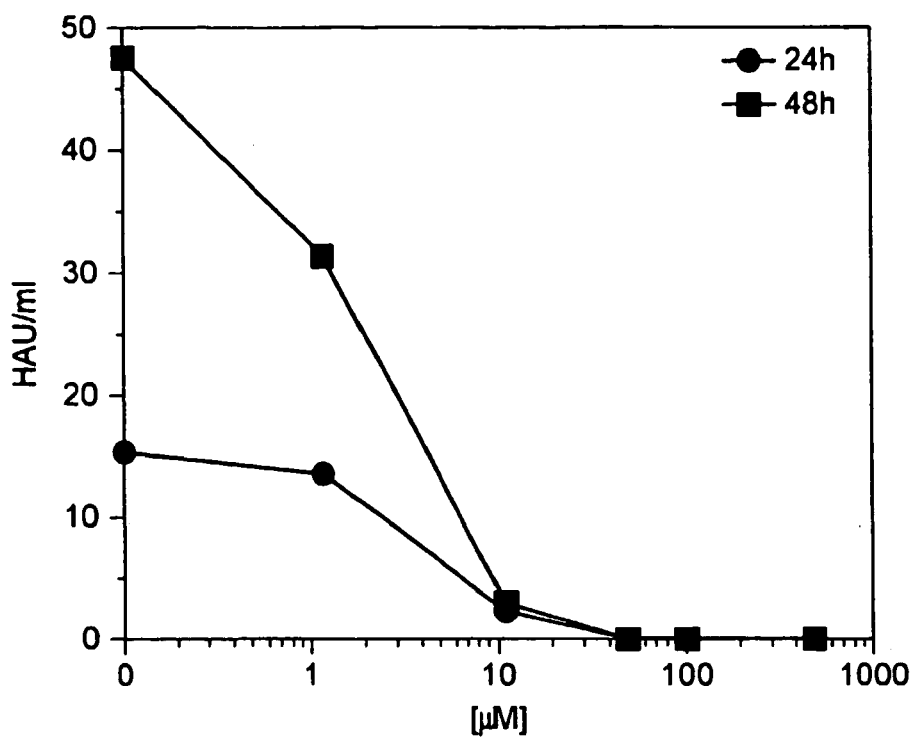
Figure 4B:
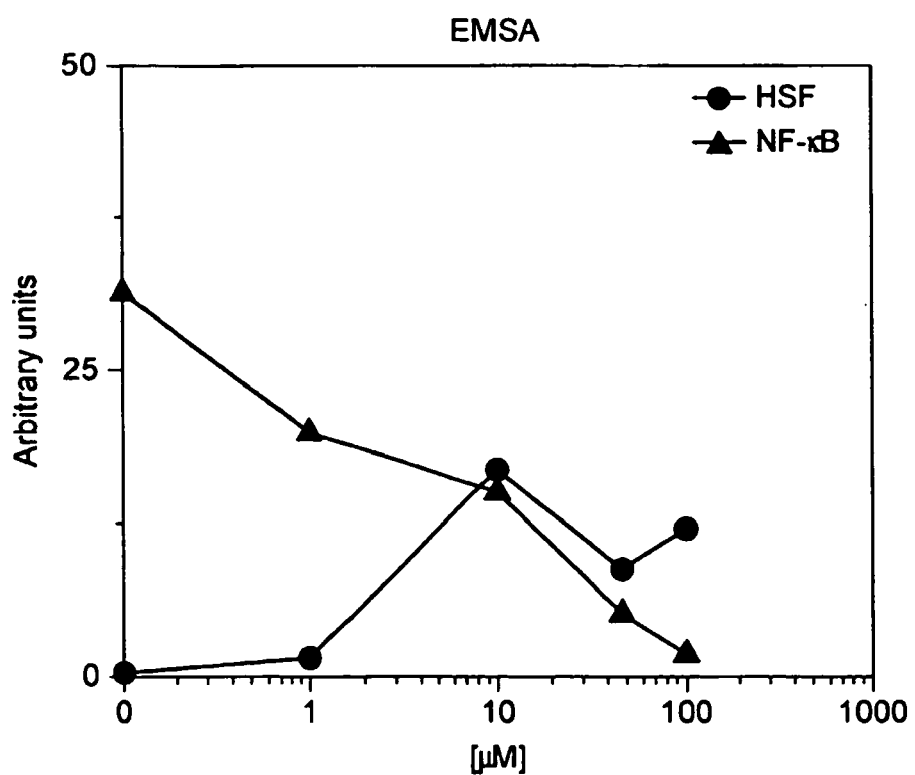
Figure 5:
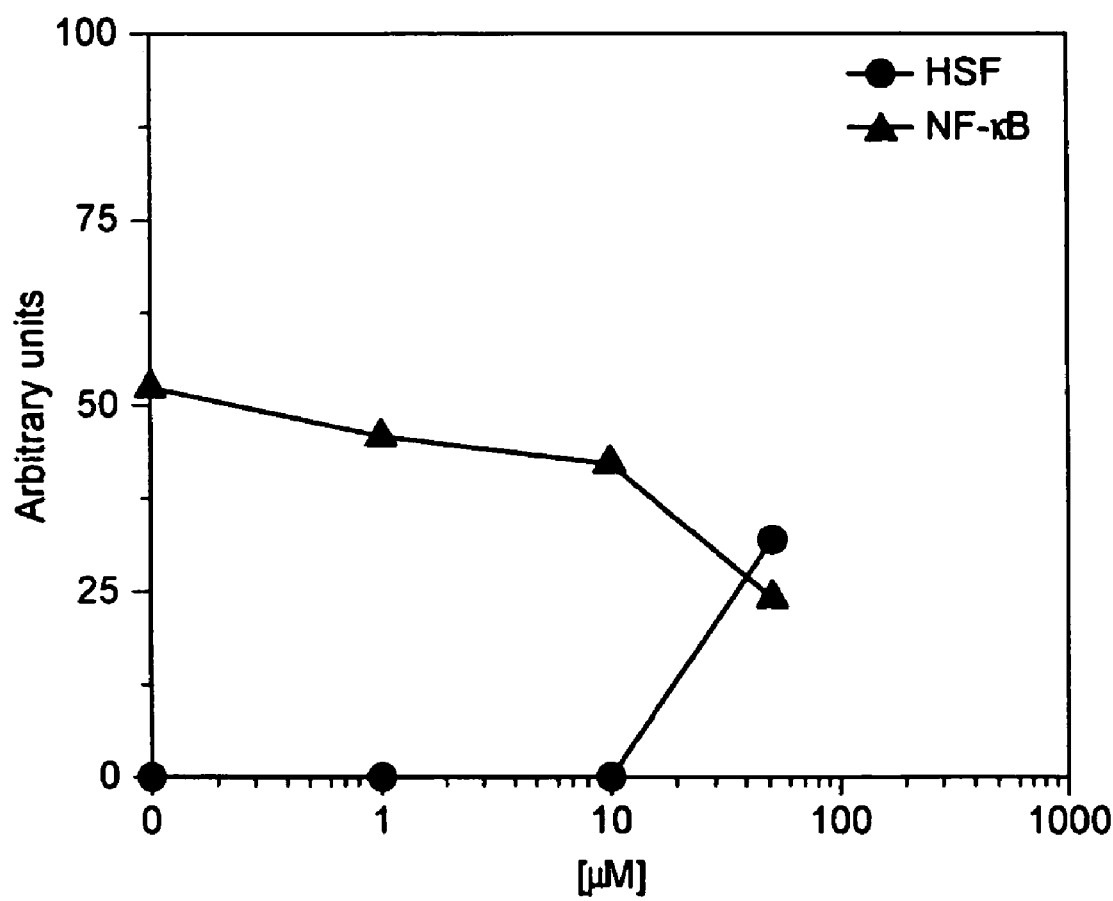
Figure 6A:
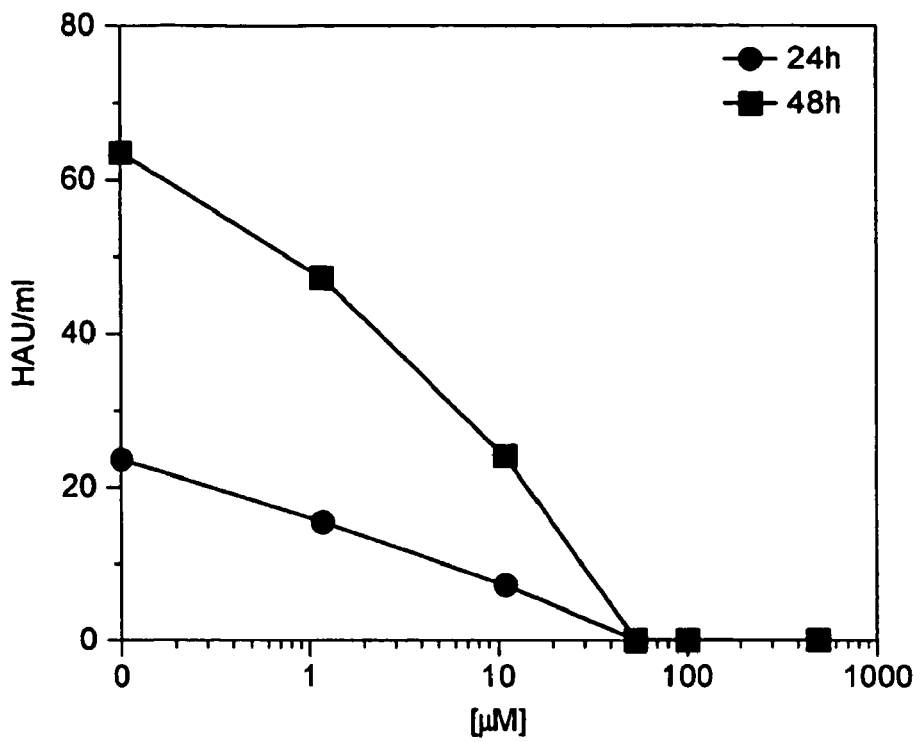
Figure 6B:
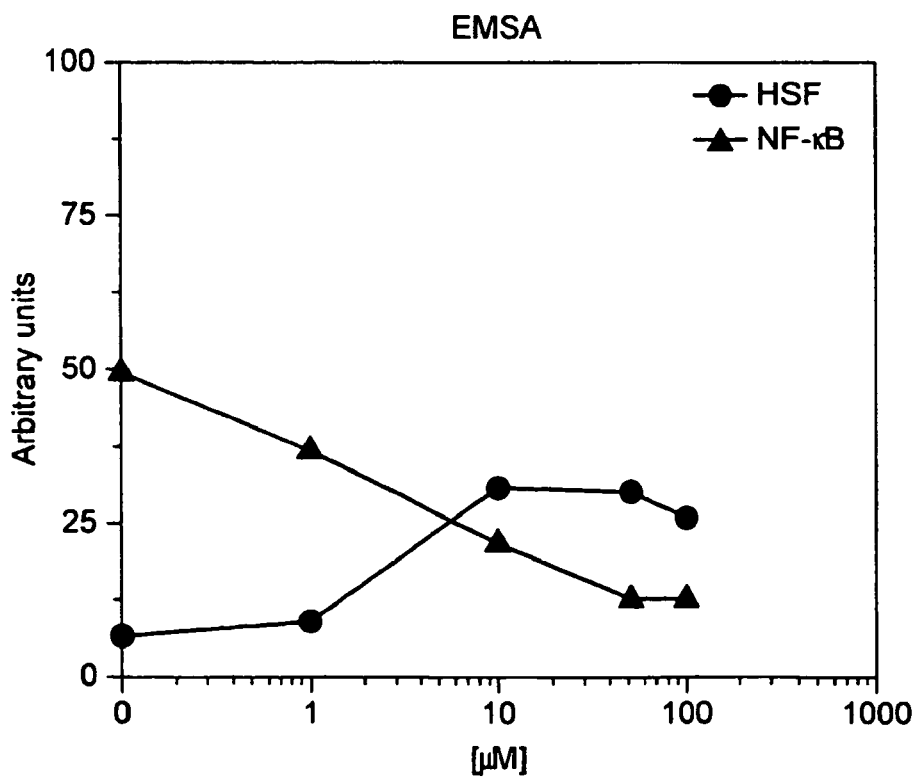

-continued
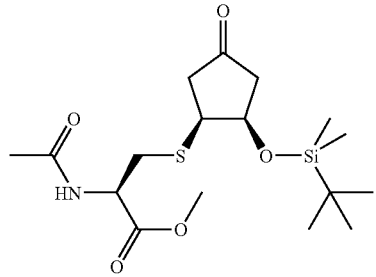
CTM-140
cLogP = 2.46
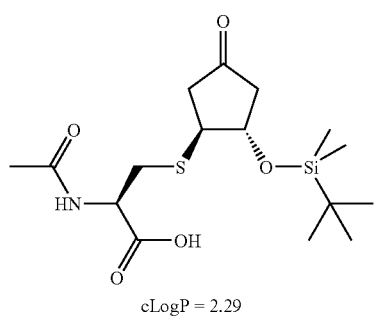
CTM-115
cLogP = 2.29
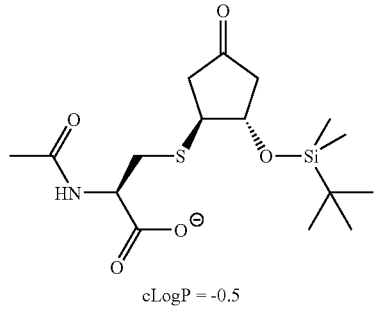
CTM-115-anion
cLogP = -0.5
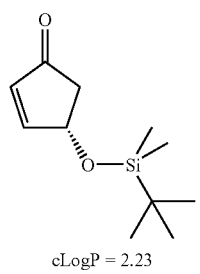
CTC-6
cLogP = 2.23
-continued
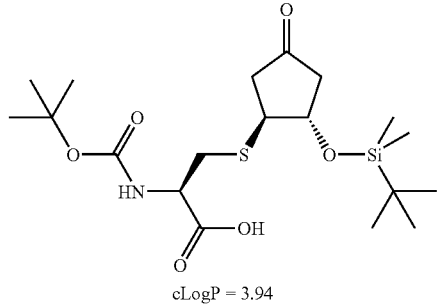
CTM-145
cLogP = 3.94
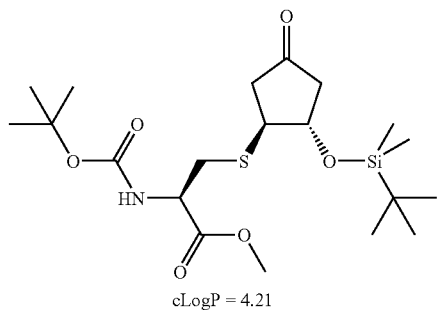
CTM-38
cLogP = 4.21
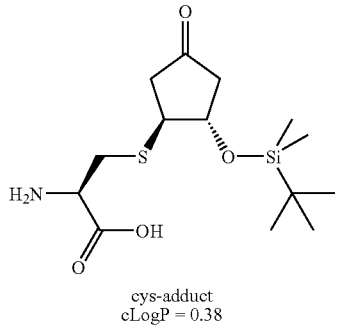
cys-adduct
cLogP = 0.38
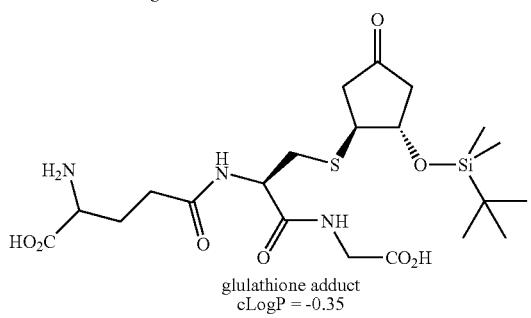
glutathione adduct
cLogP = -0.35
19 Claims, 7 Drawing Sheets

PHARMACEUTICAL COMPOSITIONS

The application is entitled to and claims priority to benefit to International Application No. PCT/GB02/005708, filed Dec. 16, 2002, and International Application No. PCT/GB02/005709, filed Dec. 16, 2002, and Great Britain Application No. GB 0207232.0, filed Mar. 27, 2002, the entire contents of each of which is incorporated herein by reference.

The present invention relates to compounds comprising a saturated or unsaturated, five or six membered carbocyclic group and in particular, to certain cyclopentanone, cyclopentenone, cyclohexanone and cyclohexenone derivatives. It also relates to the preparation of such compound and derivatives, and to their use in medicine and other fields. The invention further relates to cyclopentanone, cyclopentenone, cyclohexanone and cyclohexenone derivatives with enhanced water solubility, lipophilicity and/or therapeutic indices, and to methods of enhancing the water solubility, lipophilicity and/or therapeutic indices of pharmaceutically active cyclopentanone, cyclopentenone, cyclohexanone and cyclohexenone derivatives.

Various compounds comprising the cyclopentenone ring structure (also known as the cyclopentenone nucleus) are capable of inducing the heat shock response. The heat shock response is a finely regulated and highly conserved mechanism to protect cells against different types of injury, including extreme temperatures, oxidative stress, exposure to toxins and viral infection (1). In human cells, triggering of the heat shock response requires activation of a transregulatory protein, the heat shock transcription factor type 1 (HSF 1), which controls the expression of cytoprotective heat shock proteins (HSPs) (1). Whereas HSP induction was at first interpreted as a signal for detection of physiological stress, it is now accepted that HSPs are utilised by cells as molecular chaperones in the repair process following different types of injury to prevent damage resulting from the accumulation and aggregation of non-native proteins (1). In particular, a cytoprotective role of the heat shock protein HSP70 has now been described in a wide variety of human diseases, including ischemia, inflammation and viral infection (2-5). For these reasons HSF 1 is considered a novel, attractive target for cytoprotective and antiviral drugs. In the case of viral infection, Santoro et al. have shown that a class of prostaglandins (PGs) with potent antiviral activity function as HSP70 inducers via HSF1 activation (6,7).

The ability of prostaglandins of the A type (PGAs) to inhibit viral replication and prevent the establishment of persistent infections was first reported in 1980 (8). It is now well established that PG containing an α,β-unsaturated carbonyl group in the cyclopentane ring structure (cyclopentenone PG, cyPG) possess activity against a wide variety of DNA and RNA viruses, including herpes viruses, paramyxo viruses, orthomyxo viruses and retroviruses in in vitro and in vivo experimental models (9). The mechanism of the antiviral activity is distinct from any other known antiviral agent and is thought to involve the induction of heat shock proteins and the inhibition of the transcription factor NF-κB (nuclear factor-κB) in the infected cell.

NF-κB is an inducible eukaryotic transcription factor which has a critical role in promoting inflammation and viral replication (11). In most cells, NF-κB exists in an inactive cytoplasmic complex, whose predominant form is a heterodimer composed of p50 and p65 subunits, bound to inhibitory proteins of the IκB family, usually IκBα, and is activated in response to primary (viruses, bacteria, UV) or secondary (inflammatory cytokines) pathogenic stimuli (12). Stimulation triggers rapid phosphorylation and degradation of IκBα, resulting in NF-κB translocation to the nucleus, where the factor binds to DNA at specific κB-sites, inducing a variety of genes encoding signalling proteins. Target genes include those coding for inflammatory and chemotactic cytokines, cytokine receptors and viral proteins. NF-κB is involved in many pathological events including progression of AIDS by enhancing HIV-1 transcription and is considered an attractive therapeutic target for novel antiviral and anti-inflammatory drugs (12). Santoro et al. have shown that cyclopentenone prostaglandins inhibit NF-κB activation and NF-κB dependent HIV-1 transcription in human cells, by preventing IκBα phosphorylation and degradation, and that this effect is strictly associated with HSF1 activation (11).

Santoro et al. have identified the molecular structure of natural prostaglandins responsible for HSF activation and NF-κB inhibition (13). One component of the PGA molecule, cyclopent-2-en-1-one (also known as 2-cyclopenten-1-one), at a concentration of 125-500 µM, has been shown to be able to activate HSF1 and to rapidly and selectively trigger the synthesis of cytoprotective HSP70. At the same concentration, cyclopent-2-en-1-one has been shown to be able to block NF-κB activation by chemical or physiological inducers. These effects are associated with antiviral activity during infection with rhabdoviruses (13).

A family of pharmaceutically active cyclopent-2-en-1-one derivatives is described in International patent application no. PCT/GB00/01086, published as WO00/56341. The experimental results set out in this document show members of this family of compounds to be potent activators of HSF and inhibitors of NF-κB activity. They also show such compounds to be potent inhibitors of HSV-1 and Sendai virus replication. WO00/56341 also identifies and sets out methods whereby the described family of compounds can be prepared. Methods of preparing such compounds are also described in Example 7 set out below. The entire content of WO00/56341 is incorporated herein by reference.

The preferred members of the family of compounds described in WO00/56341 include compounds of formulae (a) and (b):—

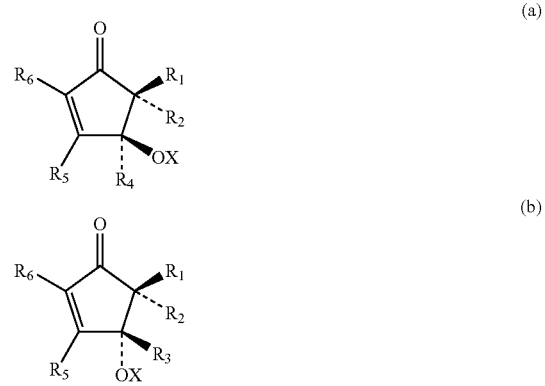

wherein:

$R_1$ and $R_2$ are, independently, hydrogen, halogen, substituted or unsubstituted alkyl, substituted or unsubstituted alkenyl, substituted or unsubstituted alkynyl, substituted or unsubstituted aminoalkyl, substituted or unsubstituted alkylthio, substituted or unsubstituted alkylsulfinyl, substituted or unsubstituted alkylsulfonyl, substituted or unsubstituted carbocyclic aryl, substituted or unsubstituted aralkyl, or substituted or unsubstituted heteroaromatic or heteroalicyclic, R$_3$ and R$_4$ are hydrogen, R$_5$ and R$_6$ are, independently, hydrogen or a halogen, and X has the formula:—

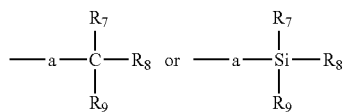

wherein R$_7$, R$_8$ and R$_9$ are, independently, hydrogen, halogen, substituted or unsubstituted alkyl, substituted or unsubstituted alkenyl, substituted or unsubstituted alkynyl, substituted or unsubstituted alkoxy, substituted or unsubstituted aminoalkyl, substituted or unsubstituted alkylthio, substituted or unsubstituted alkylsulfinyl, substituted or unsubstituted alkylsulfonyl, substituted or unsubstituted carbocyclic aryl, substituted or unsubstituted aralkyl, or substituted or unsubstituted heteroaromatic or heteroalicyclic, and "a" is absent or a linking group, optionally a hydrocarbyl linking group;

and with formulae (c) and (d):—

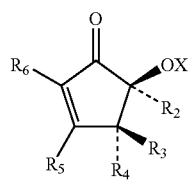

(c)

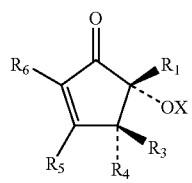

(d)

wherein:

R$_1$ and R$_2$ are hydrogen,

R$_3$ and R$_4$ are, independently, hydrogen, halogen, substituted or unsubstituted alkyl, substituted or unsubstituted alkenyl, substituted or unsubstituted alkynyl, substituted or unsubstituted aminoalkyl, substituted or unsubstituted alkylthio, substituted or unsubstituted alkylsulfinyl, substituted or unsubstituted alkylsulfonyl, substituted or unsubstituted carbocyclic aryl, substituted or unsubstituted aralkyl, or substituted or unsubstituted heteroaromatic or heteroalicyclic, and R$_5$, R$_6$ and X are as defined above.

A further family of pharmaceutically active cyclopentenone derivatives is described in International application no. PCT/GB00/04868, published as WO01/44254. Members of this family also comprise a cyclopent-2-en-1-one ring, but they include a double bond to the carbon atom in the 5 position in the ring, α to the carbonyl carbon. These compounds also have an oxygen atom directly attached to the ring via a single bond and have the formula (e):—

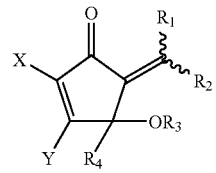

(e)

wherein:—

R$_1$ is H, or a substituted or unsubstituted alkyl or alkenyl group containing 1 to 3 carbon atoms;

R$_2$ is a substituted or unsubstituted alkyl, alkenyl, alkynyl, aryl, aralkyl aralkenyl, or aralkynyl group, optionally including at least one heteroatom in its carbon skeleton, and containing 1-12 carbon atoms;

R$_3$ is a substituted or unsubstituted alkyl, alkenyl, alkynyl, aryl, aralkyl aralkenyl, or aralkynyl group, optionally including at least one heteroatom in its carbon skeleton, and containing 1-12 carbon atoms, or a silyl group;

R$_4$ is H, or an alkyl group containing 1-3 carbon atoms;

X and Y, independently, are H, a halogen, or an alkyl group containing 1-3 carbon atoms; and R$_2$ can be cis- or trans- with respect to the carbonyl carbon in the cyclopentene ring.

Preferred members of this family of compounds are also described in WO01/44254.

The experimental results set out in WO01/44254 show members of the family of compounds described in this document to be potent activators of HSF and inhibitors of NF-κB. They also show these compounds to be potent inhibitors of HSV-1, Sendai virus and influenza virus replication. WO01/44354, furthermore, sets out methods whereby the described family of compounds can be prepared. The entire content of WO01/44354 is incorporated herein by reference.

Although many cyclopentanone, cyclopentenone, cyclohexanone and cyclohexenone derivatives are biologically and pharmaceutically active, many such compounds are also poorly soluble in water or highly lipophilic. As such, these latter compounds are less suited to being administered to patients orally than by other routes of systemic administration, that are generally less favoured by patients, such as by parenteral injection. Moreover, such compounds are often biologically active in a manner that suggest usefulness in the topical treatment of skin conditions such as, for example, psoriasis and skin cancers. However, many are insufficiently lipophilic to penetrate the skin to the degree required to be therapeutic effective in such treatments.

The therapeutic index of a drug or pharmaceutically active compound is indicated by the ratio of its median lethal dose, or $LD_{50}$, to its medium effective dose, or $ED_{50}$. Because its use would generally involve a lower risk of causing toxic side effects in individual patients given a therapeutically effective dose, a compound with a larger therapeutic index would normally be preferred over an alternative with a smaller therapeutic index. Accordingly, if the therapeutic index of a particular pharmaceutically active compound could be increased without ill effect, this would be an attractive result.

According to a first aspect of the present invention, there is provided a compound comprising a cyclopentanone, cyclopentenone, cyclohexanone or cyclohexenone group, wherein a first ring carbon atom carries an —SR substituent, R is a substituted or unsubstituted alkyl, alkenyl, alkynyl, aryl, aralkyl, aralkenyl, or aralkynyl group that, optionally, includes at least one heteroatom in its carbon skeleton, the remaining available ring carbon atoms are optionally substituted, and said compound either:—

(a) is more soluble in water at a temperature of 20-40° C.;
(b) is less lipophilic; and/or,
(c) has a greater therapeutic index; or;
(d) is less soluble in water at a temperature of 20-40° C.;
(e) is more lipophilic; and/or,
(f) has a greater therapeutic index;

than an equivalent cyclohex-2-en-1-one or cyclopent-2-en-1-one derivative in which a hydrogen atom replaces said —SR group.

For compounds in accordance with the invention in which the —SR group is bound to a cyclopentanone or cyclopentenone group, the "equivalent cyclopent-2-en-1-one or cyclohex-2-en-1-one derivative in which a hydrogen atom replaces said —SR group" is a cyclopent-2-en-1-one derivative with, excepting the absent —SR group, the same substitution pattern as the inventive compound. For compounds in accordance with the invention in which the —SR group is bound to a cyclohexanone or cyclohexenone group, the "equivalent cyclopent-2-en-1-one or cyclohex-2-en-1-one derivative in which a hydrogen atom replaces said —SR group" is a cyclohex-2-en-1-one derivative with, excepting the absent —SR group, the same substitution pattern as the inventive compound. Hereinafter, the "equivalent cyclopent-2-en-1-one or cyclohex-2-en-1-one derivative in which a hydrogen atom replaces said —SR group" will be referred to merely as the "equivalent cyclopent-2-en-1-one or cyclohex-2-en-1-one derivative", the "equivalent compound", or similar.

Where a compound in accordance with the invention is required to be less lipophilic than an "equivalent cyclopent-2-en-1-one or cyclohex-2-en-1-one derivative", this means that the ratio of n-octanol to aqueous solubility (i.e. the n-octanol/water partition coefficient) for the inventive compound is lower than it is for the "equivalent" compound. Similarly, where a compound in accordance with the invention is required to be more lipophilic than an "equivalent cyclopent-2-en-1-one or cyclohex-2-en-1-one derivative", this means that the ratio of n-octanol to aqueous solubility for the inventive compound is higher than it is for the "equivalent" compound. The ratio of n-octanol to aqueous solubility is usually expressed in terms of its base ten logarithm, "logP", and a compound with a logP value of 1 will be 10 times more soluble in n-octanol than it is in water, a compound with a logP value of 2 will be 100 times more soluble in n-octanol than it is in water and so on. LogP values can be measured by experiment, or calculated using one of several available computer programs or algorithms. Examples of these include the Pomona College Medicinal Chemistry program, the MacLogP application from BioByte Corp. (Claremont USA), and the method described by Moriguchi et al.(20). Thus, it is preferred that compounds, required in this specification to be less lipophilic than equivalent cyclopent-2-en-1-one or cyclohex-2-en-1-one derivatives, will have lower logP values than such equivalents, and that compounds required in this specification to be more lipophilic than equivalent cyclopent-2-en-1-one or cyclohex-2-en-1-one derivatives will have higher logP values than such equivalents. In this context, the logP values are preferably calculated values ("clogP" values) derived from applying one of the aforementioned programs or algorithms.

For each equivalent cyclopent-2-en-1-one or cyclohex-2-en-1-one derivative, there are many compounds in accordance with the first aspect of the present invention that differ from each other solely by the nature of their —SR substituents. The useful biological and pharmacological properties of equivalent cyclopent-2-en-1-one or cyclohex-2-en-1-one derivatives are often retained and sometimes even enhanced in the related —SR substituted compounds in accordance with the first aspect of the invention. It has also been found that the lipophilicity and water solubility of compounds in accordance with the first aspect of the invention is highly dependent upon the nature of the —SR group which they carry. In essence, increasing the lipophilicity of the group R (in the —SR substituent) will result in a compound in accordance with the invention that is more lipophilic and less water soluble, and vice versa, and the degree to which an equivalent compound's lipophilicity or water solubility can be manipulated in this way is sufficient for many such compounds to be "adaptable" for both topical and oral use. Thus, compounds in accordance with the first aspect of the invention provide those skilled in the art with the means to adapt the physical properties of any given equivalent compound to suit a particular mode of delivery, e.g. oral or topical, without prejudicing its pharmacological properties. This represents a highly significant and surprising advantage of the present invention.

Where a compound in accordance with the invention is required to have a greater therapeutic index than an "equivalent", this relationship must hold true for at least one therapeutic application. For the purposes of this specification, the existence of such a relationship can be established either by observation of in vivo effects, or via in vitro tests or assays of the type conventionally employed by persons skilled in the art for the purpose of predicting the therapeutic indices of putative drug substances. For example, an assay for one of the properties discussed below could be used in combination with a toxicity assay, to provide the required information for a particular pair of inventive compound and equivalent cyclopent-2-en-1-one or cyclohex-2-en-1-one. Examples of appropriate assays are set out in Examples 9-17 below.

In a second aspect, the present invention provides a compound comprising a saturated or unsaturated five or six membered carbocyclic group, wherein at least one ring carbon atom forms a carbonyl group with an associated oxygen atom, a second ring carbon atom carries an —SR substituent, R is a substituted or unsubstituted alkyl, alkenyl, alkynyl, aryl, aralkyl, aralkenyl, or aralkynyl group that, optionally, includes at least one heteroatom in its carbon skeleton, and said compound is not a compound of formula I:—

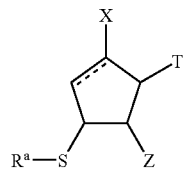

I in which $R^a$ is any group that can form a compound HS—$R^a$, ----- is an optional bond, X is OH, Y is O and Z is H when said bond is present, X is O, Y is OH and Z is OH when said bond is absent, and when X or Y is O, it is bound to the ring by a double bond.

Compounds of formula I, as defined above, are disclosed in EP 0,984,001 A1 and are excluded from this aspect of the invention. None of the compounds disclosed in EP 0,984,001 A1 lie within the scope of the present invention.

Preferably, said carbocyclic group is an alicylic group and, more preferably, said compound is a substituted or unsubstituted cyclopentanone, cyclopentenone, cyclohexanone or cyclohexenone. It is further preferred for compounds in accordance with the second aspect of the invention to be compounds in accordance with the first aspect of the invention.

The preferred compounds in accordance with the invention are pharmaceutically and, preferably, therapeutically active. It is also preferred for compounds in accordance with the invention to have a calculated or measured logP value that is at least 0.25, 0.5, 0.75, 1 or 1.25 higher or lower than the logP value for the equivalent cyclohex-2-en-1-one or cyclopent-2-en-1-one derivatives, wherein the logP values for the compound and derivative are calculated or measured using the same technique. In embodiments, compounds in accordance with the invention have a logP value of 5 or less, and preferably of no more than 4.15, 4, 3, 2, or 1 when calculated by the method described by Moriguchi et al. (20). Compounds with logP values in these latter preferred ranges are generally more readily absorbed from the gastro-intestinal tract and, therefore, are more suited to oral administration. See Lipinski et al. (21). In alternative embodiments, compounds in accordance with the invention have a logP value of at least 3.5, 4.2, or 5 and preferably of up to 6 or 7 and, therefore, are suitable for use in topical formulations for application to the skin.

Preferably, compounds in accordance with the invention are cyclopent-2-en-1-one or cyclohex-2-en-1-one derivatives. Further preferred compounds in accordance with the invention include substituted and unsubstituted 3-(RS)-cyclopentan-1-ones, 3-(RS)-cyclohexan-1-ones, 4-(RS)-cyclopentan-1-ones, 4-(RS)-cyclopent-2-en-1-ones, 4-(RS)-cyclohex-2-en-1-ones and 3-(RS)-cyclopent-2-en-1-ones (wherein "RS" is the group RS—). It is further preferred that the cyclopentanone, cyclopentenone, cyclohexanone or cyclohexenone group is a substituted or unsubstituted cyclopentanone or cyclohexanone group, and the most preferred compounds in accordance with the invention are substituted or unsubstituted cyclopentanones.

As noted, compounds in accordance with the invention optionally include further substituents, in addition to the carbonyl oxygen and —SR group. These can be bound to any one or more of the ring carbon atoms excepting that bound to the carbonyl oxygen. Preferred examples of such substituents are described in the following sections of this specification.

The group —SR is preferably in the 3 position of the cyclopentanone, cyclopentenone, cyclohexanone or cyclohexenone ring of compounds in accordance with the present invention. It is also preferred for the carbon atoms in the 4, 5 and/or 6 (where present) positions of the cyclopentanone, cyclopentenone, cyclohexanone or cyclohexenone ring of compounds in accordance with the invention to carry substituents other than a hydrogen atom. It is particularly preferred that the carbon atom in the 3 position in the cyclopentanone or cyclohexanone ring, of those inventive compounds that include these latter saturated structures, carries an —SR group.

Compounds in accordance with the invention can include a plurality of —SR groups. Certain examples of such compounds include a second —SR group bound to a substituent, itself bound to the carbocyclic group or the cyclopentanone, cyclopentenone, cyclohexanone or cyclohexenone ring. Thus, in preferred embodiments, compounds in accordance with the invention can comprise an additional group —SR bound to the first carbon atom in a side chain carried by the ring carbon atom adjacent (α) to the carbonyl ring carbon atom.

R can be an $R^xCH_2$— group, such that the group —SR is an —$SCH_2R^x$ group, wherein $R^x$ is hydrogen or a substituted or unsubstituted alkyl, alkenyl, alkynyl, aryl, aralkyl aralkenyl, or aralkynyl group, that optionally includes at least one heteroatom in its carbon skeleton. R, preferably, contains 1-12 carbon atoms.

In those compounds in accordance with the invention which are more water soluble and/or less lipophilic than the equivalent cyclopent-2-en-1-one or cyclohex-2-en-1-one derivative, the group R or $R^x$, preferably, includes at least one hydrophilic group. Said hydrophilic group can be or include a hydroxyl, carbonyl, carboxyl, amino, amido, quaternary ammonium or thiolyl group. In such compounds, therefore, R or $R^x$ can provide the functionality of an amine, amide, peptide, ester, carboxylic acid, carboxylic acid salt, alcohol, aldehyde, ketone or thiol to an inventive compound. In preferred such compounds the group —SR is an S-cysteinyl or a hydrophilic substituted S-cysteinyl group. Preferred substituted S-cysteinyl groups include di- and tri-peptide groups that include an S-cysteinyl moiety, such as an S-glutathionyl group.

In those compounds in accordance with the invention which are less water soluble and/or more lipophilic than the equivalent cyclopent-2-en-1-one or cyclohex-2-en-1-one derivative, the group R or $R^x$, preferably, includes at least one lipophilic group and/or is lipophilic. Such lipophilic groups include substituted and unsubstituted alkyl, alkenyl, alkynyl, aryl, aralkyl, aralkenyl, or aralkynyl groups that, optionally, include at least one heteroatom in their carbon skeletons, but which do not carry any substituents that render them hydrophilic. Preferred such groups include substituted and unsubstituted phenyl and napthyl groups and N-tert-butoxycarbonyl S-cysteinyl ester (e.g. methyl and ethyl) groups.

Cyclopentan-1-one derivatives of the following formula also represent a preferred group of compounds in accordance with the invention:—

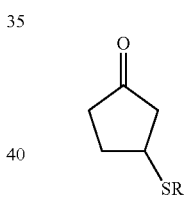

wherein R is as previously defined.

A preferred compound in this last mentioned group is that of formula CTM-49:—

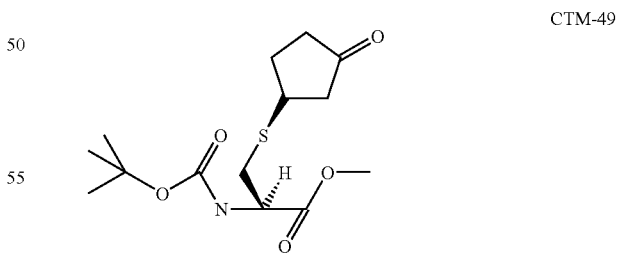

CTM-49

As has been noted, an advantage of certain compounds in accordance with the above described aspects of the invention is that, because they are less lipophilic and/or more soluble in water at around room temperature and/or body temperature than are analogous compounds that do not include an —SR substituent, they are more suited to use in orally administered pharmaceutical compositions. Thus, in a further aspect, the present invention provides pharmaceutical compositions for oral administration, comprising a compound in accordance with the invention that is more soluble in water at a temperature of 20-40° C. and/or less lipophilic than an equivalent cyclohex-2-en-1-one or cyclopent-2-en-1-one derivative in which a hydrogen atom replaces said —SR group. Such compositions can include one or more pharmaceutically acceptable diluent, carrier and/or other excipient suitable for use in compositions for oral administration.

As has also been noted, an advantage of certain other compounds in accordance with the above described aspects of the invention is that, because they are more lipophilic and/or less soluble in water at around room temperature and/or body temperature than are analogous compounds that do not include an —SR substituent, they are more suited to use in pharmaceutical compositions for topical administration, particularly to the skin. Thus, in a yet further aspect, the present invention provides pharmaceutical compositions for topical administration, preferably to the skin, comprising a compound in accordance with the invention that is less soluble in water at a temperature of 20-40° C. and/or more lipophilic than an equivalent cyclohex-2-en-1-one or cyclopent-2-en-1-one derivative in which a hydrogen atom replaces said —SR group. Such compositions can include one or more pharmaceutically acceptable diluent, carrier and/or other excipient suitable for use in compositions for topical administration.

Moreover, because the pharmaceutically active compounds in accordance with any of the above described aspects of the invention can also have a greater therapeutic index than their equivalents without an —SR substituent, they are potentially more useful in a therapeutic context.

In the pharmaceutical industry, a major problem with any potential drug is that it may be very biologically active but somewhat toxic. For example, an anti-tumour drug must be toxic towards certain groups of cells but not potentially harmful to other cells.

Cyclopentenone compounds are known to undergo Michael reactions with glutathione in the cell. Glutathione is found throughout the body and plays crucial roles in protecting cells from oxidative damage (maintaining redox balance). In this regard, work by Uchida et al. (22) and others has suggested a role for glutathione in protecting cells from oxidative stress as a radical scavenger. Uchida's work showed that cells with depleted glutathione retain higher concentration of radical oxygen species. It also demonstrated that, when such cells were treated with N-acetyl-cysteine and cell viability was measured, an increase in cell life and a decrease in the production of radical oxygen species was observed. Uchida et al. came to the conclusion that species capable of reducing glutathione levels in the cell, also reduce the cell's anti-oxidant defences and increase the induction of radical oxygen species. They also showed that cyclopentenone mediated production of radical oxygen species was well correlated with cytotoxicity and, thus, demonstrated a potentially important mode of cytotoxicty or induction of cell death by cyclopentenone compounds.

Glutathione is also known to protect cells from dangerous electrophilic species. For example, morphine type compounds undergo a Michael reaction with glutathione that results in complete deactivation of the drug (23). If large amounts of paracetamol (acetaminophen) are taken then glutathione in the liver is depleted [in 1999 there were 150 deaths in the UK from paracetamol poisoning]. If N-acetyl cysteine is taken intravenously or orally less than 15 h after the overdose it effectively removes the offending electrophilic paracetamol metabolite (24).

Other studies have shown that a reduction of intracellular thiol content can increase the sensitivity of tumour cells to radiation treatment. Moreover, cells exhibiting depleted levels of glutathione have been shown to be more susceptible to radiation, chemotherapeutic agents and oxygen radical species that otherwise would have been destroyed via radical reaction with glutathione (25).

A glutathione group cannot be added to a saturated moiety, such as a cyclopentanone or cyclohexanone group, via a Michael reaction. Thus, unless they are metabolised into the equivalent unsaturated cyclopent-2-en-1-one or cyclohex-2-en-1-one derivatives, compounds in accordance with the invention that comprise a cyclopentanone or cyclohexanone group are less likely to react with glutathinone in vivo than are these unsaturated equivalents. Such saturated compounds, therefore, are less likely to deplete the levels of glutathione in a patient's cells, and thereby compromise their anti-oxidant defences, than the equivalent cyclopent-2-en-1-one or cyclohex-2-en-1-one derivatives. Without wishing to be bound by theory, this may explain why some compounds in accordance with the invention have significantly enhanced therapeutic indices, in addition to enhanced or reduced water solubility and reduced or enhanced lipophilicity.

Without again wishing to be bound by theory, it is considered that certain compounds in accordance with the present invention, wherein the carbon atom in the 3 position in their cyclopentanone or cyclohexanone rings carries an —SR group, enjoy their enhanced properties partially because they can act as pro-drugs for the equivalent cyclopent-2-en-1-ones and cyclohex-2-en-1-ones, in the sense that it is thought that they are converted into the latter in vivo. In this regard, it is considered that, before it is cleaved, the group —SR renders the compound in accordance with the invention more suited to a chosen mode of administration (e.g. oral or topical to the skin) and that in vivo cleavage of the —SR group releases, via a reverse Michael reaction, the more potent cyclopent-2-en-1-one or cyclohex-2-en-1-one equivalent.

Thus, in embodiments, compounds in accordance with the invention are transformable into an equivalent cyclohex-2-en-1-one or cyclopent-2-en-1-one derivative, in which a hydrogen atom replaces said —S—R group, by a reverse Michael reaction, or are pro-drugs for such an equivalent.

In further preferred embodiments, the group —SR is an S-cysteinyl or a substituted S-cysteinyl group. In the context of this application, a substituted or unsubstituted S-cysteinyl group comprises a cysteinyl moiety that is bound to the ring via its sulphur atom, with the ring replacing the hydrogen atom that is bound to the equivalent sulphur atom in cysteine. Preferred substituted S-cysteinyl groups include di- and tri-peptide groups that include an S-cysteinyl moiety, such as S-glutathionyl, S-cysteinyl ester and other like groups, including N-tert-butoxycarbonyl S-cysteinyl and N-tert-butoxycarbonyl S-cysteinyl ester (e.g. methyl and ethyl) groups.

Without once again wishing to be bound by theory, it is considered that compounds in accordance with these latter embodiments of the invention are also capable of providing a secondary therapeutic effect resulting from their incorporation of a substituted or unsubstituted cysteinyl moiety. For example, when acting as pro-drugs in the aforementioned manner, such compounds may be capable of delivering both the equivalent cyclopent-2-en-1-one or cyclohex-2-en-1-one derivative and the reduced form of the substituted or unsubstituted cysteinyl moiety to target cells in a patient's body, where both may exert their therapeutic effects. The therapeutic effect exerted by the reduced form of the substituted or unsubstituted cysteinyl moiety can be the prevention of glutathione depletion, especially when the reduced moiety is glutathione, an analogue or precursor. For example, the reduced, substituted or unsubstituted cysteinyl moiety may compete with native glutathione, to reduce the amount of the latter that is bound by the cyclopent-2-en-1-one or cyclohex-2-en-1-one derivative (formed after in vivo cleavage) or a metabolite, or it may replace or lead to the replacement of glutathione bound by the derivative or a metabolite. Such activity is thought to contribute significantly to the reducing the toxicity of the inventive compounds and, hence, to the increased therapeutic indices enjoyed by these compounds, in comparison to the equivalent cyclopent-2-en-1-one or cyclohex-2-en-1-one derivatives.

Compounds in accordance with the invention preferably are capable of one or more of the following:
a) activating HSF
b) inhibiting NF-κB
c) inhibiting the replication of HSV-1
d) inhibiting the replication of Sendai virus.

A skilled person can readily assay for the above activities and examples of suitable assays are set out in Examples 9-13 below.

Compounds that have greater activity in at least one of the foregoing respects than cyclopent-2-en-1-one (at least at certain concentrations) represent preferred embodiments of the invention; those that enjoy such activity at a concentration within the range of 1-200 μM, or over the whole or a part of said range, being particularly preferred. Preferably, compounds in accordance with the invention have a level of activity in at least one of the foregoing respects that is at least twice the level of cyclopent-2-en-1-one. More preferably, it is at least 10 times that of cyclopent-2-en-1-one.

Activity in one of the above respects is indicative of a compound's capacity to be pharmaceutically active. Accordingly, in a yet further aspect, the present invention provides a compound in accordance with the first and/or second aspect of the invention for use in medicine (including veterinary medicine). Preferred such uses include the treatment of the human or animal body by therapy and diagnostic methods practised upon the human or animal body. The treatment may be prophylactic or may be in respect of an existing condition. Therapeutic (including prophylactic) and diagnostic methods, involving the use of a compound in accordance with the first and/or second aspect of the invention, are also within the remit of the invention.

The use of such compounds for the manufacture of medicament for use in therapeutic or diagnostic methods to be practised on the human or animal body, lies within the scope of a further aspect of the invention.

The preferred uses for compounds in accordance with the first and/or second aspect of the invention include the treatment of disorders which can be treated in a host by the activation of a heat shock transcription factor (e.g. HSF1), by the induction of heat shock proteins (e.g. hsp70) and/or by the inhibition of NF-κB. Certain preferred compounds in accordance with the first and/or second aspect of the invention can be used in therapeutic applications that involve activating HSF and inhibiting the activity of NF-κB.

Thus, in accordance with the invention, compounds in accordance with the invention can be used to treat diseases or conditions in which such activity is indicated or can be of advantage. They can also be used in the manufacture of medicaments for use in such treatments. The preferred therapeutic and diagnostic applications for the inventive compounds are discussed in detail in the section headed "Medical uses for compounds in accordance with the invention" below.

In a further aspect of the present invention, there is provided a method of changing the lipophilicity, water solubility and or therapeutic index of a pharmaceutically active second compound comprising a saturated or unsaturated five or six membered carbocyclic group, wherein at least one ring carbon atom forms a carbonyl group with an associated oxygen atom, said method comprising forming an adduct of said second compound and a thiol of the formula HSR, wherein R is as herein before defined. In an embodiment, this method involves decreasing the lipophilicity and/or increasing the water solubility and/or the therapeutic index of the pharmaceutically active second compound, and in an alterative embodiment the method involves decreasing the water solubility and/or increasing the lipophilicity and/or the therapeutic index of the pharmaceutically active second compound.

Preferably, the resulting adduct is also a pharmaceutically active compound comprising a saturated or unsaturated five or six membered carbocyclic group, wherein at least one ring carbon atom forms a carbonyl group with an associated oxygen atom and a second ring carbon atom carries an —SR substituent. The adduct may act as a pro-drug in the manner discussed above, or it may be pharmaceutically active in its own right. In preferred embodiments, the adduct is a compound comprising a saturated or unsaturated five or six membered carbocyclic group in accordance with the second aspect of the invention. More preferably, the adduct is a compound in accordance with the first aspect of the invention.

In further preferred embodiments of the inventive method, the pharmaceutically active second compound comprises an unsaturated five or six membered carbocyclic group, the adduct comprises a saturated or unsaturated, preferably saturated, five or six membered carbocyclic group, the number of carbon atoms in said five or six membered carbocyclic group is the same in the adduct and second compound, the five or six membered carbocyclic group in the adduct has one fewer double bonds than its counterpart in the second compound, and an —SR substituent is bound to a ring carbon atom in the adduct, the equivalent to which in the second compound is preferably unsubstituted.

In preferred embodiments of the inventive method, the adduct is formed via a Michael reaction between the unsaturated second compound and the thiol. Preferred methods of forming the adduct are described in the examples that follow.

A further —SR group can, optionally, be added into a side chain bound to the five or six membered carbocyclic group.

In a further aspect, the present invention provides an adduct as herein before defined, prepared or preparable by a method in accordance with the invention.

For the avoidance of doubt, it is confirmed that the term "alkenyl" denotes a group with one or more double bonds in its carbon skeleton and the term "alkynyl" denotes a group with one or more triple bonds in its carbon skeleton. It should also be understood that, for the purposes of this specification, alkynyl groups may include both double and single bonds in their carbon skeletons. Unless otherwise specified, groups referred to in this specification as alkyl, alkenyl or alkynyl groups can be straight chained or branched, or be or include cyclic groups. However, unless the contrary is indicated, they are preferably straight chained or branched.

Unless otherwise indicated and with the exception of the groups R, $R^a$ and $R^x$, the definitions given for substituent groups in the following sections, describing compounds in groups A, B, C, D, E and F, apply only within the individual sections and the related claims. Thus, for example, the meaning conveyed by the term $R_1$ in the section describing group A compounds is not the same as that conveyed by the same term in the section describing compounds of group B, and the term is provided with a different definition in each section.

Preferred Compounds in Accordance with the Invention, Group A

Compounds in this group have the formula II, III, IV or V:—

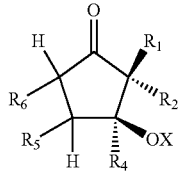
II

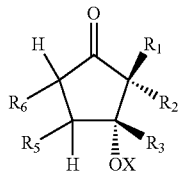
III

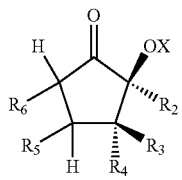
IV

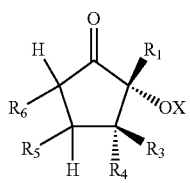
V wherein $R_1$, $R_2$, $R_3$, $R_4$, $R_5$ and $R_6$ can (independently) be hydrogen or any other appropriate moiety and X can be any appropriate moiety, excepting that at least one of $R_1$-$R_6$ is a group —SR, as previously defined, and provided that said compounds cannot be of formula I, as previously defined.

Preferably, the group OX is not bound to the same ring carbon atom as a group —SR. It is further preferred that $R_5$ is —SR. In preferred embodiments, only one group —SR is bound to the cyclopentenone ring.

When not a group —SR, $R_1$, $R_2$, $R_3$ and $R_4$ can be hydrogen, halogen, substituted or unsubstituted alkyl, substituted or unsubstituted alkenyl, substituted or unsubstituted alkynyl, substituted or unsubstituted alkoxy, substituted or unsubstituted aminoalkyl, substituted or unsubstituted alkylthio, substituted or unsubstituted alkylsulfinyl, substituted or unsubstituted alkylsulfonyl, substituted or unsubstituted carbocyclic aryl, substituted or unsubstituted aralkyl, or a substituted or unsubstituted heteroaromatic or heteroalicyclic group. Where a plurality of carbon atoms are present in any of $R_1$, $R_2$, $R_3$, or $R_4$, excepting where it is —SR, it is preferred that between 2 and 20 (more preferably between 3 and 15) carbon atoms are present. $R_1$, $R_2$, $R_3$ and $R_4$ may comprise cyclic or non-cyclic groups. A functional group (e.g. carboxylic acid group) may be included. Preferably, however, $R_1$, $R_2$, $R_3$ and $R_4$ are not halogen.

When not a group —SR, $R_5$ and $R_6$ can be (independently) hydrogen or halogen. Desirably a plurality of $R_1$, $R_2$, $R_3$, $R_4$, $R_5$ and $R_6$ are hydrogen.

X can be any moiety. Desirably it comprises one or more carbon atoms. Preferably it is a silicon-containing group or it contains another heteroatom (e.g. oxygen, nitrogen, or sulphur). If a heteroatom is present, desirably it is present as part of a chain (e.g. hydrocarbyl chain). Most preferably, X comprises one or more silicon atoms as part of a hydrocarbyl chain (which may optionally include one or more functional groups). A silicon atom of the silicon-containing group is preferably directly attached to the oxygen atom of the —OX group, although this is not essential, since a linker may be used.

X therefore includes:—

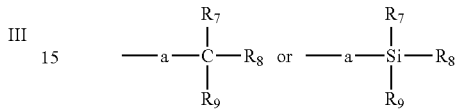

wherein $R_7$, $R_8$ and $R_9$ are defined as for $R_1$, $R_2$, $R_3$ and $R_4$ above, but are preferably alkyl, substituted alkyl, aryl or substituted aryl; and wherein α is absent or is a moiety providing a linkage with the oxygen of —O—X (e.g. it is a hydrocarbyl linker, such as $CH_2$, $C_2H_4$ or $C_3H_6$). It is preferred that none of $R_7$, $R_8$ and $R_9$ are a group —SR.

Preferably X is hydrophobic and/or lipophilic. It can have only 1, 2 or 3 carbon atoms. Desirably, however, it comprises at least 4 carbon atoms. A maximum number of carbon atoms for X has not been determined. However, without being bound by theory, it is envisaged that compounds in group A can include up to 50 or up to 20 carbon atoms (more preferably up to 12 carbon atoms and most preferably up to 8 carbon atoms).

If a side chain other than —SR is present at positions $R_3$ and/or $R_4$, it is preferred that it has fewer than 7 carbon atoms. More preferably it has no more than 3 carbon atoms. However it is most preferred that $R_3$ and/or $R_4$ are hydrogen.

From the foregoing description it will be appreciated that compounds of the present invention includes various 4- and -5 oxacyclopentanones. An oxa moiety (provided by —O—X) may be present at both 4 and 5 positions of the cyclopentanone ring (in either cis or trans form), however this is not preferred, particularly where both groups —O—X are —OH. The —O—X group may be provided twice at the 4 position and/or at the 5 position, if desired.

The preferred compounds of group A include those of formula (a) or (b):—

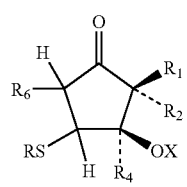
(a)

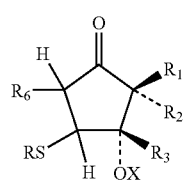
(b)

wherein:
R is as defined above, $R_1$ and $R_2$ are, independently, hydrogen, halogen, substituted or unsubstituted alkyl, substituted or unsubstituted alkenyl, substituted or unsubstituted alkynyl, substituted or unsubstituted aminoalkyl, substituted or unsubstituted alkylthio, substituted or unsubstituted alkylsulfinyl, substituted or unsubstituted alkylsulfonyl, substituted or unsubstituted carbocyclic aryl, substituted or unsubstituted aralkyl, or substituted or unsubstituted heteroaromatic or heteroalicyclic, $R_3$ and $R_4$ are hydrogen, $R_6$ is hydrogen or a halogen, and X has the formula:—

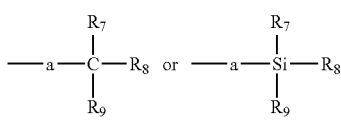

wherein $R_7$, $R_8$ and $R_9$ are, independently, hydrogen, halogen, substituted or unsubstituted alkyl, substituted or unsubstituted alkenyl, substituted or unsubstituted alkynyl, substituted or unsubstituted alkoxy, substituted or unsubstituted aminoalkyl, substituted or unsubstituted alkylthio, substituted or unsubstituted alkylsulfinyl, substituted or unsubstituted alkylsulfonyl, substituted or unsubstituted carbocyclic aryl, substituted or unsubstituted aralkyl, or substituted or unsubstituted heteroaromatic or heteroalicyclic, and "a" is absent or a linking group, optionally a hydrocarbyl linking group;

or with formula (c) or (d):—

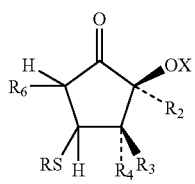
(c)

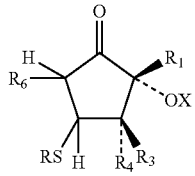
(d)

wherein:

R is as defined above, $R_1$ and $R_2$ are hydrogen, $R_3$ and $R_4$ are, independently, hydrogen, halogen, substituted or unsubstituted alkyl, substituted or unsubstituted alkenyl, substituted or unsubstituted alkynyl, substituted or unsubstituted aminoalkyl, substituted or unsubstituted alkylthio, substituted or unsubstituted alkylsulfinyl, substituted or unsubstituted alkylsulfonyl, substituted or unsubstituted carbocyclic aryl, substituted or unsubstituted aralkyl, or substituted or unsubstituted heteroaromatic or heteroalicyclic, and $R_6$ and X are as defined above.

In a formula (a), (b), (c) and (d) X is preferably an Si-containing group and can comprise at least 4 carbon atoms. $R_7$, $R_8$ and $R_9$ are preferably substituted alkyl, aryl or substituted aryl groups.

Even more preferred compounds of group A have the formula (c) or (d), wherein $R_3$ and/or $R_4$ comprises no more than 7 carbon atoms. Others have the formula (c) or (d), wherein a hydrocarbyl side chain is not present at positions $R_3$ and/or $R_4$ and the latter are preferably hydrogen.

Some non-limiting examples of group A compounds within the scope of the present invention are set out below (R and S, as well as cis or trans forms are all covered, where applicable, and therefore the stereochemistry should not be construed as limiting:—

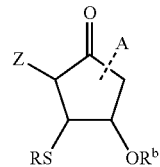
(i)

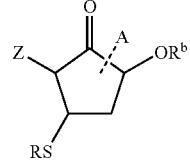
(ii)

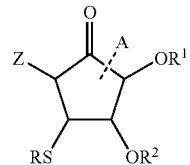
(iii)

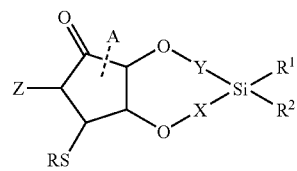
(iv)

"A" indicates that one or more additional substituents may optionally be present on the cyclopentanone ring. If present, such substituents are preferably small groups or atoms and desirably do not include more that 7 or more than 3 carbon atoms. However, it is preferred that such additional substituents are not present—i.e. that A is absent. "Z" is preferably H or halogen (e.g. chlorine).

In compounds (i) and (ii) show above, "$R^b$" is a moiety incorporating up to 8 carbon atoms or a moiety incorporating one or more heteroatoms (preferably at least one Si atom) and up to 50 carbon atoms. $R^b$ is preferably a hydrocarbyl group that is optionally substituted.

In compound (iii) shown above, $R^1$ and $R^2$ are such that either:— a) at least one of $R^1$ and $R^2$ incorporates one or more heteroatoms (preferably at least one Si atom) and up to 30 or up to 50 carbon atoms, or b) at least one of $R^1$ and $R^2$ comprises up to 8 carbon atoms.

Preferably at least one of $R^1$ and $R^2$ is an optionally substituted hydrocarbyl group. The other of $R^1$ and $R^2$ may also be an optionally substituted hydrocarbyl group, but this is not essential. It may for example be hydrogen or another atom or group. $R^1$ and $R^2$ may be the same or different.

In compound (iv) shown above, X and/or Y may be absent or may be groups or atoms providing a linkage between O and Si. X and/or Y may, for example, be an optionally substituted hydrocarbyl group. For example X and/or Y maybe $CH_2$, $C_2H_4$ or $C_3H_6$. X and Y may be the same or different. $R^1$ and $R^2$ can be any appropriate moieties and may be the same or different. Preferably however at least one (desirably both) of $R^1$ and $R^2$ is a hydrocarbyl group. The hydrocarbyl group may be optionally substituted. The hydrocarbyl group preferably comprises up to 30 or up to 50 carbon atoms.

Compounds in group A can exist in the form of a least two enantiomers and all such enantiomers, unequal mixtures thereof and racemates are encompassed by the present invention. Both R- and S-enantiomers of group A compounds are useful. They can each be provided in a form substantially free of the other enantiomer (e.g. at least 75%, 85%, 90%, 95% or 99% free (w/w)). Mixtures of enantiomers (e.g. racemic mixtures) may however also be used.

The most preferred compounds in this group are the 3-(SR) derivatives of R-(+) and S(-)-4-tert-butyldimethylsilyloxy-cyclopentan-1-one, particularly the S enantiomers. These include the following:—

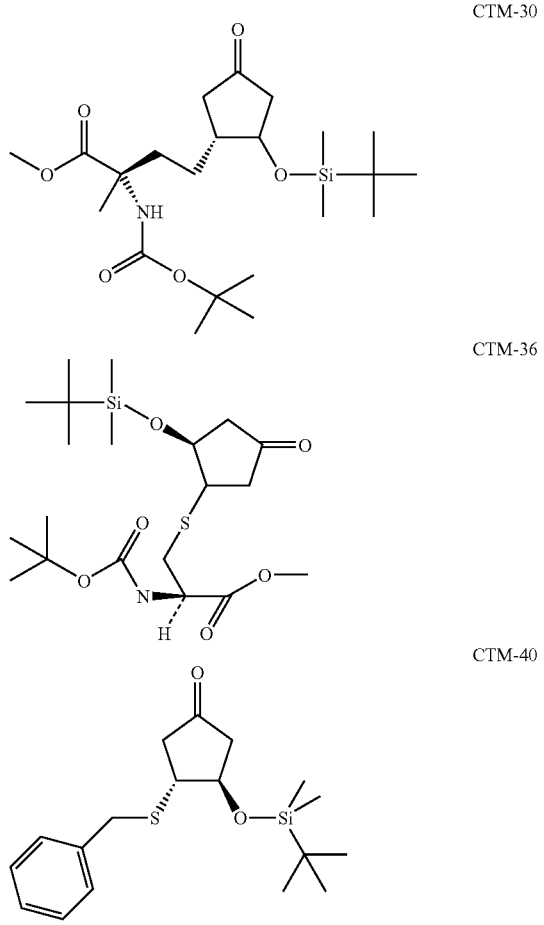

CTM-30

CTM-36

CTM-40

Another preferred sub-group of compounds within group A are those wherein $R_1$ and $R_2$ in formulae II, III, IV, V, (a) and (b) are both methyl groups. Examples of some of these preferred compounds are given in Example 8 below. Further preferred group A compounds, wherein $R_1$ and $R_2$ in formulae II, III, IV, V, (a) and (b) are both hydrogen are described in Examples 9 and 10 below. Methods of preparing group A compounds are also described in Examples 8-10.

Preferred Compounds in Accordance with the Invention, Group B

Compounds of group B have the formula VI:—

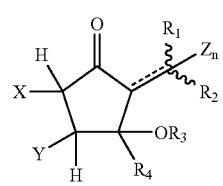

IV wherein:—
$R_1$ is H, or a substituted or unsubstituted alkyl or alkenyl group containing 1 to 3 carbon atoms;
$R_2$ is a substituted or unsubstituted alkyl, alkenyl, alkynyl, aryl, aralkyl aralkenyl, or aralkynyl group, optionally including at least one heteroatom in its carbon skeleton, and containing 1-12 carbon atoms;
$R_3$ is a substituted or unsubstituted alkyl, alkenyl, alkynyl, aryl, aralkyl aralkenyl, or aralkynyl group, optionally including at least one heteroatom in its carbon skeleton, and containing 1-12 carbon atoms, or a silyl group;
$R_4$ is H, or an alkyl group containing 1-3 carbon atoms;
X is H, a halogen, or an alkyl group containing 1-3 carbon atoms;
Y is a group —SR as herein before defined;
Z is a group —SR as herein before defined;
n is 1 or 0;
the bond shown as ---- is present when n is 0 and absent when n is 1; and
$R_2$ is cis- or trans- with respect to the carbonyl carbon in the cyclopentene ring when the bond shown as ---- is absent.

$R_2$ and $R_3$, independently, can be substituted with one or more =O, —$OR_5$, —$COOR_5$ and/or a halogen (preferably fluorine) group or atom, wherein $R_5$ is, independently, hydrogen or an alkyl group containing up to 4 carbon atoms. $R_5$ preferably is hydrogen or a methyl group.

$R_2$ and $R_3$, independently, can be unsubstituted.

When present, the heteroatom in the carbon skeleton of $R_2$ and/or $R_3$ is preferably oxygen, nitrogen or sulphur.

$R_1$ is preferably hydrogen or an unsubstituted alkyl (preferably methyl) group; hydrogen being more preferred.

$R_4$ is preferably hydrogen or a methyl group; hydrogen being more preferred.

Each of $R_2$ and $R_3$, independently, can be a substituted or unsubstituted, straight chain, branched and/or cyclo alkyl, alkenyl, or alkynyl group.

In a preferred embodiment, $R_2$ is a substituted or unsubstituted heterocyclic, aralkyl or aryl group. Thus, $R_2$ can be a substituted or unsubstituted phenyl, thiophenyl, or pyridinyl group. In more preferred embodiments, $R_2$ is an unsubstituted thiopheneyl, pyridinyl, phenyl, dimethylphenyl, halophenyl or alkoxyphenyl group. The halophenyl group is preferably a fluorophenyl group and the alkoxyphenyl group is preferably a methyloxyphenyl group.

When $R_2$ is a substituted or unsubstituted alkyl, alkenyl or alkynyl group it preferably includes up to 10, 9, 8, 7, 6, 5, 4, or 3 carbon atoms. In preferred embodiments, $R_2$ contains the 7, 3 or 2 carbon atoms and is preferably an alkyl group. In especially preferred embodiments $R_2$ is $C_7H_{15}$, iso-propyl, or ethyl.

$R_3$ can be a substituted or unsubstituted alkyl or aralkyl group and, in preferred embodiments $R_3$ includes a carboxyl and/or a carbonyl group.

$R_3$, in preferred embodiments, is a substituted or unsubstituted straight chain, branched and/or cycloalkyl group. $R_3$ preferably contains 5, 6, 7, or 8 carbon atoms when it includes or is a cycloalkyl group and 5 or fewer carbon atoms when it is a straight chain or branched alkyl group. In other embodiments $R_3$ is an aralkyl group and preferably contains 6, 7, or 8 carbon atoms. When $R_3$ is a straight chain or branched alkyl group it, more preferably, contains 4, or 5 carbon atoms. Preferred cycloalkyl groups are cyclohexyl groups and the preferred aryl group is phenyl.

In preferred embodiments, $R_3$ is a succinyl (i.e., a 1-oxo-3-carboxyprop-1-yl) group, or derivative. The derivative can be a 2-methylsuccinyl (i.e., a 1-oxo-2-methyl-3-carboxyprop-1-yl) group, or a group wherein two of the carbon atoms of the succinyl moiety form part of a saturated or unsaturated ring. Thus, the derivative can be a 2-carboxyphenylcarbonyl or a 2-carboxycyclohexylcarbonyl group.

In further embodiments, $R_3$ includes a carbonyl group α to the oxygen atom bound to the cyclopentenone ring.

When $R_3$ is a silyl group it is, preferably, a tri(organo)silyl group. Each of the organo-groups can be a substituted or unsubstituted alkyl, aryl and/or aralkyl group, optionally including at least one heteroatom in its carbon skeleton. Any combination of three such groups (e.g. one alkyl group, one aralkyl group and one aryl group; one or two alkyl groups combined with two or one aryl or aralkyl groups; etc.) can be present. Where alkyl groups are present, they preferably have from 1 to 5 carbon atoms. Where aryl or alkaryl groups are present, preferably they have at least 6 or 7 carbon atoms respectively. Preferred aryl groups include phenyl groups and preferred aralkyl groups include benzyl groups. If desired, the alkyl, silyl, or tri(organo)silyl groups, benzyl or phenyl groups can include various hetero atoms and/or groups (e.g. one or more hydroxyl groups and/or halogen atoms may be present in them). Thus the organo-groups can be substituted with one or more =O, —$OR_5$, —$COOR_5$ and/or halogen (preferably fluorine) group or atom, wherein $R_5$ is, independently, hydrogen or an alkyl group containing up to 4 carbon atoms. $R_5$ preferably is hydrogen or a methyl group.

Group B compounds can exist in the form of a least two enantiomers and all such enantiomers, unequal mixtures thereof and racemates are encompassed by the present invention. Both R- and S-enantiomers of group B compounds are useful. They can each be provided in a form substantially free of the other enantiomer (e.g. at least 75%, 85%, 90%, 95% or 99% free (w/w)). Mixtures of enantiomers (e.g. racemic mixtures) may however also be used.

Many group B compounds in accordance with the invention exist in both E and Z forms, i.e. with $R_2$ being cis- or trans to the carbonyl carbon in the cyclopentenone ring. The present invention encompasses all such individual isomers and mixtures thereof.

Preferred group B compounds have significant differences from the punaglandins and prostaglandins that have been disclosed previously for therapeutic purposes. In particular, it can be noted that compounds of group B in accordance with the present invention do not require the presence of two long aliphatic lateral side chains (usually each comprising more than 7 carbon atoms) attached to the cyclopentanone ring structure. Thus, although two such chains can be included if desired, preferred compounds of the present invention do not include the presence of the two long aliphatic lateral side chains associated with prostaglandins.

The preferred embodiments of $R_2$ and $R_3$ are those illustrated in the following formulae, especially in formulae CTC-31a, 2a, 3a, 4a, 5a, 6a and 45a. Each of the embodiments of $R_2$ (in formula VI), given below, can be used with alternative embodiments of $R_3$ (in formula VI) to those illustrated in the individual formulae and vice versa.

Preferred group B compounds include the following:—

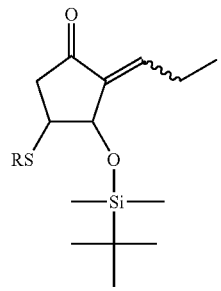

CTC-31a

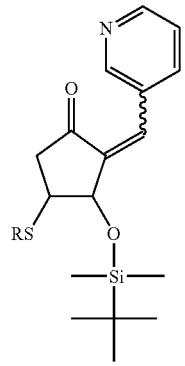

CTC-32a

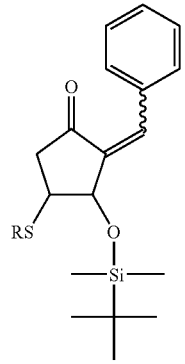

CTC-33a

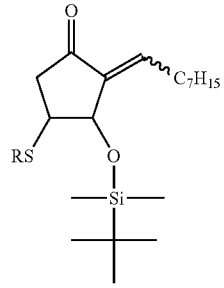

CTC-34a

-continued
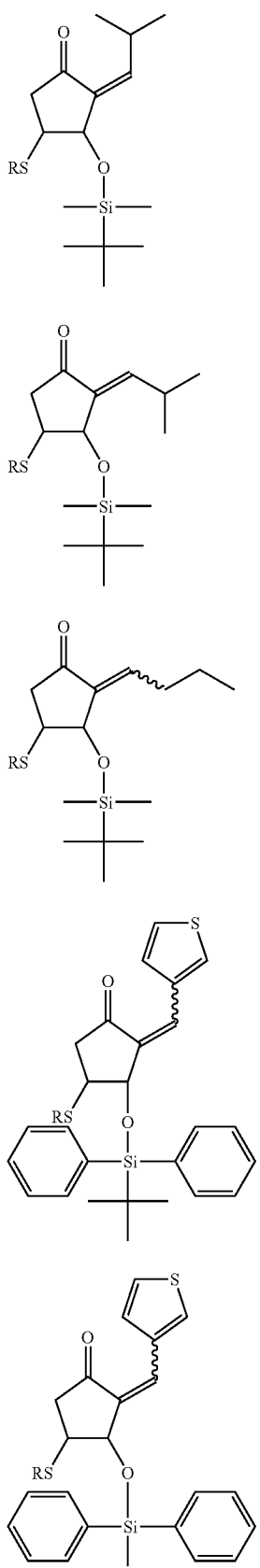
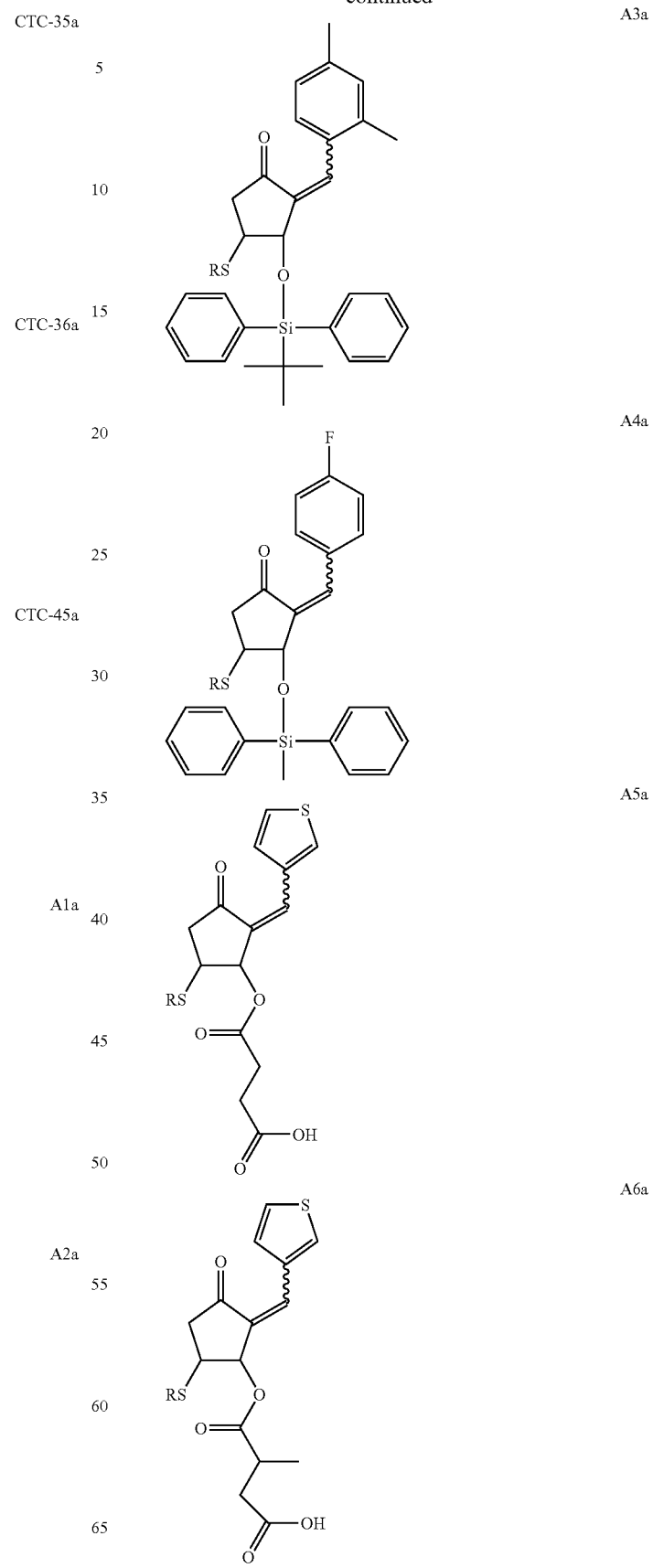

-continued
A7a
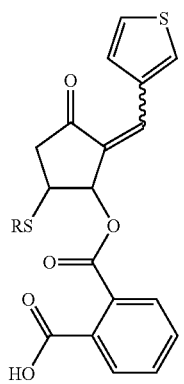
A8a
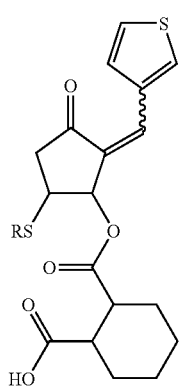
A9a
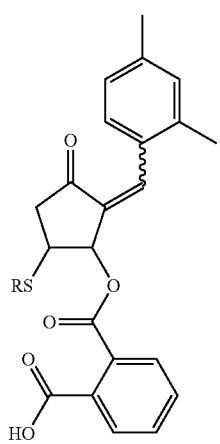
A10a
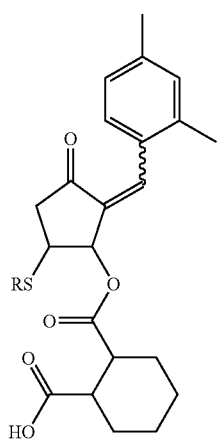
-continued
A11a
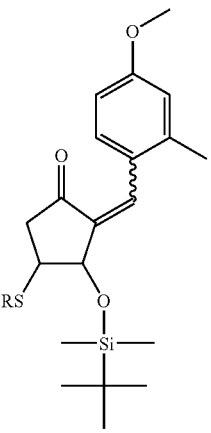
A12a
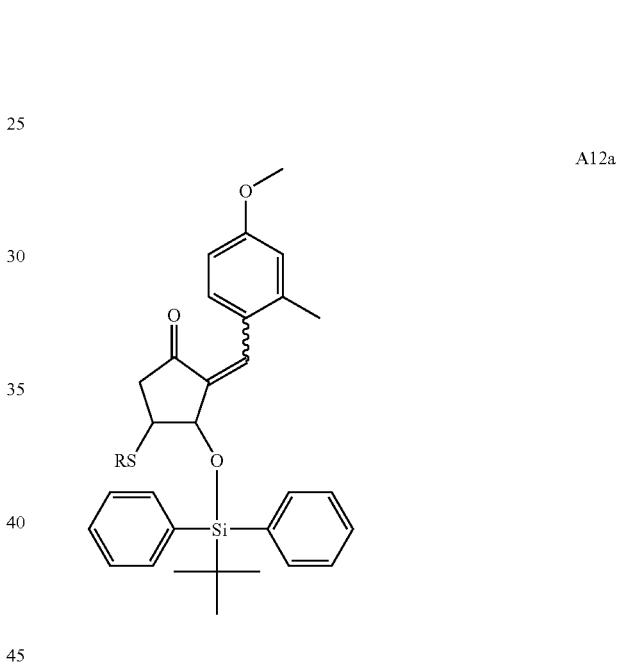
A14a
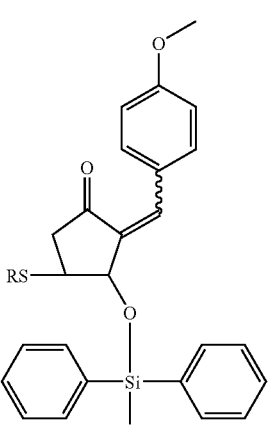

-continued

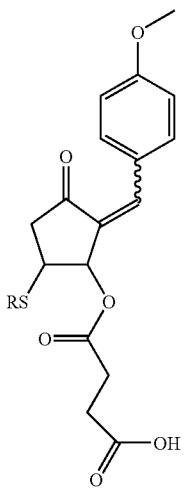

A15a

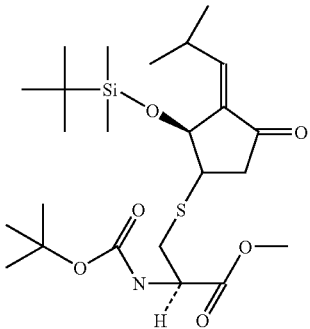

CTM-37

In the foregoing formulae, R is as defined above and groups joined by bonds shown as ˜˜˜ can be orientated in either the cis- or trans-configurations and both such forms (i.e., the E and Z forms) of the depicted compounds lie within the scope of the present invention. The latter applies throughout this specification.

Additional preferred compounds within this group have similar formulae to those set out immediately above, excepting that they include an additional group —S—CH$_2$—R bound to the first carbon atom in the side chain carried by the ring carbon atom adjacent (α) to the carbonyl ring carbon atom, in place of the double bond to the ring shown in the formulae.

Compounds of group B can be prepared from their cyclopent-2-en-1-one analogues in which Y is hydrogen, by employing general method A, as described below or one of the techniques described in Example 1. The required cyclopent-2-enone analogues can be prepared by one of the preparative methods described in WO01/44254. Compounds in this group which include an additional group —SR, in place of the double bond to the ring in the side chain a to the carbonyl ring carbon atom, can also be prepared by using an adaptation of general method A or that described in Example 1.

Preferred Compounds in Accordance with the Invention, Group C

Compounds of group C have the structure set out in formula VII:—

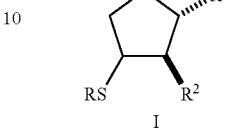

VII

I wherein $R^1$ is a saturated or unsaturated, branched or straight alkyl chain terminated with a COOX group and includes 4 to 15 carbon atoms, X is non-polar and preferably H or a $C_1$-$C_6$ alkyl group, $R^2$ is H or a straight chain $C_1$-$C_{20}$ saturated alkyl group, and R is as herein before defined.

In preferred compounds of group C, $R^1$ and $R^2$ are as defined above, except that $R^2$ is preferably not H or n-butyl when $R^1$ is —CH$_2$CH═CH(CH$_2$)$_3$COOH.

$R^1$ can include 4, 5, 6, 7, 8, 9, 10, 11, 12, 13, 14, or 15 carbon atoms. However, $R^1$ preferably includes seven carbon atoms. X is preferably a methyl or tert-butyl group and $R^2$ a $C_3$-$C_{10}$ and, more preferably, a $C_4$-$C_8$ saturated alkyl group. $R^2$ can include 3, 4, 5, 6, 7, 8, 9 or 10 carbon atoms, but is most preferably a $C_4$, $C_6$ or $C_8$ alkyl group. Thus, in preferred embodiments of group C compounds in accordance with the invention, $R^1$ is —CH$_2$CH═CH(CH$_2$)$_n$ COOX, $R^2$ is H, $C_4H_9$ or $C_8H_{17}$, n is 0-11 and X is H or a $C_1$-$C_6$ saturated alkyl group. n is preferably 1, 2, 3, 4, 5, 6, 7, 8, 9, 10 or 11 and most preferably 3.

The alkyl chain in $R^1$ is also preferably unsaturated, preferably unbranched and, when unsaturated, can include a single double bond between the second and third carbon atoms from the cyclopentenone ring. When the $R^1$ alkyl chain includes such a double bond, it is preferably in the cis- or (Z) form, although it can be in the trans- or (E) form.

Compounds in group C can exist in the form of a least two enantiomers and all such enantiomers, unequal mixtures thereof and racemates are encompassed by the present invention. Both R- and S-enantiomers of group C compounds are useful. They can each be provided in a form substantially free of the other enantiomer (e.g. at least 75%, 85%, 90%, 95% or 99% free (w/w)). Mixtures of enantiomers (e.g. racemic mixtures) may however also be used.

Many compounds in group C exist in both cis- and trans-forms, i.e. with $R^1$ and $R^2$ being cis- or trans to each other within the cyclopentenone ring. The present invention encompasses all such individual isomers and mixtures thereof, together with their uses.

Preferred compound in group C include the following:—

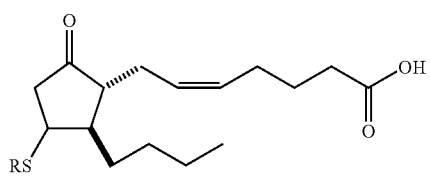

CTP-15a

-continued

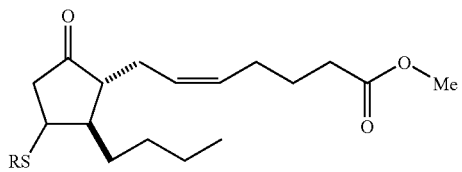
CTP-16a

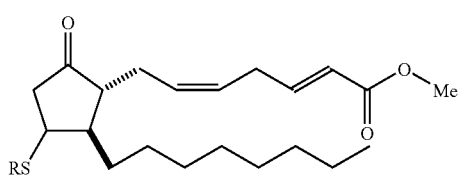
CTP-17a

In the foregoing formulae, R is as defined above.

Compounds in group C may be prepared from their cylco-pent-2-en-1-one analogues by a technique of the type described in Example 1. The required cylcopent-2-en-1-one analogues can be prepared by a technique of the nature described by C. B. Chapleo, S. M. Roberts and R. F. Newton in *J. Chem. Soc., Perkin Trans.* 1, 1980, 2088-2092, or in example 2.

Preferred Compounds in Accordance with the Invention, Group D

Compounds of group D have the structure set out in formula VIII:—

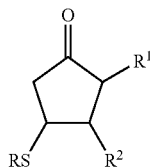
VIII wherein each of $R^1$ and $R^2$ is H, or a saturated or unsaturated branched or straight chain alkyl group, both $R^1$ and $R^2$ together include between 4 and 12 carbon atoms, and R is as hereinbefore described.

Preferably, $R^1$ is a saturated or unsaturated branched or straight chain alkyl group including up to 5, 6, 7, 8, 9, 10, 11 or 12 carbon atoms and, preferably, at least 4 carbon atoms. $R^2$ is preferably H or a straight chain $C_1$-$C_4$ saturated alkyl group.

$R^1$ is more preferably unsubstituted and $R^2$ is more preferably H. In preferred compounds of group D, $R^1$ is unsaturated, preferably unbranched, and can include a single double bond between the second and third carbon atoms from the cyclopentanone ring When the $R^1$ alkyl chain includes such a double bond, it is preferably in the cis- or (Z) form, although it can be in the trans- or (E) form. In more preferred embodiments, $R^1$ includes 5, 7, or 12 carbon atoms and $R^2$ is H. Thus, in preferred embodiments, $R^1$ is $-CH_2CH=CH(CH_2)_n CH_3$, $R^2$ is H and n is 0-8. n is preferably 1, 2, 3, 4, 5, 6, 7, or 8 and most preferably 1, 3 or 8.

Compounds in group D can exist in the form of a least two enantiomers and all such enantiomers, unequal mixtures thereof and racemates are encompassed by the present invention. Both R- and S-enantiomers of group D compounds are useful. They can each be provided in a form substantially free of the other enantiomer (e.g. at least 75%, 85%, 90%, 95% or 99% free (w/w)). Mixtures of enantiomers (e.g. racemic mixtures) may however also be used.

Many compounds in group D exist in both cis- and trans-forms, i.e. with $R^1$ and $R^2$ being cis- or trans to each other within the cyclopentenone ring. The present invention encompasses all such individual isomers and mixtures thereof, together with their uses.

Preferred compounds in group D include the following:—

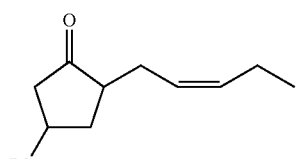
CTC-73a

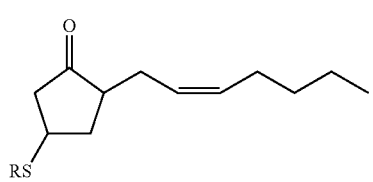
CTC-74a

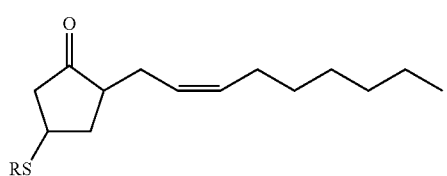
CTC-83a

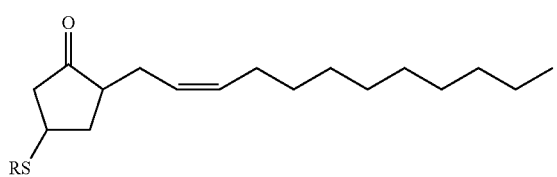
CTC-84a

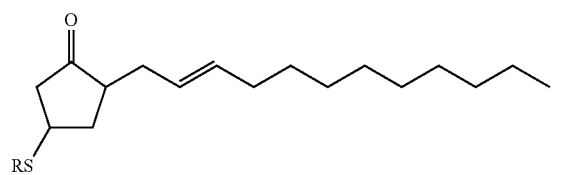
CTC-85a

In the foregoing formulae, R is as defined above.

Compounds in group D may be prepared from their cyclopent-2-en-1-one analogues by a technique of the type described in Example 1. The required cylcopent-2-en-1-one analogues can be prepared by a technique of the nature described in Example 3.

Preferred Compounds in Accordance with the Invention, Group E

The compounds in group E comprise a family of cyclohexenone derivatives that have the structure set out in formula IX:—

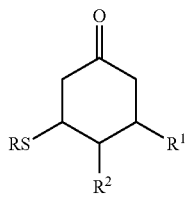

I wherein $R^1$ and $R^2$ are H, or an —$OR^3$ group in which $R^3$ is a substituted or unsubstituted alkyl, alkenyl, alkynyl, aryl, aralkyl aralkenyl, or aralkynyl group containing 4-12 carbon atoms, that optionally includes at least one heteroatom in its carbon skeleton, $R^1$ and $R^2$ cannot both be H, and R is as hereinbefore defined.

Preferably, only one of $R^1$ and $R^2$ is an —$OR^3$ group, in which $R^3$ is previously defined, and the other is H. In all group E compounds of the invention, $R^3$ is preferably an alkyl group that includes a heteroatom in its carbon skeleton. The heteroatom is preferably silicon and, in preferred embodiments, $R^3$ is a trialkylsilyl group, preferably a tert-butyldimethylsilyl group.

Compounds in group E can exist in the form of at least two enantiomers and all such enantiomers, unequal mixtures thereof and racemates are encompassed by the present invention. Both R- and S-enantiomers of group E compounds are useful. They can each be provided in a form substantially free of the other enantiomer (e.g. at least 75%, 85%, 90%, 95% or 99% free (w/w)). Mixtures of enantiomers (e.g. racemic mixtures) may however also be used.

Many compounds in accordance with the invention exist in both cis- and trans-forms, i.e. with $R^1$ and $R^2$ being cis- or trans- to each other in the cyclohexenone ring. The present invention encompasses all such individual isomers and mixtures thereof, together with their uses.

Preferred compounds in group E include the following:—

CTM-22a

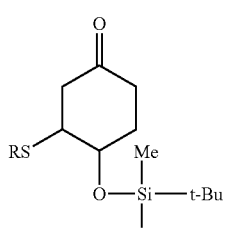

CTM-25a

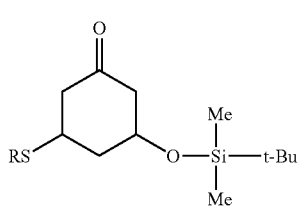

In the foregoing formulae, R is as defined as above.

Compounds in group E may be prepared from their cyclohex-2-en-1-one analogues by a technique of the type described in Example 1 or 6. The required cyclohex-2-en-1-one analogues can be prepared by a technique of the nature described in Example 4.

Preferred Compounds in accordance with the Invention, Group F

The compounds in group F comprise a family of cyclopent-2-en-1-one derivatives, in which at least one group —SR is bonded to a ring carbon atom.

Preferred compounds in group F have the formula X:—

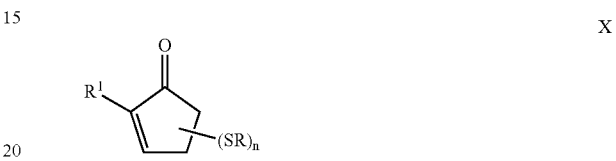

X wherein $R^1$ is hydrogen, or a substituted or unsubstituted alkyl, alkenyl, alkynyl, aryl, aralkyl aralkenyl, or aralkynyl group, optionally including at least one heteroatom in its carbon skeleton, R is as previously defined and n is 1-3. In preferred embodiments $R^1$ includes at least one —SR group.

In preferred group F compounds, n is one. An —SR group can be bonded to the ring carbon atom in the 3 and/or 4 position.

$R^1$ is preferably a group —$R^2$—SR, wherein R and, preferably, the group —SR are as previously defined and $R^2$ is a branched or straight chain alkyl or alkenyl group. $R^2$, preferably, includes up to 6, 5, 4, 3, 2, or 1 carbon atoms and is most preferably saturated.

Many compounds in group F can exist in the form of at least 2 enantiomers and all such enantiomers, unequal mixtures thereof and racemates are encompassed by the present invention. Both R- and S-enantiomers of group F compounds are useful. They can each be provided in a form substantially free of the other enantiomer (e.g. at least 75%, 85%, 90%, 95% or 99% free (w/w)). Mixtures of enantiomers (e.g. racemic mixtures) may however also be used.

Many compounds in group F exist in both cis- and trans-forms, i.e. with a first group —SR being cis- or trans- to a second group —SR across the cyclopentenone ring. The present invention encompasses all such individual isomers and mixtures thereof, together with their uses.

Preferred compounds in group F include the following:—

CTC-109

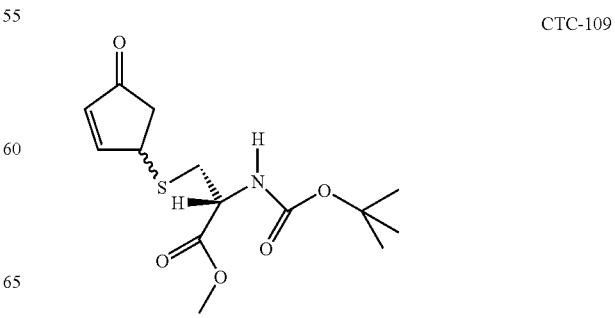

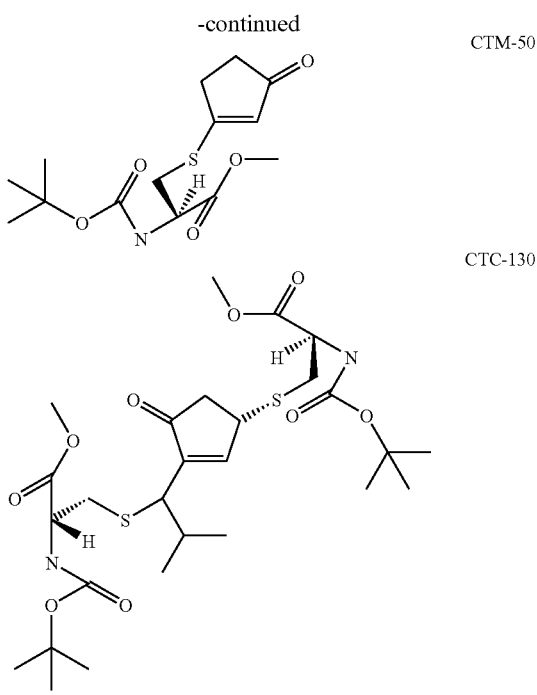

Compound CTC-130 can be prepared from compound CTC-35 or CTC-36, which are described in WO 01/44254, using a technique of the same general type as that described in Example 1 below. Compound CTC-109 can be prepared by the method set out in Example 5 below and compounds CTM-50 and CTC-130 can be prepared by analogous techniques.

Medical Uses for Compounds in Accordance with the Invention

The preferred uses for compounds in accordance with the invention include the treatment of disorders which can be treated in a host by the activation of a heat shock transcription factor (e.g. HSF1), by the induction of heat shock proteins (e.g. hsp70) and/or by the inhibition of NF-κB.

Certain preferred compounds in accordance with the invention can be used in therapeutic applications that involve activating HSF and inhibiting the activity of NF-κB. Thus, in accordance with the invention, such compounds can be used to treat diseases or conditions in which such activity is indicated or can be of advantage. They can also be used in the manufacture of medicaments for use in such treatments. Preferred therapeutic and diagnostic applications for such compounds are discussed below.

It should be appreciated that certain compounds in accordance with the invention do not exhibit activity in all of the respects discussed above. Such compounds, therefore, may only find use in those of the therapeutic and diagnostic applications detailed below where their properties are indicative of potential usefulness.

It should be appreciated that certain disorders, e.g. cancers, may be mediated by viruses and by non-viral factors. In the absence of any indication to the contrary, treatment of any given disorder is covered whether or not the disorder is mediated by viruses. It should also be appreciated that there is some overlap between the various categories of treatment discussed, i.e. the categories are not intended to be mutually exclusive.

1. Treatment of Viral-Mediated Disorders

NF-κB is implicated in the pathogenesis of certain viral infections. It is known that heat shock proteins (e.g. HSP70) can offer protection against the pathogenesis of viral infection. Compounds in accordance with the invention may be active in reducing the replication of viruses.

Compounds in accordance with the invention may be useful in treating viral-mediated disorders. These include disorders mediated by RNA viruses, as well as disorders mediated by DNA viruses.

Examples of viral disorders that may be treated using compounds in accordance with the invention include the following.

Diseases caused by or associated with members of the Adenoviridae family, including (but not limited to): diarrhea or intussusception caused by or associated with enteric adenoviruses, upper or lower respiratory tract infections (including the common cold or pneumonia) caused by or associated with respiratory adenoviruses; conjunctivitis, keratitis or trachoma caused by or associated with adenovirus infection of the eye; tonsillar or kidney infections caused by or associated with adenoviruses.

Diseases caused by or associated with members of the Arenaviridae family, including (but not limited to): Lassa fever caused by Lassa fever virus; meningitis caused by or associated with lymphocytic choriomeningitis virus; hemorrhagic fevers including (but not limited to) those caused by Machupo virus, Junin virus, Sabia virus, Guanarito virus or Tacaribe virus.

Diseases caused by or associated with members of the Astroviridae family, including (but not limited to): diarrhea caused by or associated with astroviruses.

Diseases caused by or associated with members of the Bunyaviridae family, including (but not limited to): hemorrhagic fever with renal syndrome, hantavirus pulmonary syndrome, or other diseases caused by or associated with hantaviruses including (but not limited to) Hantaan virus, Puumala virus, Seoul virus, Dobrava virus, Sin Nombre virus, bayou virus, Black Creek canal virus, New York 1 virus, Monogahela virus, Andes virus, Laguna Negra virus; arbovirus infections including (but not limited to) La Crosse encephalitis, California encephalitis, or other bunyavirus infections; Rift Valley fever, sandfly fever, Uukuniemi or other arbovirus infections associated with phleboviruses; Crimean-Congo hemorrhagic fever or other infections caused by Nairoviruses.

Diseases caused by or associated with members of the Caliciviridae family or related agents, including (but not limited to): hepatitis caused by or associated with hepatitis E virus, diarrhea caused by or associated with caliciviruses or small round structured viruses.

Diseases caused by or associated with members of the Coronaviridae family, including (but not limited to): lower or upper respiratory tract infections (including the common cold) caused by or associated with coronaviruses; diarrhea, enterocolitis or gastroenteritis caused by or associated with coronaviruses or toroviruses.

Diseases caused by or associated with members of the Filoviridae family, including (but not limited to): hemorrhagic fevers caused by Ebola or Marburg viruses.

Diseases caused by or associated with members of the Flaviviridae family, including (but not limited to): arbovirus infections, fevers or encephalitides including (but not limited to) yellow fever, Kyansur Forest disease, Omsk hemorrhagic fever, other tick-borne encephalitis infections, Rocio, Japanese encephalitis, St. Louis encephalitis, West Nile virus infection, Murray Valley encephalitis, Dengue fever, or Dengue hemorrhagic fever caused by or associated with flaviviruses; hepatitis caused by or associated with hepatitis C virus.

Diseases caused by or associated with members of the Hepadnaviridae family, including (but not limited to): hepatitis caused by or associated with hepatitis B virus.

Diseases caused by or associated with members of the Herpesviridae family, including (but not limited to): orolabial herpes, genital herpes, herpetic dermatitis, herpetic whitlow, zosteriform herpes simplex, ocular disease, encephalitis or neonatal herpes caused by or associated with herpes simplex viruses types 1 or 2; chickenpox, shingles, zoster-associated pain, pneumonia, encephalitis, fetal infection or retinal necrosis caused by or associated with varicella-zoster virus; transplant rejection, congenital infection, infectious mononucleosis, retinitis or other diseases of the immunocompromised caused by or associated with cytomegalovirus; infectious mononucleosis, lymphomas, carcinomas or other cancers caused by or associated with Epstein-Barr virus; exanthem subitum, roseola infantum, pneumonitis or hepatitis caused by or associated with human herpesviruses 6 or 7; Kaposi's sarcoma or other neoplastic disease caused by or associated with human herpesvirus 8 (KSV).

Diseases caused by or associated with members of the Orthomyxoviridae family, including (but not limited to): influenza, pneumonia, other respiratory infections, myositis, myoglobinuria, or Reye's syndrome caused by or associated with influenza viruses A, B or C.

Diseases caused by or associated with members of the Papovaviridae family, including (but not limited to): papillomas, comdylomas, neoplasias and carcinomas caused by or associated with papillomaviruses; diseases caused by BKV or JCV viruses; progressive multifocal leukoencephalopathy caused by polyomaviruses.

Diseases caused by or associated with members of the Parvovindae family, including (but not limited to): anemia, fever, fetal infection or hepatitis caused by or associated with parvorvirus B19.

Diseases caused by or associated with members of the Paramyxoviridae family, including (but not limited to): pneumonia, bronchiolitis, tracheobronchitis or croup caused by or associated with parainfluenza viruses; bronchiolitis or pneumonia caused by or associated with respiratory syncytial virus; encephalitis, measles or complications of measles including (but not limited to) pneumonia or sub-acute sclerosing panencephalitis (SSPE) caused by or associated with measles virus; mumps or complications of mumps including (but not limited to) orchitis or pancreatitis caused by or associated with mumps virus.

Diseases caused by or associated with members of the Picornaviridae family, including (but not limited to): hepatitis caused by or associated with hepatitis A virus; upper respiratory tract infections (including the common cold) caused by or associated with rhinoviruses or other respiratory picornaviruses; poliomyelitis caused by polioviruses; Bornholm disease, encephalitis, meningitis, herpangina, myocarditis, neonatal disease, pancreatitis, fever, conjunctivitis, chronic fatigue syndrome (ME) or hand, foot and mouth disease caused by coxsackieviruses or enteroviruses.

Diseases caused by or associated with members of the Poxviridae family, including (but not limited to): smallpox caused by smallpox virus; human forms of monkeypox or cowpox virus infections; infections with vaccinia virus including (but not limited to) complications of vaccination; orf or paravaccinia caused by parapoxviruses; molluscum contagiosum caused by molluscipoxviruses; infections with Tanapox virus.

Diseases caused by or associated with members of the Reoviridae family, including (but not limited to): diarrhea caused by or associated with rotaviruses.

Diseases caused by or associated with members of the Retroviridae family, including (but not limited to): acquired immune deficiency syndrome and associated disorders caused by or associated with human immunodeficiency virus (HIV); leukaemias, lymphomas, or myelopathies caused by or associated with HTLV viruses.

Diseases caused by or associated with members of the Rhabdoviridae family, including (but not limited to): rabies caused by rabies virus; other lyssavirus diseases including (but not limited to) those caused by Duvenhage or Mokola viruses.

Diseases caused by or associated with members of the Togaviridae family, including (but not limited to): rubella or congenital rubella syndrome caused by rubella virus; fever or encephalitis caused by eastern equine encephalitis virus, Venezuelan equine encephalitis virus, western equine encephalitis virus, Everglades virus or Semliki Forest virus; fever, rash, polyarthritis, myalgia or arthralgia caused by Sindbis virus, Ockelbo virus, Ross River virus, Barmah Forest virus, Chikungunya virus, O'nyong-nyong virus, Mayaro virus or Igo Ora virus.

Diseases caused by or associated with viroid-like agents, including (but not limited to): hepatitis caused by or associated with the delta agent (HDV).

Diseases caused by or associated with prions, including (but not limited to): Creutzfeld-Jakob disease (CJD), new variant CJD, GSS, and fatal familial insomnia.

Compounds of the present invention may be particularly useful in treating viral and other disorders affecting aquatic organisms (e.g. fish, crustaceans, etc.). Such disorders include disorders mediated by the snout ulcer virus, by the iridovirus, by the lymphocystis disease virus, etc.

Compounds in accordance with the invention may therefore be used in aquaculture. They may be used in food for aquatic organisms. Such food is within the scope of the present invention. It will generally be sold in sealed containers and labelled appropriately (e.g. as fish food, food for crustaceans, food for aquatic organisms, etc.). Alternatively, compounds in accordance with the invention may be used for water treatment or for direct application to aquatic organisms. Such compounds do not therefore need to be present in foodstuffs in order to be useful in aquaculture.

2. Treatment of Bacterial-Mediated Disorders

NF-κB is activated in response to bacterial infections.

Compounds in accordance with the invention can be useful in treating disorders arising from such infections, e.g. in treating NF-κB stimulated inflammation. Most commonly this will arise due to infection with gram negative bacteria. However it may also arise due to infection with gram positive bacteria (e.g. *S. aureus*).

3. Treatment of Disorders Mediated by Radiation

NF-κB is activated in response to radiation (e.g. UV-radiation).

Compounds in accordance with the invention can be useful in treating disorders mediated by radiation. Such disorders include cell and tissue trauma, cell and tissue ageing and cancer (e.g. skin cancer).

4. Treatment of Inflammation and of Disorders of the Immune System

NF-κB is activated in response to inflammatory cytokines. It is believed to be an early mediator of the immune and inflammatory responses.

Compounds in accordance with the invention can be useful in treating immune disorders (e.g. auto-immune disorders) and in treating inflammatory disorders. Examples of specific inflammatory disorders and disorders of the immune system that may be treated with such compounds include psoriasis, rheumatoid arthritis, multiple sclerosis, adult respiratory distress syndrome, hepatitis and/or cirrhosis, vascular inflammation (including lupus erythematosis disseminata), and inflammatory disorders of the gastro-intestinal tract (e.g. ulcers). Preferred amongst these uses is the treatment of psoriasis, particularly by the topical application of a compound in accordance with the invention formulated in a suitable composition, such as a cream, ointment or the like.

5. Treatment of Ischemia and Arteriosclerosis

NF-κB has been implicated in the pathogenesis of ischemia and anteriosclerosis. Compounds in accordance with the invention are therefore useful in treating such disorders, including reperfusion damage (e.g. in the heart or brain) and cardiac hypertrophy.

6. Treatment of Disorders Involving Cell Proliferation

NF-κB is implicated in cell proliferation.

Compounds in accordance with the invention can be useful as anti-proliferatives. They are therefore useful in treating inflammatory granulomas, neointimal proliferation in arterial and venous restenosis, and cancers (including lymphomas, leukemias, sarcomas, carcinomas and melanomas).

7. Treatment of Disorders Involving Damage to or Killing of Cells

Heat shock proteins are known to provide a cytoprotective effect.

Compounds in accordance with the invention can be useful in treating disorders involving damage to or killing of cells.

These disorders include chemical toxicity (e.g. due to ingestion of toxins, such as paraquat, or to overdosing with medicaments, such as paracetamol), oxidative cell damage, cell and tissue ageing trauma, hepatitis diabetes and the effect of burns. The inventive compounds, also, can be used to combat the effects of ageing in a human or animal, and to promote wound healing.

Other conditions of this general nature, that can be treated using compounds of the present invention, include oxidative stress and degenerative diseases, especially neuro-degenerative diseases such as BSE, new variant CJD and Alzheimer's disease.

8. Other Treatments

Cyclopentenone prostaglandins are of known utility in stimulating peroxisome proliferator activated receptors (PPARs). Compounds in accordance with the invention, thus, can be useful in treating diabetes (including complications arising therefrom). Such compounds can also be used in the treatment of disorders in which calcium loss or deficiency is implicated or involved (including bone disorders, skeletal disorders, dental disorders, developmental disorders, etc.).

9. Treatments Employing HSF Selective Compounds

Compounds in accordance with the present invention, particularly from groups C, D and E, can exhibit a capacity to trigger a heat shock response, activate HSF, or induce HSP expression, at a concentration at which they have no significant inhibitory effect on NF-κB activity.

In the light of the reports discussed in the opening paragraphs of this specification (see references 6, 7, 11 and 13), suggesting that compounds that include a cyclopentenone nucleus and have a capacity to activate HSF will also inhibit the activity of NF-κB, the selective action of compounds in accordance with the present invention is highly surprising. This unexpected property, however, renders these compounds uniquely useful in therapeutic applications where an effect upon the heat shock response is desirable, but any interruption of the normal NF-κB pathway would be unnecessary, undesirable or possibly deleterious. For example, because the NF-κB pathway plays an important role in T-cell mediated immune responses, its interruption could be immunosuppressive and, therefore, unless required in order to achieve a particular therapeutic objective, in principle should be avoided. Thus, these compounds can be particularly useful in the treatment of viral infections in which the pathology of the virus does not involve an inflammatory component, or in which the killing of cells by the virus is more important in the pathology than is any inflammatory response. Such viruses include those that do not depend upon NF-κB for their replication or do not have κB elements in their genomes. In addition to viral infections, HSF selective compounds can be used to treat other conditions which do not involve an inflammatory component, and they are particularly useful in cytoprotective applications.

Their selectivity allows HSF selective compound to be used in situations where it is desirable for an NF-κB mediated inflammatory immune response to be maintained. For example, they are especially useful in chronic or prophylactic treatments, as long term suppression of NF-κB activity and, consequently, of a patient's full immune response to infection, can lead to unwanted opportunistic infections. It is also known that long term suppression of NF-κB activity can cause apoptosis in the liver.

Thus, the HSF selective compounds in accordance with the invention can be used in therapeutic applications that involve activating HSF without significantly inhibiting the activity of NF-κB. Therefore, in accordance with the invention, these compounds can be used to treat diseases or conditions in which such activity is indicated or can be of advantage. They can also be used in the manufacture of medicaments for use in such treatments.

Heat shock proteins are known to provide a cytoprotective effect. Thus, HSF selective compounds can be useful in cytoprotective applications and in treating (including by prophylaxis) disorders involving damage to or killing of cells.

These disorders include chemical toxicity (e.g. due to ingestion of toxins, such as paraquat, or to overdosing with medicaments, such as paracetamol), oxidative cell damage, cell and tissue ageing trauma, hepatitis, diabetes and the effect of burns. These compounds, also, can be used to combat the effects of ageing in a human or animal, and to promote wound healing.

Other conditions of this general nature, that can be treated using HSF selective compounds, include oxidative stress and degenerative diseases, especially neuro-degenerative diseases such as BSE, new variant CJD and Alzheimer's disease.

The cytoprotective effect of HSF selective compounds also renders them useful in the treatment of ischemia and the damage resulting from episodes of ischemia and subsequent reperfusion. They can be employed to ameliorate the damaging effects of radiation and/or chemotherapy particularly, but not exclusively, when used in the treatment of cancer. These compounds can also be used to treat certain types of ulcers within the gastrointestinal tract.

As suggested in a foregoing section, compounds in accordance with the invention can be used as anti-viral agents. HSF selective compounds are useful, in general, in the treatment of viral infections wherein the pathological effects of the infecting virus can be reversed or prevented by a heat shock response. In particular, they can be employed to treat viral infections in which an inflammatory component is not significantly involved in or essential to the pathology of the infecting virus, the pathology of the virus does not involve an inflammatory component, or the killing of cells by the virus is more important than any inflammatory response. Such viruses include those that are not dependant upon NF-κB for their replication, or do not have κB elements in their genomes. Examples include parvoviruses, rotaviruses and those that infect the upper respiratory tract, including picornaviruses, coronaviruses and adenoviruses.

HSF selective compounds can also be used to treat infection with certain viruses that involve NF-κB and inflammation in their pathology, as the effects of many such organisms are reversed or prevented by the heat shock response and there may be other reasons why it may not be appropriate to administer an agent that disrupts the NF-κB pathway to a particular patient.

Examples of viral infections that can be treated with HSF selective compounds include infections with Picornaviruses (including Rhinoviruses and Hepatitis A virus), Reoviruses (including Rotavirus), Parvoviruses, Paramyxoviruses (including Sendai virus), Rhabdoviruses (e.g. vesicular stomatitis virus and rabies viruses), Filoviruses (e.g. Ebola virus), Adenovirus and Coronavirus. Viral infections with pathologies that involve inflammation and the NF-κB pathway, but which can be responsive to treatment with compounds in accordance with the invention, include Influenza virus infections.

Routes of Administration for Compounds in Accordance with the Invention

A medicament will usually be supplied as part of a pharmaceutical composition, which may include a pharmaceutically acceptable carrier. This pharmaceutical composition will generally be provided in a sterile form. It may be provided in unit dosage form. It will generally be provided in a sealed container, and can be provided as part of a kit. Such a kit is within the scope of the present invention. It would normally (although not necessarily) include instructions for use. A plurality of unit dosage forms may be provided.

Pharmaceutical compositions within the scope of the present invention may include one or more of the following: preserving agents, solubilising agents, stabilising agents, wetting agents, emulsifiers, sweeteners, colourants, odourants, salts (compounds of the present invention may themselves be provided in the form of a pharmaceutically acceptable salt—as explained in greater detail below), buffers, coating agents or antioxidants. They may also contain other therapeutically active agents in addition to a compound of the present invention.

Compounds of the present invention may themselves be provided in any suitable form—i.e. they may be used as such or may be used in the form of a pharmaceutically effective derivative. For example they may be used in the form of a pharmaceutically acceptable salt or hydrate. Pharmaceutically acceptable salts include alkali metal salts (e.g. sodium or potassium salts), alkaline earth metal salts (e.g. calcium or magnesium salts) aluminium salts, zinc salts, ammonium salts (e.g. tetra-alkyl ammonium salts), etc. Inorganic acid addition salts (e.g. hydrochlorides, sulphates, or phosphates) or organic acid addition salts (e.g. citrates, maleates, fumarates, succinates, lactates, propionates or tartrates) may be used.

Pharmaceutical compositions of the present invention may be provided in controlled release form. This can be achieved by providing a pharmaceutically active agent in association with a substance that degrades under physiological conditions in a predetermined manner. Degradation may be enzymatic or may be pH-dependent.

Pharmaceutical compositions may be designed to pass across the blood brain barrier (BBB). For example, a carrier such as a fatty acid, inositol or cholestrol may be selected that is able to penetrate the BBB. The carrier may be a substance that enters the brain through a specific transport system in brain endothelial cells, such as insulin-like growth factor I or II. The carrier may be coupled to the active agent or may contain/be in admixture with the active agent. Liposomes can be used to cross the BBB. WO91/04014 describes a liposome delivery system in which an active agent can be encapsulated/embedded and in which molecules that are normally transported across the BBB (e.g. insulin or insulin-like growth factor I or II) are present on the liposome outer surface. Liposome delivery systems are also discussed in U.S. Pat. No. 4,704,355.

A pharmaceutical composition within the scope of the present invention may be adapted for administration by any appropriate route, for example by the oral (including buccal or sublingual), rectal, nasal, topical (including buccal, sublingual or transdermal), vaginal or parenteral (including subcutaneous, intramuscular, intravenous or intradermal) routes. Such a composition may be prepared by any method known in the art of pharmacy, for example by admixing one or more active ingredients with a suitable carrier. In preferred embodiments, compounds in accordance with the invention are formulated into oral dosage forms and, therefore, are preferably provided in tablet or capsule form.

Different drug delivery systems can be used to administer pharmaceutical compositions of the present invention, depending upon the desired route of administration. Drug delivery systems are described, for example, by Langer (Science 249, 1527-1533 (1991)) and Illum and Davis (Current Opinions in Biotechnology 2m 254-259 (1991)). Different routes of administration for drug delivery will now be considered in greater detail.

(i) Oral Administration

Pharmaceutical compositions adapted for oral administration may be provided as capsules or tablets; as powders or granules; as solutions, syrups or suspensions (in aqueous or non-aqueous liquids); as edible foams or whips; or as emulsions. Tablets or hard gelatine capsules may comprise lactose, maize starch or derivatives thereof, stearic acid or salts thereof. Soft gelatine capsules may comprise vegetable oils, waxes, fats, semi-solid, or liquid polyols etc. Solutions and syrups may comprise water, polyols and sugars. For the preparation of suspensions, oils (e.g. vegetable oils) may be used to provide oil-in-water or water-in-oil suspensions.

An active agent intended for oral administration may be coated with or admixed with a material that delays integration and/or absorption of the active agent in the gastrointestinal tract (e.g. glyceryl monostearate or glyceryl distearate may be used).

Thus, the sustained release of an active agent may be achieved over many hours and, if necessary, the active agent can be protected from being degraded within the stomach. Pharmaceutical compositions for oral administration may be formulated to facilitate release of an active agent at a particular gastrointestinal location due to specific pH or enzymatic conditions.

(ii) Transdermal Administration

Pharmaceutical compositions adapted for transdermal administration may be provided as discrete patches intended to remain in intimate contact with the epidermis of the recipient for a prolonged period of time. For example, the active ingredient may be delivered from the patch by iontophoresis. (Iontophoresis is described in *Pharmaceutical Research*, 3(6):318 (1986).

(iii) Topical Administration

Pharmaceutical compositions adapted for topical administration may be provided as ointments, creams, suspensions, lotions, powders, solutions, pastes, gels, sprays, aerosols or oils. For topical administration to the skin, mouth, eye or other external tissues a topical ointment or cream is preferably used. When formulated in an ointment, the active ingredient may be employed with either a paraffinic or a water-miscible ointment base. Alternatively, the active ingredient may be formulated in a cream with an oil-in-water base or a water-in-oil base. Pharmaceutical compositions adapted for topical administration to the eye include eye drops. Here the active ingredient can be dissolved or suspended in a suitable carrier, e.g. in an aqueous solvent. Pharmaceutical compositions adapted for topical administration in the mouth include lozenges, pastilles and mouthwashes.

(iv) Rectal Administration

Pharmaceutical compositions adapted for rectal administration may be provided as suppositories or enemas.

(v) Nasal Administration

This includes not only administration to the nasal cavity, but also administration via the nasal cavity to another location—e.g. to the lungs.

Pharmaceutical compositions adapted for nasal administration may use solid carriers—e.g. powders (preferably having a particle size in the range of 20 to 500 microns). Powders can be administered in the manner in which snuff is taken, i.e. by rapid inhalation through the nose from a container of powder held close to the nose. Compositions adopted for nasal administration may alternatively use liquid carriers—e.g. include nasal sprays or nasal drops. These may comprise aqueous or oil solutions of the active ingredient.

Compositions for administration by inhalation may be supplied in specially adapted devices—e.g. in pressurised aerosols, nebulizers or insufflators. These devices can be constructed so as to provide predetermined dosages of the active ingredient.

(vi) Vaginal Administration

Pharmaceutical compositions adapted for vaginal administration may be provided as pessaries, tampons, creams, gels, pastes, foams or spray formulations.

(vii) Parenteral Administration

Pharmaceutical compositions adapted for parenteral administration include aqueous and non-aqueous sterile injectable solutions or suspensions. These may contain anti-oxidants, buffers, bacteriostats and solutes that render the compositions substantially isotonic with the blood of an intended recipient. Other components that may be present in such compositions include water, alcohols, polyols, glycerine and vegetable oils, for example. Compositions adapted for parenteral administration may be presented in unit-dose or multi-dose containers, for example sealed ampoules and vials, and may be stored in a freeze-dried (lyophilised) condition requiring only the addition of a sterile liquid carrier, e.g. sterile water for injections, immediately prior to use. Extemporaneous injection solutions and suspensions may be prepared from sterile powders, granules and tablets.

From the above description it will be appreciated that compositions of the present invention can be formulated in many different way.

Dosages

Dosages of a compound of the present invention can vary between wide limits, depending upon the nature of the treatment, the age and condition of the individual to be treated, etc. and physician will ultimately determine appropriate dosages to be used.

However, without being bound by any particular dosages, a daily dosage of a compound of the present invention of from 10 µg to 100 mg/kg body weight may be suitable.

More preferably the dosage is from 5 to 50 mg/kg body weight/day. The dosage may be repeated as often as appropriate. If side effects develop, the amount and/or frequency of the dosage can be reduced, in accordance with good clinical practice.

Research Uses

Compounds of the present invention are useful in research. For example, they can be used as research tools for the analysis of one or more of the following: HSF, NF-κB, the heat shock response, viral replication, viral-mediated disorders, bacterial-mediated disorders, disorders mediated by radiation (e.g. by UV-radiation), inflammatory disorders, disorders of the immune system, ischemia, arteriosclerosis, disorders involving cell proliferation (e.g. cancers), disorders involving damage to, or killing of cells (e.g. oxidative cell damage), and diabetes.

Other Uses

Compounds of the present invention can also be useful in treating plant viral disorders. Given that the basic mechanism of the heat shock response are believed to operate in a similar fashion in plants and animals and that it is reasonable to expect that direct antiviral effects will be produced by the compounds of invention in a similar fashion in plants and animals, the use of compounds of the present invention in treating viral infections of plants is within the scope of the present invention. These infections include, but are not limited to, infections by plants of geminiviruses, rhabdoviruses, caulimoviruses, bromoviruses, tobramoviruses, potyviruses and potexviruses. The use of compounds of the present invention in treating infections by viroids (including, but not limited to, potato spindle turnout viroid, hop stunt viroid, and coconut cadang-cadang viroid) is also within the scope of the invention.

Compounds of the present invention may be particularly useful in treating viral and other disorders affecting aquatic organisms (e.g. fish, crustaceans, etc.). Such disorders include disorders mediated by the snout ulcer virus, iridovirus, lymphocystis disease virus, infectious salmon anaemia, nodaviruses etc.

Compounds of the present invention may therefore be used in aquaculture. They may be used in food for aquatic organisms. Such food is within the scope of the present invention. It will generally be sold in sealed containers and labelled appropriately (e.g. as fish food, food for crustaceans, food for aquatic organisms, etc.). Alternatively, compounds of the present invention may be used for water treatment or for direct application to aquatic organisms. Such compounds do not therefore need to be present in foodstuffs in order to be useful in aquaculture.

EXAMPLES

General Preparation of —SR Derivatives from Cyclopentenone and Cyclohexenone Precursors Compounds in accordance with the invention can be prepared from the equivalent cyclohex-2-en-1-one or cyclopent-2-en-1-one derivative using the following general method (general method A).

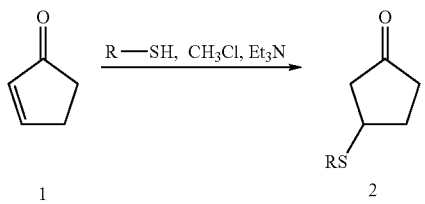

General Procedure: Add a catalytic amount of triethyl amine (20 µl) to a solution of the enone (1) (0.25 mM) and thiol (0.25-0.275 mM) in dry chloroform (5 ml), at room temperature, and stir the reaction mixture at room temperature for 1-3 days under a nitrogen atmosphere. The chloroform should then be removed under vacuum and residue purified by flash column chromatography over silica using ethyl acetate in hexane as eluent to afford the title compound 2. The enone 1 can be a cyclopent-2-en-1-one derivative, as illustrated, or a cyclohex-2-en-1-one. It can also carry one or more substituents that are retained in the final —SR substituted compound 2 in accordance with the invention.

Example 1

(a) Preparation of (R)-2-tert-Butoxycarbonylamino-3-[(1S,2S)-2-(tert-butyldimethylsilanyloxy)-4-oxo-cyclopentylsulfanyl]propionic acid methyl ester

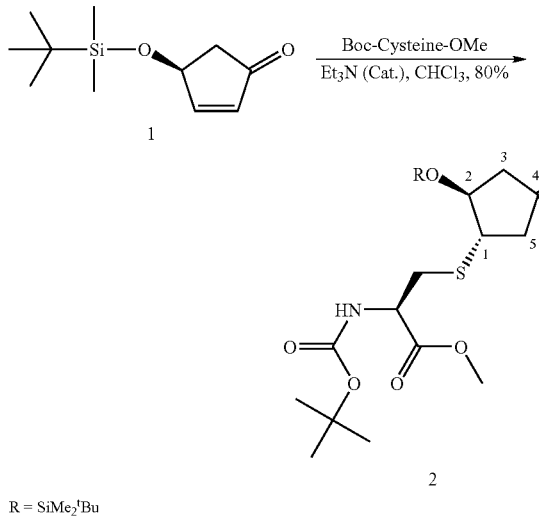

A solution of enone 1 (0.30 g, 1.41 mmol) in anhydrous chloroform (5 cm³) was added to a solution of Boc-cysteine (0.33 g, 1.41 mmol) and a catalytic amount of triethylamine (3 drops) in anhydrous chloroform (5 cm³). The reaction was stirred under $N_2$ for 16 hours until TLC analysis confirmed the disappearance of the enone. The solvent was removed under reduced pressure giving a pale yellow oil. Purification by flash column chromatography [$R_f$=0.25 (ethyl acetate-petroleum ether; 1:4)] gave the adduct 2 (0.50 g, 80% yield) as a colorless oil which solidified on standing at −2° C.; m.p. 52-53° C.; $v_{max}$ (film)/cm$^{-1}$ 3470, 3054, 2955, 2950, 2857, 1747, 1713; $[\alpha]_D^{22}$ −40.4 (c=0.52, MeOH); $\delta_H$ (400 MHz, CDCl$_3$) 0.09 (3H, s, CH$_3$), 0.12 (3H, s, CH$_3$), 0.88 (9H, s, CH$_3$), 1.45 (9H, s, CH$_3$), 2.14 (1H, dd, J 4.5 and 18.5 Hz, 5-CH$_A$H$_B$), 2.16 (1H, dd, J 2.5 and 18.0 Hz, 3-CH$_A$H$_B$), 2.68 (1H, dd, J 5.5 and 18.0 Hz, 3-CH$_A$H$_B$), 2.84 (1H, dd, J 7.5 and 18.5 Hz, 5-CH$_A$H$_B$), 2.99 (1H, dd, J 5.5 and 13.5 Hz, CH$_2$S), 3.13 (1H, dd, J 5.0 and 13.5 Hz, CH$_2$S), 3.30-3.36 (1H, m, 1-CHS), 3.77 (3H, s, CH$_3$), 4.23-4.27 (1H, m, 2-CHO), 4.56-4.61 (1H, m, CH), 5.34 (1H, d, J 7.5 Hz, NH); $\delta_C$ (100 MHz; CDCl$_3$); −4.40, −4.39, 18.0, 26.0, 28.7, 34.5, 43.9, 46.4, 48.9, 53.0, 53.4, 75.1, 80.6, 155.4, 178.4, 214.4; m/z (CI) 465 ([M+NH$_4$]$^+$, 5%), 448 ([M+H]$^+$, 5%), 136 (100). 155 (54), 230 (46), Found: [M+H]$^+$, 448.21794, C$_{20}$H$_{37}$SiSO$_6$N H requires [M+H]$^+$, 448.21893; Found C, 53.78; H, 8.33; N, 3.00%, C$_{20}$H$_{37}$NO$_6$SSi requires C, 53.66; H, 8.33; N, 3.13%. For the general method adapted see: V. van Axel Castelli, A. Dalla Cort, L. Mandolini, J. Am. Chem. Soc., 1998, 120, 12688-12689.

(b) Preparation of (R)-2-tert-Butoxycarbonylamino-3-[(1R,2R)-2-(tert butyldimethylsilanyloxy)-4-oxo-cyclopentylsulfanyl]propionic acid methyl ester

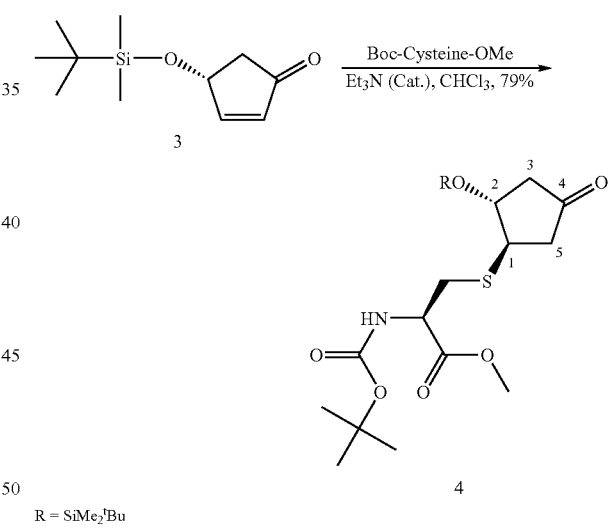

The compound was prepared using the general procedure described previously. Purification by flash column chromatography [$R_f$=0.2 (ethyl acetate-petroleum ether; 1:4)] gave 4 as a colorless oil (79% yield); $v_{max}$ (film)/cm$^{-1}$ 3367, 2953, 2929, 2856, 1750, 1715; $[\alpha]_D^{19}$ +18.5 (c=0.54, MeOH); $\delta_H$ (400 MHz, CDCl$_3$); 0.08 (3H, s, CH$_3$), 0.12 (3H, s, CH$_3$), 0.88, (9H, s, CH$_3$) 1.45 (9H, s, CH$_3$), 2.14 (1H, dd, J 2.5 and 18.5 Hz, 5-CH$_A$H$_B$), 2.16 (1H, dd, J 4.5 and 18.0 Hz, 3-CH$_A$H$_B$), 2.70 (1H, dd, J 5.5 and 18.5 Hz, 5-CH$_A$H$_B$), 2.77 (1H dd, J 7.5 and 18.0 Hz, 3-CH$_A$H$_B$), 3.05 (1H, dd, J 5.0 and 13.5 Hz, CH$_2$S), 3.09 (1H, dd, J 4.75 and 13.5 Hz, CH$_2$S), 3.34-3.39 (1H, m, 1-CHS), 3.78 (3H, s, OCH$_3$), 4.31-4.36 (1H, m, 2-CHO), 4.55-4.63 (1H, m, CH), 5.35 (1H, d, J 7.5 Hz, NH); $\delta_C$ (100 MHz; CDCl$_3$); −4.81, −4.79, 17.8, 25.6, 28.2, 33.9, 42.8, 45.0, 48.7, 52.6, 53.4, 74.6, 80.3, 155.0, 171.1, 214.1; m/z (CI) 465 ([M+NH$_4$]$^+$, 10%), 448 ([M+H]$^+$, 5%) 136 (100). 155 (35), 230 (54), Found: [M+H]$^+$, 448.21794, C$_{20}$H$_{37}$SiSO$_6$N H requires [M+H]$^+$, 448.21893.

(c) Preparation of (R)-2-tert-Butoxycarbonylamino-3-(3-oxocyclopentylsulfanyl)propionic acid methyl ester

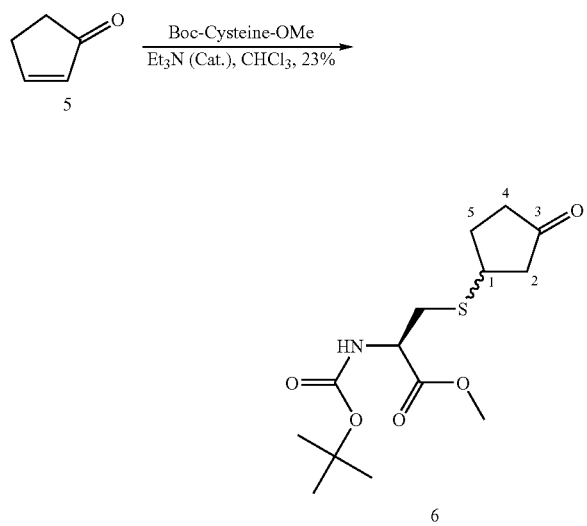

The compound was prepared using the general procedure described previously. Purification by flash column chromatography (ethyl acetate-petroleum ether; 1:2) gave 6 as a colorless waxy solid (23% yield) as a mixture of diastereomers. R$_f$=0.16 (ethyl acetate-petroleum ether; 1:2); v$_{max}$ (film)/cm$^{-1}$ 3355, 2976, 2940, 1745, 1713, 1506, 1368, 1161; δ$_H$ (400 MHz, CDCl$_3$); 1.45 (9H, s, CH$_3$), 1.89-2.00 (1H, m, CH$_2$, 2.14-2.24 (2H, m, CH$_2$), 2.32-2.49 (2H, m, CH$_2$), 2.58 (1H, dd, J 7.5 and 18.5 Hz, CH$_A$H$_B$), 2.93-3.13 (2H, m CH$_2$S), 3.47-3.55 (1H, m, 1-CHS), 3.77 (3H, s, OCH3), 4.55 (1H, m, CH), 5.36 (1H, s (br), NH); δ$_C$ (100 MHz; CDCl$_3$) 28.3, 29.8 and 29.9, 33.5 and 33.7, 36.9, 40.8, 45.0 and 45.6, 52.6, 80.2, 155.1, 171.3, 214.8; m/z (CI) 335 ([M+NH$_4$]$^+$, 25%), 318 ([M+H]$^+$, 9%), 277 (30%), 218 (70%); (Found: [M+H]$^+$, 318.13747, C$_{14}$H$_{23}$NO$_5$S H requires [M+H]$^+$, 317.13754; Found C, 52.39; H, 7.19; N, 4.22%, C$_{14}$H$_{23}$NO$_5$S requires C, 52.96; H, 7.30; N, 4.43%.

Example 2 (a)

(Z)-7-(2-Butyl-5-oxo-cyclopent-3-enyl)-hept-5-enoic acid (12) (cyclopentenone precursor to CTP-15a)

The acid 12 (see below) was prepared following the procedures outlined by C. B. Chapleo, S. M. Roberts and R. F. Newton in *J. Chem. Soc., Perkin Trans.* 1, 1980, 2088-2092.

Example 2 (b)

(Z)-7-(2-Butyl-5-oxo-cyclopent-3-enyl)-hept-5-enoic acid methyl ester 13 (cyclopentenone precursor to CTP-16a)

The methyl ester 13 was prepared by standard esterification conditions from the corresponding acid 12.

Example 3

Cyclopent-2-en-1-one precursors to compounds of group D can be prepared by the following general method:

2, n = 1
4, n = 3
6, n = 5
8, n = 8
10, n = 10

3, n = 1
5, n = 3
7, n = 5
9, n = 8
11, n = 10

Example 3(a)

Preparation of ((Z)-5-Pent-2-enyl)-cyclopent-2-enone (3) (precursor to CTC-73a)

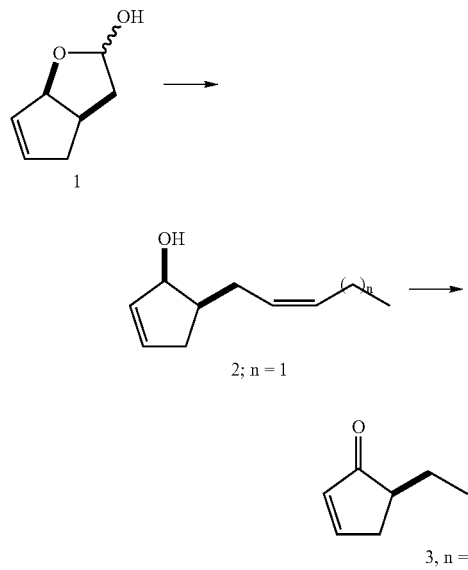

A solution of sodium bis(trimethylsilyl)amide in THF (2.40 ml, 1.0 mol dm$^{-3}$, 2.40 mmol) was added dropwise over 10 minutes to a stirred solution of propyltriphenylphosphonium bromide (1.16 g, 3.01 mmol) in THF (5 ml) at room temperature, under an atmosphere of nitrogen. The solution was stirred at room temperature for 30 minutes and a solution of the previously described lactol 1 (152 mg, 1.20 mmol) in THF (5 ml) was then added via cannula over 20 minutes. The mixture was then stirred at room temperature for 17 hours and ammonium chloride (sat'd. aq., 10 ml) was added slowly. The resulting mixture was then extracted with ethyl acetate (3×20 ml) and the combined extracts were dried over MgSO$_4$ and evaporated in vacuo. Flash chromatography (SiO$_2$, 30% diethyl ether in hexane) gave the alkene 2 (112 mg, 0.74 mmol, 61%) as a light yellow oil which was immediately taken on.

Dess-Martin periodinnane (440 mg, 1.04 mmol) was added in one portion to a stirred solution of the allylic alcohol 2 (105 mg, 0.69 mmol) in dichloromethane (14 ml) at 0° C., under an atmosphere of nitrogen. The mixture stirred at 0° C. for an hour, then evaporated in vacuo. Flash chromatography (SiO$_2$, 25% diethyl ether in petrol) gave the cyclopentenone 3 (88 mg, 0.59 mmol, 85%) as a pale yellow oil;

$\delta_H$ (400 MHz, CDCl$_3$) 7.68 (1H, dt J 5.7 & 2.8 Hz, CH=CHC=O), 6.19 (1H, dt J 5.7 & 2.1 Hz, CH=CHC=O), 5.51-5.42 (1H, m, CH=CH), 5.30-5.22 (1H, m, CH=CH), 2.82 (1H, ddt J 19.6, 6.9 & 2.5 Hz), 2.56-2.47 (1H, m), 2.42-2.32 (2H, m), 2.24-2.14 (1H, m), 2.11-1.94 (2H, m), 0.95 (3H, t J 7.6 Hz, CH$_2$CH$_3$); $\delta_C$ (100 MHz, CDCl$_3$) 211.9 (s), 163.7 (d), 134.0 (d), 133.9 (d), 125.0 (d), 44.6 (d), 34.9 (t), 28.4 (t), 20.6 (t), 14.2 (q).

Example 3(b)

Preparation of ((Z)-5-Hept-2-enyl)-cyclopent-2-enone (5) (precursor to CTC-74a)

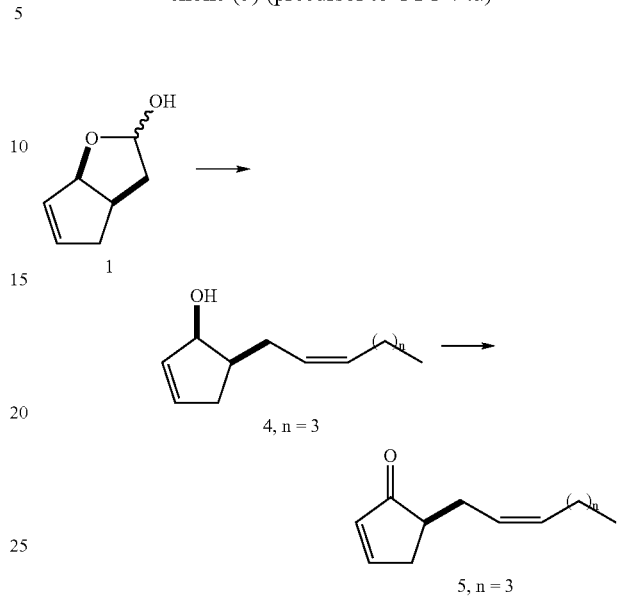

A solution of sodium bis(trimethylsilyl)amide in THF (2.20 ml, 2.0 mol dm$^{-3}$, 4.40 mmol) was added dropwise over 15 minutes to a stirred solution of pentyltriphenylphosphonium bromide (2.25 g, 5.44 mmol) in THF (10 ml) at room temperature, under an atmosphere of nitrogen. The solution was stirred at room temperature for 30 minutes and a solution of the previously described lactol 1 (275 mg, 2.18 mmol) in THF (10 ml) was then added via cannula over 15 minutes. The mixture was then stirred at room temperature for 64 hours and ammonium chloride (sat'd. aq., 20 ml) was added slowly. The resulting mixture was then extracted with ethyl acetate (4×20 ml) and the combined extracts were dried over MgSO$_4$ and evaporated in vacuo. Flash chromatography (SiO$_2$, 25% diethyl ether in hexane) gave the alkene 4 (245 mg, 1.36 mmol, 62%) as a yellow oil which was immediately taken on.

A solution of Dess-Martin periodinnane in dichloromethane (4.5 ml, 15% w/v, 1.59 mmol) was added in one portion to a stirred solution of the allylic alcohol 4 (240 mg, 1.33 mmol) in dichloromethane (20 ml) at 0° C., under an atmosphere of nitrogen. The mixture stirred at 0° C. for 45 minutes, then evaporated in vacuo. Flash chromatography (SiO$_2$, 20% diethyl ether in petrol) gave the cyclopentenone 5 (164 mg, 0.92 mmol, 69%) as a pale yellow oil;

$\delta_H$ (400 MHz, CDCl$_3$) 7.69 (1H, dt J 5.6 & 2.8 Hz, CH=CHC=O), 6.20 (1H, dt J 5.6 & 2.1 Hz, CH=CHC=O), 5.51-5.43 (1H, m, CH=CH), 5.34-5.25 (1H, m, CH=CH), 2.82 (1H, ddt J 19.5, 6.7 & 2.4 Hz), 2.58-2.49 (1H, m), 2.43-2.33 (2H, m), 2.24-2.16 (1H, m), 2.08-2.00 (2H, m), 1.35-1.29 (4H, m, CH$_2$CH$_2$CH$_3$), 0.92-0.87 (3H, m, CH$_2$CH$_3$); $\delta_C$ (100 MHz, CDCl$_3$) 211.9 (s), 163.7 (d), 133.9 (d), 132.4 (d), 125.5 (d), 44.6 (d), 34.9 (t), 31.8 (t), 28.5 (t), 27.0 (t), 22.3 (t), 13.9 (q).

Example 3(c)

Preparation of ((Z)-5-Non-2-enyl)-cyclopent-2-enone (7) (precursor to CTC-83a)

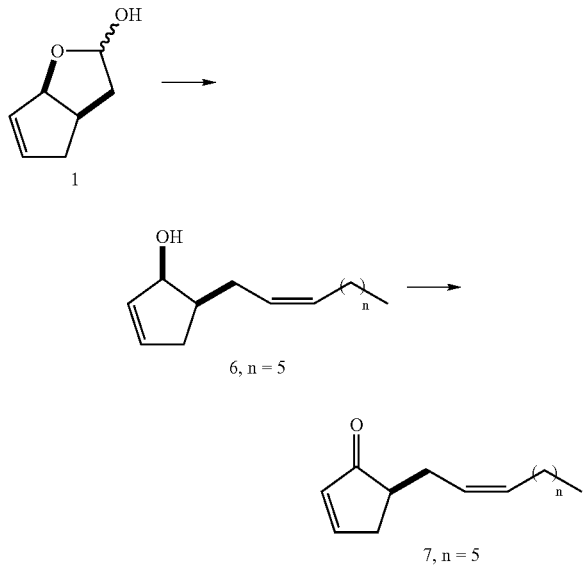

7, n = 5

A solution of sodium bis(trimethylsilyl)amide in THF (1.60 ml, 2.0 mol dm$^{-3}$, 3.20 mmol) was added dropwise over 12 minutes to a stirred solution of heptyltriphenylphosphonium bromide (1.75 g, 3.96 mmol) in THF (8 ml) at room temperature, under an atmosphere of nitrogen. The solution was stirred at room temperature for 45 minutes and a solution of the previously described lactol 1 (200 mg, 1.59 mmol) in THF (8 ml) was then added via cannula over 10 minutes. The mixture was then stirred at room temperature for 64 hours and ammonium chloride (sat'd. aq., 15 ml) was added slowly. The resulting mixture was then extracted with ethyl acetate (4×15 ml) and the combined extracts were dried over MgSO$_4$ and evaporated in vacuo. Flash chromatography (SiO$_2$, 20% diethyl ether in hexane) gave the alkene 6 (258 mg, 1.24 mmol, 78%) as a light orange oil which was immediately taken on.

A solution of Dess-Martin periodinnane in dichloromethane (4.2 ml, 15% w/v, 1.49 mmol) was added in one portion to a stirred solution of the allylic alcohol 6 (255 mg, 1.22 mmol) in dichloromethane (20 ml) at 0° C., under an atmosphere of nitrogen. The mixture stirred at 0° C. for 2 hours, then evaporated in vacuo. Flash chromatography (SiO$_2$, 15% diethyl ether in petrol) gave the cyclopentenone 7 (217 mg, 1.05 mmol, 86%) as a light yellow oil;

$\delta_H$ (400 MHz, CDCl$_3$) 7.68 (1H, dt J 5.7 & 2.8 Hz, CH=CHC=O), 6.19 (1H, dt J 5.7 & 2.0 Hz, CH=CHC=O), 5.52-5.43 (1H, m, CH=CH), 5.33-5.25 (1H, m, CH=CH), 2.82 (1H, ddt J 19.5, 6.8 & 2.4 Hz), 2.57-2.49 (1H, m), 2.42-2.33 (2H, m), 2.24-2.13 (1H, m), 2.07-2.00 (2H, m), 1.35-1.24 (8H, m, CH$_2$CH$_2$CH$_2$CH$_2$CH$_3$), 0.88 (3H, t J 6.9 Hz, CH$_2$CH$_3$); $\delta_C$ (100 MHz, CDCl$_3$) 211.8 (s), 163.5 (d), 133.9 (d), 132.5 (d), 125.6 (d), 44.7 (d), 35.0 (t), 31.7 (t), 29.6 (t), 29.0 (t), 28.5 (t), 27.3 (t), 22.6 (t), 14.0 (q).

Example 3(d)

Preparation of ((Z)-5-Dodec-2-enyl)-cyclopent-2-enone (9cis) (precursor to CTC-84a) and ((E)-5-Dodec-2-enyl)-cyclopent-2-enone (9trans) (precursor to CTC-85a)

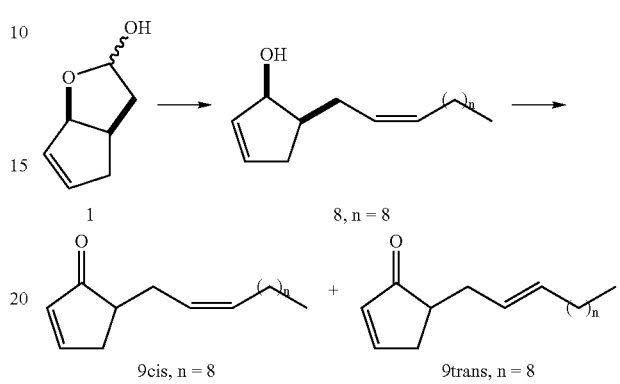

9cis, n = 8        9trans, n = 8

A solution of sodium bis(trimethylsilyl)amide in THF (1.60 ml, 2.0 mol dm$^{-3}$, 3.20 mmol) was added dropwise over 15 minutes to a stirred solution of decyltriphenylphosphonium bromide (1.92 g, 3.97 mmol) in THF (8 ml) at room temperature, under an atmosphere of nitrogen. The solution was stirred at room temperature for 45 minutes and a solution of the previously described lactol 1 (200 mg, 1.59 mmol) in THF (8 ml) was then added via cannula over 10 minutes. The mixture was then stirred at room temperature for 68 hours and ammonium chloride (sat'd. aq., 15 ml) was added slowly. The resulting mixture was then extracted with ethyl acetate (4×15 ml) and the combined extracts were dried over MgSO$_4$ and evaporated in vacuo. Flash chromatography (SiO$_2$, 20% diethyl ether in hexane) gave the alkene 8 (301 mg, 1.20 mmol, 76%) as a light yellow oil which was immediately taken on.

A solution of Dess-Martin periodinnane in dichloromethane (4.1 ml, 15% w/v, 1.45 mmol) was added in one portion to a stirred solution of the allylic alcohol 8 (300 mg, 1.20 mmol) in dichloromethane (20 ml) at 0° C., under an atmosphere of nitrogen. The mixture stirred at 0° C. for 2 hours, then evaporated in vacuo. Flash chromatography (SiO$_2$, 15% diethyl ether in petrol) gave the major (Z)-cyclopentenone 9cis (184 mg, 0.74 mmol, 62%) as a light yellow oil; $\delta_H$ (400 MHz, CDCl$_3$) 7.68 (1H, dt J 5.6 & 2.7 Hz, CH=CHC=O), 6.19 (1H, dt J 5.6 & 2.0 Hz, CH=CHC=O), 5.51-5.43 (1H, m, CH=CH), 5.33-5.25 (1H, m, CH=CH), 2.82 (1H, ddt J 19.6, 6.8 & 4.7 Hz), 2.57-2.49 (1H, m), 2.42-2.33 (2H, m), 2.23-2.14 (1H, m), 2.04 (2H, app. q J 6.7 Hz), 1.32-1.25 (14H, m, CH$_2$CH$_2$CH$_2$CH$_2$CH$_2$CH$_2$CH$_2$CH$_3$), 0.89 (3H, t J 6.8 Hz, CH$_2$CH$_3$); $\delta_C$ (100 MHz, CDCl$_3$) 211.8 (s), 163.5 (d), 133.9 (d), 132.5 (d), 125.6 (d), 44.7 (d), 35.0 (t), 31.9 (t), 29.63 (t), 29.57 (t), 29.53 (t), 29.3 (t), 28.5 (t), 27.3 (t), 22.7 (t), 14.1 (q);

and the minor (E)-cyclopentenone 9trans (32 mg, 0.13 mmol, 11%) as a colourless oil;

$\delta_H$ (400 MHz, CDCl$_3$) 7.63 (1H, dd J 5.6 & 2.5 Hz, CH=CHC=O), 6.17 (1H, dd J 5.6 & 1.9 Hz, CH=CHC=O), 5.56-5.45 (1H, m, CH=CH), 5.39-5.31 (1H, m, CH=CH), 3.04-2.97 (1H, m), 2.52 (1H, dd J 18.8 & 6.4 Hz), 2.35-2.15 (2H, m), 2.07-1.98 (3H, m), 1.32-1.24 (14H, m, CH$_2$CH$_2$CH$_2$CH$_2$CH$_2$CH$_2$CH$_2$CH$_3$), 0.89 (3H, t J 6.8 Hz, CH$_2$CH$_3$); δ$_C$ (100 MHz, CDCl$_3$) 209.7 (s), 167.9 (d), 134.1 (d), 132.9 (d), 125.4 (d), 41.5 (d), 40.5 (t), 32.0 (t), 31.9 (t), 29.55 (t), 29.49 (t), 29.3 (t), 27.4 (t), 22.6 (t), 14.0 (q).

Example 4(a)

Synthesis of 4-tert-butyldimethylsilyloxy-cyclohex-2-en-1-one (precursor to CTM-22a)

The subject compound was synthesised following the procedure described in *J. Amer. Chem. Soc.*; (1989); 111; 7; 2599-2604; Danishefsky, Samuel J.; Simoneau, Bruno and *Tetrahedron Lett.*; (1996); 37; 27; 4679-4682; Pour, Milan; Negishi, Ei-ichi.

The reaction scheme used was as follows:—

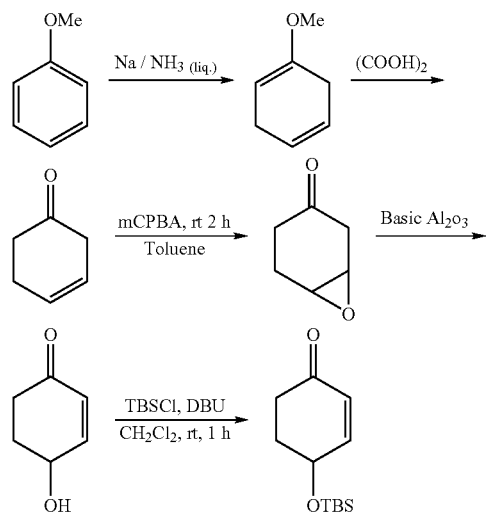

Example 4(b)

Synthesis of the 5-tert-butyldimethylsilyloxy-cyclohex-2-en-1-one (precursor to CTM 25a)

Synthetic Pathway:

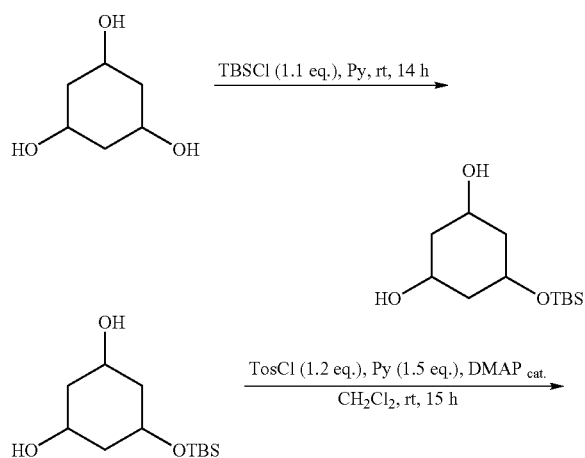

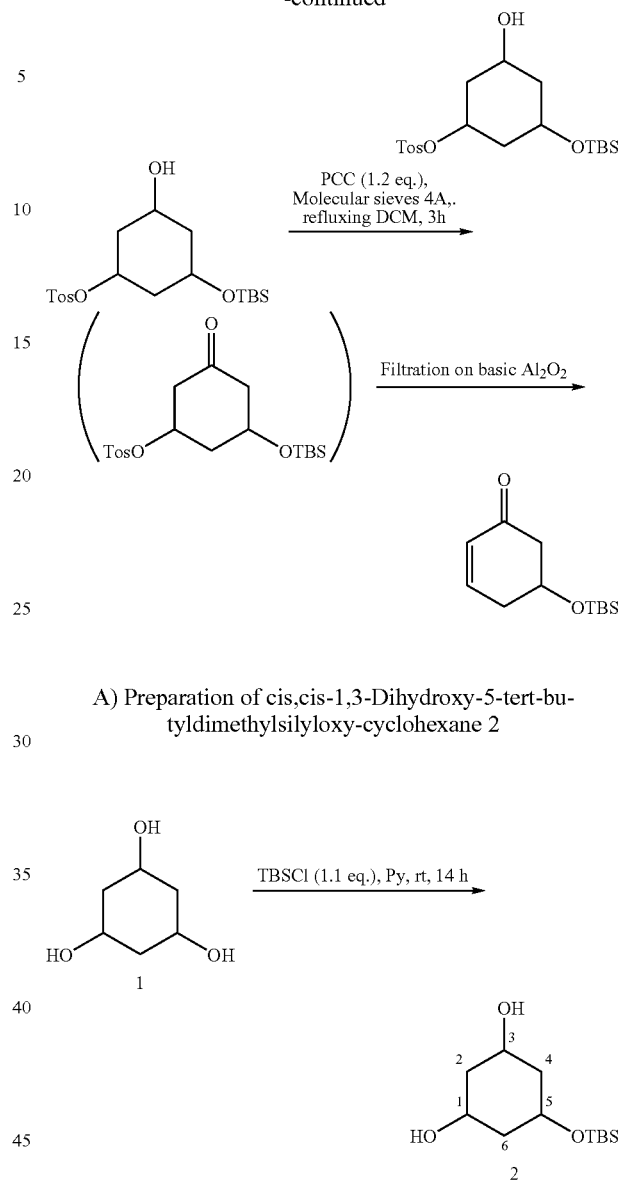

A) Preparation of cis,cis-1,3-Dihydroxy-5-tert-butyldimethylsilyloxy-cyclohexane 2

Commercially available cis,cis-1,3,5-trihydroxycyclohexane dihydrate (Aldrich:3.02 g, 18.0 mmol) was dissolved in 150 mL of a mixture of anhydrous ethanol and toluene (1/1). The 2 molecules of water initially present in the starting material were removed through an azeotropic evaporation of the solvent on a rotary evaporator. This operation was repeated a second time with 34 mL of pyridine (freshly distilled and kept over KOH) as a solvent. The resulting white powder 1 was then dissolved in 45 mL of pyridine and treated with 15 mL of pre-activated molecular sieves 4A for 30 min.

The resulting anhydrous solution was then transferred with a syringe to a reaction flask; the molecular sieves were washed twice with a total amount of 30 mL of pyridine, which was combined with the first 45 mL in the reaction flask. A solution of tert-butyldimethylchorosilane (3.01 g, 19.8 mol, 1.1 eq.) in 10 mL of anhydrous THF was then added to the flask, and the reaction mixture was stirred under argon at room temperature for 14 h. The reaction was then quenched by the addition of 1 mL of water, the pyridine was removed on a rotary evaporator (below 45° C.) and the residue was dissolved in a mixture of ethyl acetate and water. The aqueous phase was extracted with EtOAc (3*30 mL), and the combined organic phases were washed with a saturated solution of NH$_4$Cl. The organic solution was then dried over MgSO$_4$, filtered and evaporated to yield 5.14 g of a colourless oil. The compound was then purified by CC (diethyl ether first, then EtOAc), to yield 2.17 g of the desired product (8.8 mmol, yield=49%) as a white solid, along with 1.6 g of disilylated compound.

$^1$H-NMR (CDCl$_3$, 250 MHz): δ=3.84 (3H, m, CH—O); 2.06 (3H, m); 1.68-1.45 (5H, m); 0.89 (9H, s, —OSiMe$_2^t$Bu); 0.08 (6H, s, —OSiMe$_2^t$Bu).

$^{13}$C-NMR (CDCl$_3$, 400 MHz): δ=67.16, C(5); 66.29, C(1)+C(3); 42.84, C(4)+C(6); 42.67, C(2); 31.50, C(—OSiMe$_2$C(CH$_3$)$_3$); 25.80, C(—OSiMe$_2$C(CH$_3$)$_3$); −4.79, —OSiMe$_2^t$Bu).

HR-MS measured by Chemical Ionisation on [M+H$^+$]: C$_{12}$H$_{27}$SiO$_3$
Theory: 247.17294
Found: 247.17337

B) Preparation of cis,cis-1-hydroxy-3-paratoluenesulfonate-5-tert-butyldimethylsilyloxy-cyclohexane 3

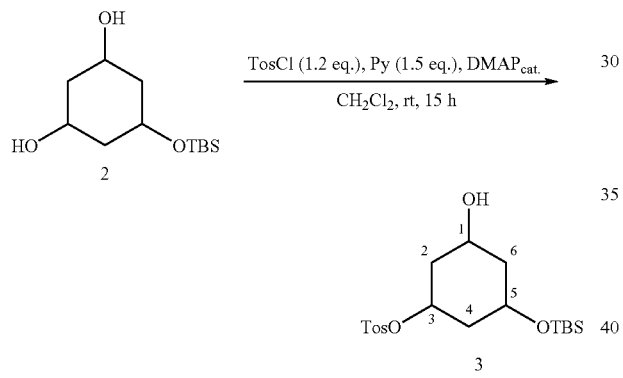

0.6 mL of dry pyridine (7.5 mmol, 1.5 eq.) and 20 mg of 4-N,N-dimethyl-pyridine (cat.) were added to a solution of cis,cis-1,3-dihydroxy-5-tert-butyldimethylsilyloxy-cyclohexane (2) (1.23 g, 5.0 mmol) in 10 mL of anhydrous CH$_2$Cl$_2$. para-Toluene-sulfonyl chloride (1.14 g, 6.0 mmol, 1.2 eq.) was added and the mixture was allowed to react at room temperature for 15 h under argon. At the end of this period, TLC analysis of an extracted aliquot showed no unreacted starting material 2 remaining (TLC: Et$_2$O/Hexane (1/1)). The reaction was then quenched by the addition of 20 mL of water, and the aqueous phase was extracted with diethyl ether (3×20 mL). The combined organic phases were washed with 30 mL of a saturated solution of NH$_4$Cl, dried over MgSO$_4$, filtered and evaporated to yield an orange oil. The compound was then purified by column chromatogrphy (Et$_2$O/Hexane (1/1): R$_f$=0.35), to yield 1.32 g of the desired product 3 (3.3 mmol, yield=66) as a white wax.

$^1$H-NMR (CDCl$_3$, 250 MHz): δ=7.79 (2H, d, J=8.2 Hz, Tos); 7.34 (2H, d, J=8.2 Hz, Tos); 4.43 (1H, m, CH-OTos); 3.59 (2H, m, CH—OH+CH-OTBS); 2.44 (3H, s, Tos); 2.21-1.93 (3H, m); 1.58-1.25 (4H, m); 0.84 (9H, s, —OSiMe$_2^t$Bu); 0.01 & −0.01 (2*3H, s, —OSiMe$_2^t$Bu).

$^{13}$C-NMR (CDCl$_3$, 400 MHz): δ=144.74, —OSO$_2$—C$_{tolyl}$; 134.51, C$_{tolyl}$—CH$_3$; 129.86 & 127.71, CH$_{tosyl}$; 75.81, C(3); 65.80, C(1); 65.28, C(5); 43.53, C(6); 40.93, C(2); 40.60, C(4); 30.90, C(—OSiMe$_2$C(CH$_3$)$_3$); 25.72, C(—OSiMe$_2$C(CH$_3$)$_3$); 21.63, Me$_{tosyl}$; 4.81, —OSiMe$_2^t$Bu).

HR-MS: Chemical ionisation (NH$_3$); [M+H$^+$: C$_{19}$H$_{33}$SiSO$_5$]: theory: 401.18182
found: 401.18110
Microanalysis: theory: C, 56.97; H, 8.05;
found: C, 56.68; H, 8.04.

C) Preparation of 5-tert-butyldimethylsilyloxy-cyclohex-2-en-1-one 4

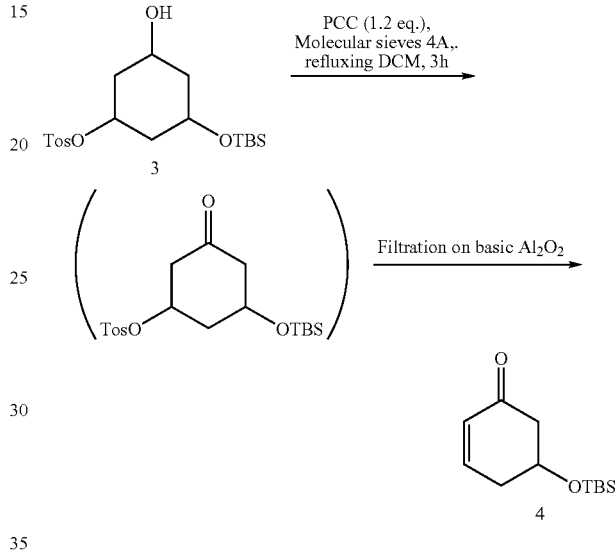

Pyridinium chlorochromate PCC (0.79 g, 3.68 mmol, 1.2 eq.) was added to a solution of cis,cis-1-hydroxy-3-paratoluenesulfonate-5-tert-butyldimethyl-silyloxy-cyclohexane (3) (1.23 g, 3.07 mmol) in 20 mL of dry CH$_2$Cl$_2$ at room temperature under argon. The suspension was then heated to reflux for 3 h. At the end of this period, TLC analysis of an extracted aliquot showed no unreacted starting material 3 remaining and two new compounds to have been formed; an oxidation product R$_f$=0.1) and the subject compound 4 itself (R$_f$=0.33) (TLC: Et$_2$O/Hexane (1/3)). After the reaction had been cooled down to room temperature, the suspension was filtered through a 5 cm high basic aluminium oxide pad (column), with diethyl ether as an eluent. The filtrate, containing compound 4, was then evaporated to yield 580 mg of a colourless oil. The compound was then further purified by column chromatography (Et$_2$O/Hexane (1/3): R$_f$=0.33), to yield 556 mg of 4 (2.45 mmol, yield=80%) as colourless oil, which crystallizes in the freezer into a white solid (Mp<0° C.).

$^1$H-NMR (CDCl$_3$, 250 MHz): δ=6.88 (1H, ddd, J(2,3)=12.7, J(3,4)+J(3,4')=6.5 & 4.5 Hz, H—C(3)); 6.06 (1H, dt, J(2,4)=J(2,4')=2.4 Hz, H—C(2)); 4.24 (1H, ddt, J(5,6)=11.4, J(4,5)=9.3 & J(5,6')=J(5,4')=5.5 Hz, H—C(5)); 2.67 & 2.48 (2H, System ABX, J$_{gem}$=19.2, H+H'—C(6)); 2.60 & 2.38 (2H, System ABX$_2$Y, H+H'—C(4)); 0.89 (9H, s, —OSiMe$_2^t$Bu); 0.07 (6H, s, —OSiMe$_2^t$Bu).

$^{13}$C-NMR (CDCl$_3$, 400 MHz): δ=147.13, C(3); 130.52, C(2); 67.99, C(5); 48.44, C(6); 35.96, C(4); 26.07, C(—OSiMe$_2$C(CH$_3$)$_3$); −4.38 & −4.46, —OSiMe$_2^t$Bu).

HR-MS: Chemical ionisation (NH$_3$); [M+H$^+$: C$_{12}$H$_{23}$SiO$_2$]: theory: 227.14673
found: 227.14672

Example 5

Preparation of CTC-109

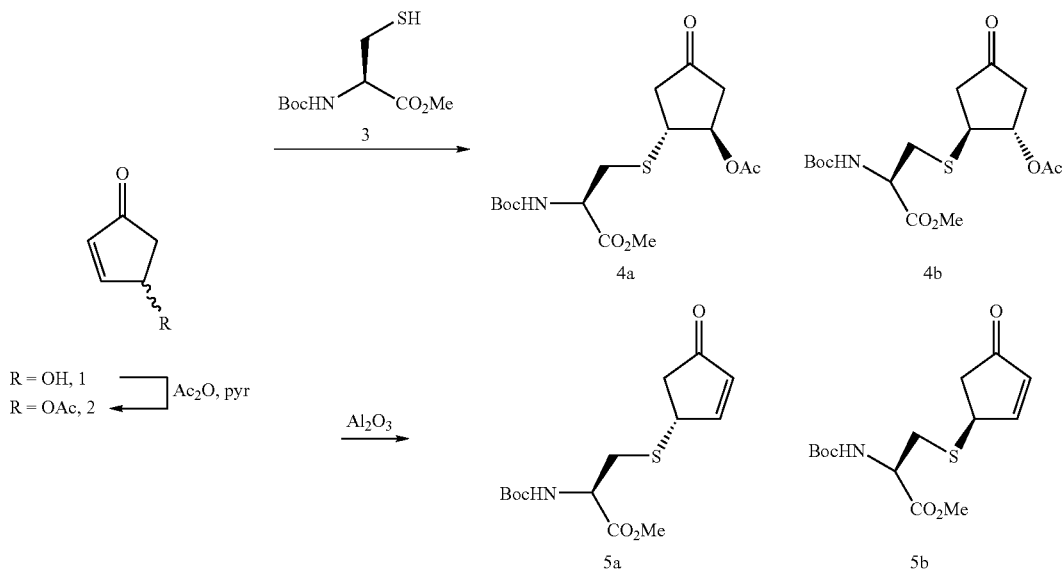

A mixture of 2 (94 mg, 0.67 mmol, 1 eq.) and 3 (158 mg, 0.67 mmol, 1 eq.) in DMSO (2 cm³) were stirred for 15 h at room temperature. DCM (15 cm³) and H₂O (15 cm³) were added and the resultant aqueous layer was further extracted with DCM (3×15 cm³). The combined organic extracts were dried over MgSO₄. Filtration and solvent removal under reduced pressure gave the conjugate adducts 4a and 4b.

The crude adducts 4 (ca. 0.67 mmol) were dissolved in CDCl₃ (4 cm³) and treated with basic Al₂O₃ (600 mg) at room temperature. Stirring was continued for 2 days. Purification by flash column chromatography (Hex-Et₂O; 1:1→Hex-Et₂O; 1:2) gave an inseparable mixture of the unassigned diastereomers of CTC-109 (168 mg, 80%), 5a and 5b, in roughly equal amounts (as judged by $^1$H-NMR spectroscopy) as a viscous clear oil. $R_f$=0.3 (Hex-Et₂O; 1:2); $\delta_H$ (400 MHz, CDCl₃) 1.45*# (9H, s, CH₃), 2.30* (1H, dd, J 2.0, 19.25 Hz, CH₂), 2.34# (1H, dd, J 2.0, 19.25 Hz, CH₂), 2.85# (1H, dd, J 6.5, 19.25 Hz, CH₂), 2.86* (H, dd, J 6.5, 19.25 Hz, CH₂), 2.92-3.13*# (2H, m, CH₂S), 3.79*# (3H, s(br), CH₃), 4.15-4.28*# (1H, m, CHS), 4.52-4.75*# (1H, m, CH), 5.34-5.40*# (1H, m, NH), 6.45*# (1H, d (br), J 5.5 Hz, CH), 7.55-7.60*# (1H, m, CH); $\delta_C$ (100 MHz, CDCl₃) 28.2*#, 32.9#, 33.2*, 42.6#, 42.7*, 43.6#, 43.7#, 52.7*#, 53.2*, 53.4#, 80.41*#, 134.7#, 134.8*, 155.0*#, 162.8*, 162.9#, 171.0*#, 206.9*#; m/z (CI) 333 (MNH₄⁺, 50%), 316 (MH⁺, 5%), 277 (40%), 216 (100%). *Denotes one diastereomer, #denotes other diastereomer. Exp. pe1/57.

Example 6

Preparation of (R)-2-tert-Butoxycarbonylamino-3-[(1S,2S)-2-(tert-butyl-dimethyl-silanyloxy)-5-oxo-cyclohexylsulfanyl]-propionic acid methyl ester (CTM-68, an example of CTM 22a)

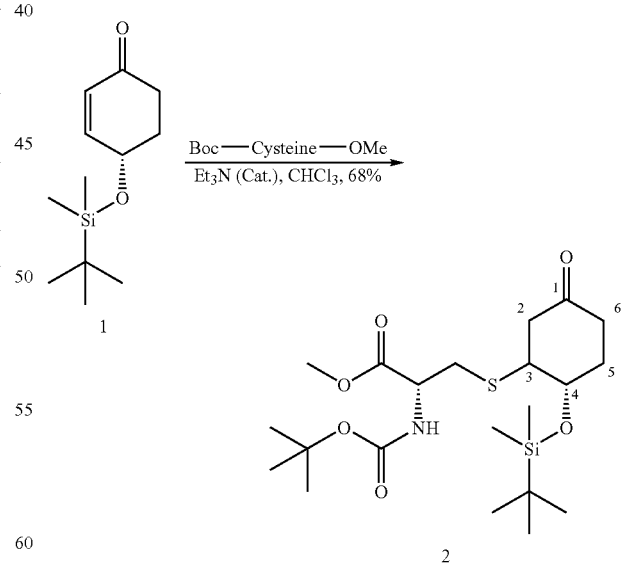

A solution of Boc-cysteine (60 mg, 0.25 mmol) with a catalytic amount of triethylamine (3 drops) in anhydrous chloroform (1.4 cm³) was added to a solution of enone 1 (56 mg, 0.25 mmol) in anhydrous chloroform (1 cm³). The reaction was stirred under Argon for 16 hours. TLC analysis confirmed the disappearance of the enone. The solvent was removed under reduced pressure giving a colourless oil.

Purification by flash column chromatography [$R_f$=0.30 (diethyl ether/hexane; 1:1)] gave the adduct 2 (78 mg, 68% yield) as a colourless oil which solidified on standing at r.t.; the cysteine adduct is then recrystallised from (diethyl ether/hexane; 1/3); m.p. 91-93° C.; $[\alpha]_D^{20}$+62 (c=1.0, CHCl$_3$); $\delta_H$ (250 MHz, CDCl$_3$) 0.12 (6H, br. s, —Si$^t$Bu(C$\underline{H}_3$)$_2$), 0.91 (9H, s, —SiMe$_2$C(C$\underline{H}_3$)$_3$), 1.44 (9H, s, —OC(C$\underline{H}_3$)$_3$), 1.80-1.90 (1H, m, AB-C(5)), 2.12-2.30 (2H, m, AB-C(5)+AB-C(6)), 2.37 (1H, dd, J 15.0 and 3.0 Hz, AB-C(2)), 2.52-2.68 (1H, m, AB-C(6)), 2.98 & 3.00 (2H, br. AB, —C$\underline{H}_2$S—), 3.05 (1H, dd, J 5.0 and 15.0 Hz, AB-C(2)), 3.17 (1H, m, H—C(3)), 3.74 (3H, s, —OC$\underline{H}_3$), 4.02 (1H, m, H—C(4)), 4.51-4.60 (1H, m, C$\underline{H}$(Cys)), 5.36 (1H, d, J 8.0 Hz, N$\underline{H}$).

Example 7

Preparation of Precursors to Compounds of Group A in Accordance with the Invention General Scheme:

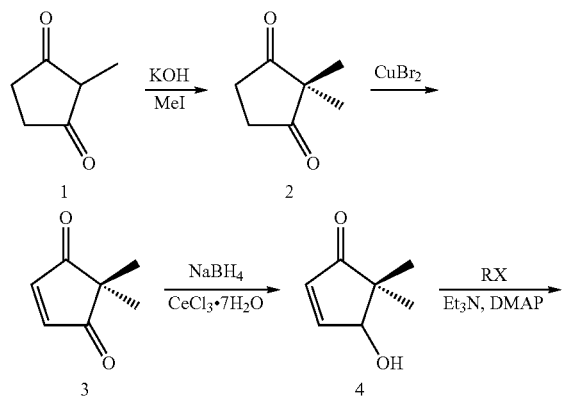

(a) Preparation of 2,2-dimethylcyclopentane-1,3-dione 2

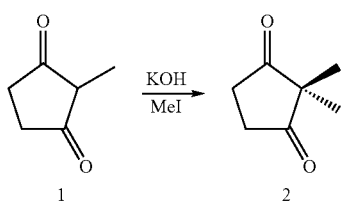

A solution of potassium hydroxide (15.0 g, 0.27 mol) in water (40 ml) was added to a stirred solution of 2-methylcyclopentane-1,3-dione 1 (25.0 g, 0.22 mol) in 1,4-dioxane (120 ml) at room temperature. Methyl iodide (100 g, 0.70 mol) was then added and the resulting solution was heated under reflux for 15 hours. The mixture was then cooled to room temperature and extracted with ethyl acetate (4×160 ml). The combined extracts were then dried over MgSO$_4$ and evaporated in vacuo. Flash chromatography (SiO$_2$, 60% diethyl ether in hexane) gave the dione 2 (18.0 g, 0.14 mol, 64%) as a white solid; $\delta_H$ (300 MHz, CDCl$_3$) 2.80 (4H, s, CH$_2$CH$_2$), 1.16 (3H, s, CH$_3$), 1.15 (3H, s, CH$_3$); $\delta_C$ (75.5 MHz, CDCl$_3$) 216.3 (s), 52.6 (s), 34.5 (t), 20.2 (q).

(b) Preparation of 2,2-dimethylcyclopent-4-ene-1,3-dione 3

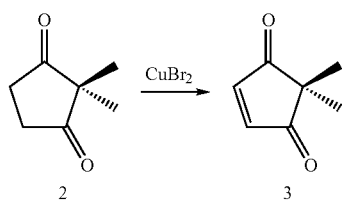

Copper (II) bromide (63.4 g, 0.28 mol) was added to a stirred solution of the dione 2 (17.9 g, 0.14 mol) in methanol (280 ml) at room temperature, under an atmosphere of nitrogen. The reaction was heated under reflux for 90 minutes and then cooled to room temperature. The mixture was then filtered through celite, washing with dichloromethane (3×250 ml) and evaporated in vacuo. Flash chromatography (SiO$_2$, 50% diethyl ether in hexane) gave the enedione 3 (11.3 g, 91.0 mmol, 64%) as a yellow oil; $\delta_H$ (300 MHz, CDCl$_3$) 7.22 (2H, s, CH=CH), 1.17 (3H, s, CH$_3$), 1.15 (3H, s, CH$_3$); $\delta_C$ (75.5 MHz, CDCl$_3$) 207.7 (s), 147.1 (d), 46.4 (s), 19.5 (q).

(c) Preparation of 4-hydroxy-5,5-dimethylcyclopent-2-enone 4

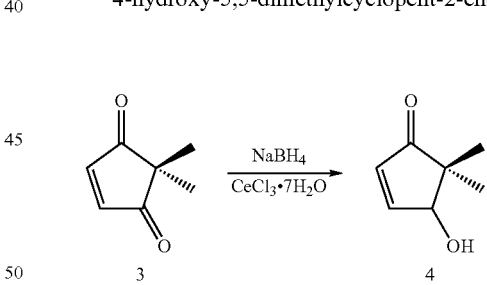

Cerium (III) chloride heptahydrate (16.5 g, 44.3 mmol) was added to a stirred solution of the enedione 3 (5.00 g, 40.3 mmol) in methanol (150 ml) at room temperature, under an atmosphere of nitrogen. The resulting mixture was then cooled to −78° C. and sodium borohydride (1.68 g, 44.4 mmol) was added in portions over 30 minutes. The mixture was stirred at −78° C. for a further 2 hours, then at −30° C. for 45 minutes. Ammonium chloride (sat'd. aq., 150 ml) was then added and the mixture was extracted with ethyl acetate (3×150 ml). The combined organic extracts were then dried over MgSO$_4$, and evaporated in vacuao. Flash chromatography (SiO$_2$, 80% diethyl ether in hexane) gave the hydroxyketone 4 (3.58 g, 28.4 mmol, 71%) as a white solid; $\delta_H$ (300 MHz, CDCl$_3$) 7.46 (1H, dd J 5.9 & 2.2 Hz, CH=CHC=O), 6.20 (1H, dd J 5.9 & 1.4 Hz, CH═CHC═O), 4.59-4.57 (1H, m, CHOH), 1.16 (3H, s, CH$_3$), 1.07 (3H, s, CH$_3$); δ$_C$ (75.5 MHz, CDCl$_3$) 211.7 (s), 160.6 (d), 132.7 (d), 79.8 (d), 48.2 (s), 22.7 (q), 20.0 (q).

(d) Preparation of enone 5

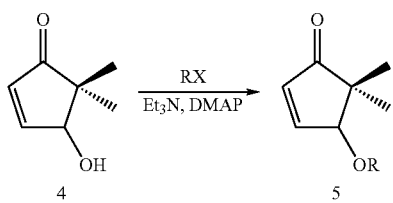

A stock solution of the hydroxy enone 4 (550 mg, 4.4 mmol) in anhydrous dichloromethane (33 cm$^3$) was split between eleven reaction wells of a parallel synthesiser. To each well was added triethylamine (67 μl, 0.48 mmol) and a catalytic amount 4-dimethylaminopyridine followed by the appropriate alkylating agent (0.48 mmol), the reactions were left stirring under an atmosphere of nitrogen for 45 h. Water (3 cm$^3$) was added to each well and the mixtures passed through a phase separator. The aqueous phase was then washed with dichloromethane (5 cm$^3$) and the organic solvent removed from each product in vacuo. The products were purified by flash column chromatography (SiO$_2$) to isolate the desired products.

(e) Preparation of acetic acid 5,5-dimethyl-4-oxocyclopent-2-enyl ester 5a (CTC-103)

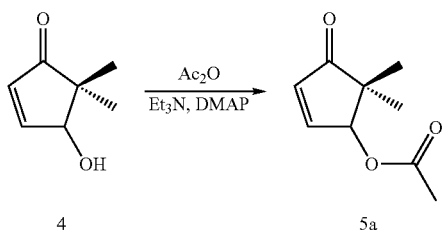

Triethylamine (67 μl, 0.48 mmol), 4-dimethylaminopyridine (15 mg, 0.12 mmol) and acetic anhydride (45 μl, 0.48 mmol) were added to a solution of the 4-hydroxy ketone 4 (50 mg, 0.40 mmol) in dichloromethane (3 cm$^3$) at room temperature, under an atmosphere of nitrogen. The solution was stirred at room temperature for 48 hours and then water (3 cm$^3$) added. The resulting mixture was then extracted with dichloromethane (2×3 cm$^3$) and the combined organic extracts evaporated in vacuo. Flash chromatography (SiO$_2$, dichloromethane) gave the acetate 5a (62 mg, 93%) as a pale yellow oil; δ$_H$ (400 MHz, CDCl$_3$) 1.02 (3H, s, CH$_3$), 1.22 (3H, s, CH$_3$), 2.13 (3H, s, CH$_3$), 5.57-5.58 (1H, m, CHOAc), 6.28 (1H, dd, J 1.3 and 5.9, CH═CHC═O), 7.40 (1H, dd, J 2.4 and 5.9, CH═CHC═O); δ$_C$ (100 MHz, CDCl$_3$) 19.9, 20.7, 23.4 (CH$_3$), 47.1 (C), 80.5, 134.3, 156.9 (CH), 170.5, 210.5 (C); ν$_{max}$ (film)/cm$^{-1}$ 1235, 1374, 1466, 1599, 1720, 1736, 2976; m/z (EI) 168 (M$^+$, 3%); Found 168.07920 Calculated for C$_9$H$_{12}$O$_3$ 168.07864.

(f) Preparation of 2,2-dimethyl-propionic acid 5,5-dimethyl-4-oxocyclopent-2-enyl ester 5b (CTC-102)

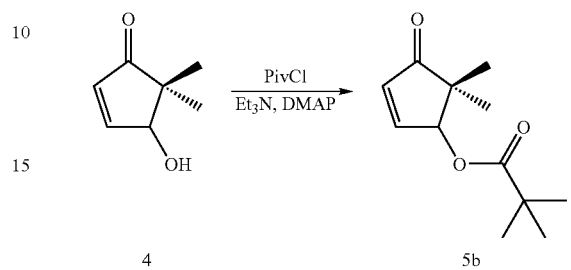

Triethylamine (67 μl, 0.48 mmol), 4-dimethylaminopyridine (15 mg, 0.12 mmol) and pivoyl chloride (59 μl, 0.48 mmol) were added to a solution of the 4-hydroxy ketone 4 (50 mg, 0.40 mmol) in dichloromethane (3 cm$^3$) at room temperature, under an atmosphere of nitrogen. The solution was stirred at room temperature for 48 hours and then water (3 cm$^3$) added. The resulting mixture was then extracted with dichloromethane (2×3 cm$^3$) and the combined organic extracts evaporated in vacuo. Flash chromatography (SiO$_2$, dichloromethane) gave the pivolate 5b (77 mg, 92%) as a pale yellow oil; δ$_H$ (400 MHz, CDCl$_3$) 1.02 (3H, s, CH$_3$), 1.23 (3H, s, CH$_3$), 1.24 (9H, s, $^t$Bu), 5.54-5.55 (1H, m, CHOPiv), 6.30 (1H, dd, J 1.3 and 5.8, CH═CHC═O), 7.41 (1H, dd, J 2.3 and 5.8, CH═CHC═O); δ$_C$ (100 MHz, CDCl$_3$) 20.3, 23.8, 27.5 (CH$_3$), 39.4, 47.6 (C), 80.6, 134.6, 157.6 (CH), 178.4, 211.3 (C); ν$_{max}$ (film)/cm$^{-1}$ 1085, 1150, 1280, 1385, 1466, 1599, 1723, 2975; m/z (EI) 210 (M$^+$, 0.47%); Found 210.12584 Calculated for C$_{12}$H$_{18}$O$_3$ 210.12560.

(g) Preparation of (4S)-4-hydroxy-5,5-dimethylcyclopent-2-enone (S)-4 and (4R)-4-hydroxy-5,5-dimethylcyclopent-2-enone (R)-4

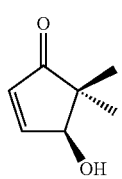

(S)-4

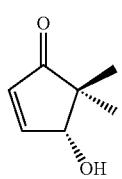

(R)-4

The chiral alcohols (S)-4 and (R)-4 were prepared using the methods described in the following reference utilising an enzymatic resolution protocol: H. Miyaoka, S. Sagawa, H. Nagaoka and Y. Yamada, *Tetrehedron Asymm.*, 1995, 6, 587-594.

(h) Preparation of 2,2-dimethyl-propionic acid (1S)-5,5-dimethyl-4-oxocyclopent-2-enyl ester (S)-5b (CTC-179)

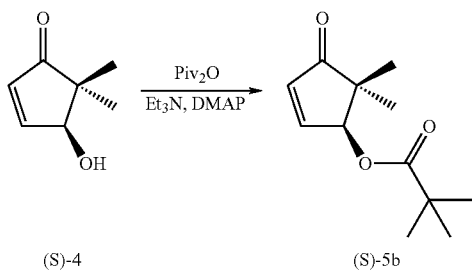

Triethylamine (0.14 ml, 1.00 mmol), 4-dimethylaminopyridine (15 mg, 0.12 mmol) and pivoyl anhydride (0.10 ml, 0.49 mmol) were added to a solution of the 4-hydroxy ketone (S)-4 (50 mg, 0.40 mmol) in dichloromethane (4 ml) at room temperature, under an atmosphere of nitrogen. The solution was stirred at room temperature for 48 hours, then evaporated in vacuo. Flash chromatography ($SiO_2$, dichloromethane) gave the pivolate (S)-5b (79 mg, 0.38 mmol, 95%) as a colourless oil; which was shown to be identical by nmr to the racemic material.

(i) Preparation of (R)-2,2-dimethyl-propionic acid 5,5-dimethyl-4-oxocyclopent-2-enyl ester (R)-5b (CTC-166)

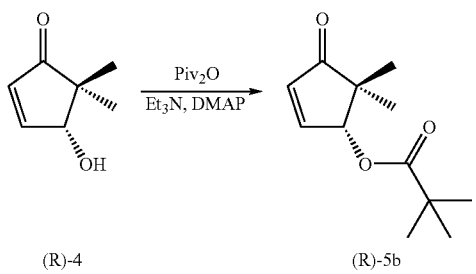

The pivolate (R)-5b was prepared as a colourless oil, in an analogous manner to the preparation of its epimer (S)-5b; which was also shown to be identical by nmr to the racemic material.

Example 8

Preparation of Compounds of Group A from the Precursors Prepared in Example 7

(a) Preparation of 2,2-dimethylpropionic acid (1S, 5R)-2,2-dimethyl-5-(naphthalen-2-ylsulfanyl)-3-oxocyclopentyl ester anti-6a (CTM-193) & 2,2-dimethylpropionic acid (1S,5S)-2,2-dimethyl-5-(naphthalen-2-ylsulfanyl)-3-oxocyclopentyl ester syn-6a

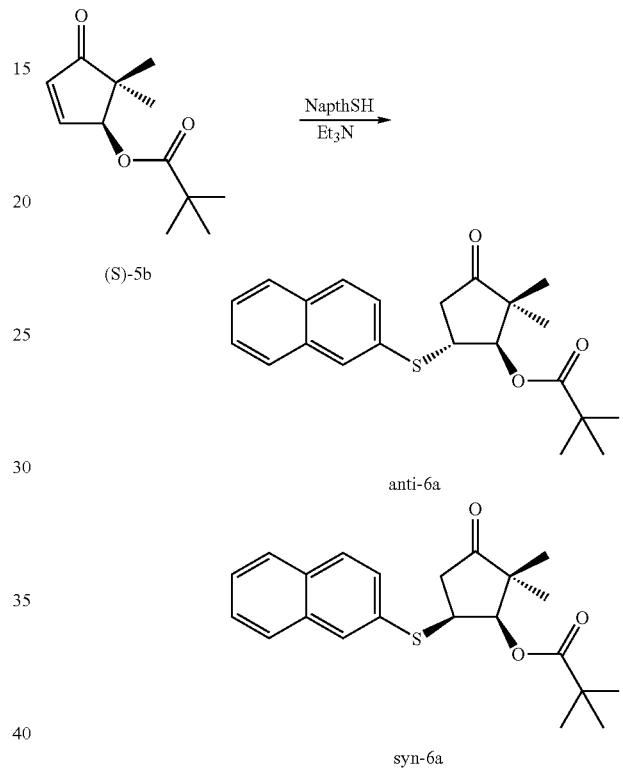

To a solution of enone (S)-5b (45.0 mg, 0.214 mmol) and 2-naphthalene thiol (38.0 mg, 0.24 mmol) in dry chloroform (3 ml) was added catalytic amount of triethyl amine at room temperature and the reaction mixture was stirred at room temperature for 4 hours under nitrogen atmosphere. The chloroform was removed under vacuum and residue was purified by flash column chromatography over silica using ethyl acetate in pet ether (1:9) as eluent to afford separable title compounds anti-6a and syn-6a (67.0 mg, 86%) as colourless solid; $R_f$=0.45, (anti, major), 0.4 (syn, minor) in (ethyl acetate/pet.ether, 1:9); $^1$H NMR ($CDCl_3$, 400 MHz) (anti-6a) δ 7.95-7.45 (7H, m, ArH), 5.25 (1H, d, J=8.4 Hz, CHO), 3.75 (1H, m, CHS), 3.0-2.9 (1H, dd, J=8.6, 10.5 Hz, CHH), 2.35-2.45 (1H, dd, J=9.2, 10 Hz, CHH), 1.2 (9H, s, $(CH_3)_3$), 1.15, 1.01 (6H, s, 2×$CH_3$); $^{13}$C ($CDCl_3$; 100.6 MHz) δ 215.2, 177.9, 133.6, 132.6, 132.7 132.3, 130.2, 130.0, 128.8, 127.7, 127.5, 126.7, 126.6, 80.9, 50.0, 45.5, 42.8, 39.0, 27.2, 22.8, 18.6; (syn-6a) δ 7.9-7.45 (7H, m, ArH), 5.45 (1H, d, J=4.3 Hz, CHO), 4.05 (1H, m, CHS), 2.94-2.84 (1H, dd, J=8.1, 10.6 Hz, CHH), 2.35-2.45 (1H, dd, J=7.95, 10.8 Hz, CHH), 1.3 (9H, s, $(CH_3)_3$), 1.12, 1.08 (6H, s, 2×$CH_3$); $^{13}$C ($CDCl_3$; 100.6 MHz) 217.1, 177.64, 134.0, 132.8, 132.3, 131.1, 129.5, 129.2, 128.1, 127.8, 127.0, 126.7, 80.0, 51.4, 46.7, 42.9, 39.8, 27.8, 27.4, 23.5, 18.4; HRMS (ES+, Na): cacd. for [M+Na]$^+$ $C_{22}H_{26}O_3SNa$: 393.15; found: 393.1499.

(b) Preparation of (2R)-2-tert-butoxycarbonylamino-3-[(1R,2S)-2-(2,2-dimethylpropionyloxy)-3,3-dimethyl-4-oxocyclopentylsulfanyl]-propionic acid anti-6b (CTM-217) & (2R)-2-tert-butoxycarbonylamino-3-[(1S,2S)-2-(2,2-dimethylpropionyloxy)-3,3-dimethyl-4-oxocyclopentylsulfanyl]-propionic acid syn-6b (c) Preparation of 2,2-dimethylpropionic acid (1R,5S)-2,2-dimethyl-5-(naphthalen-2-ylsulfanyl)-3-oxocyclopentyl ester anti-6c (CTM-191) & 2,2-dimethylpropionic acid (1R,5R)-2,2-dimethyl-5-(naphthalen-2-ylsulfanyl)-3-oxocyclopentyl ester syn-6c (CTM-192)

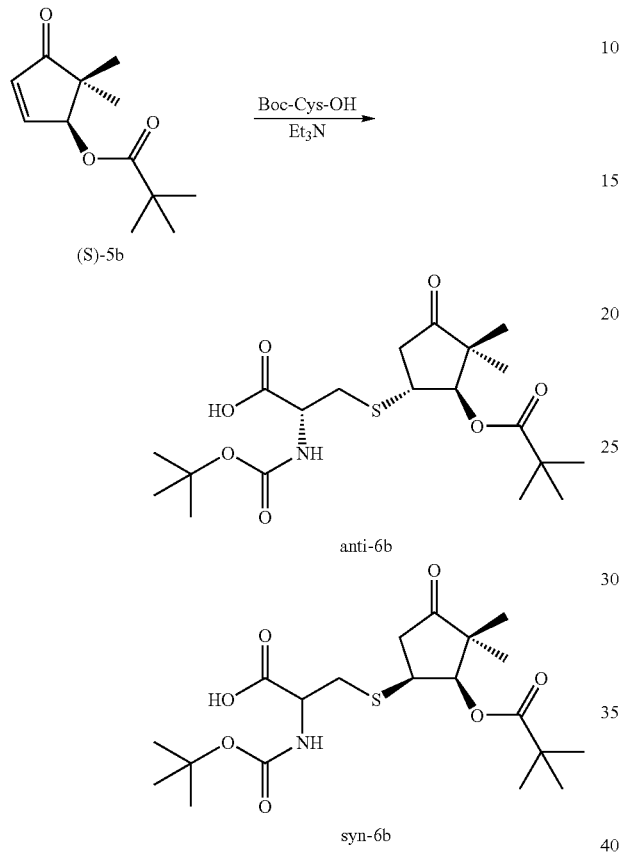

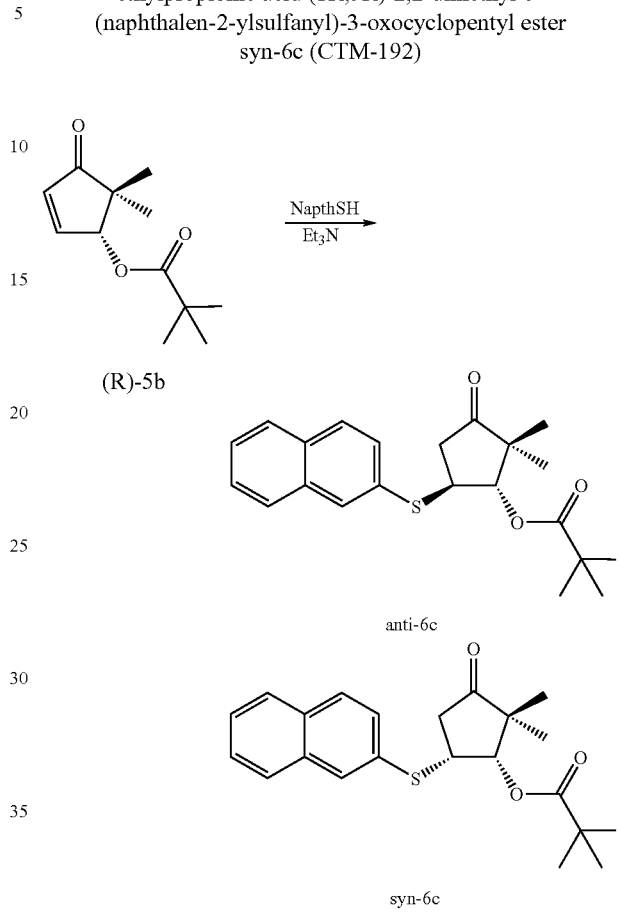

To a solution of enone (S)-5b (60.0 mg, 0.285 mmol) and Boc-Cys-OH (69.0 mg, 0.314 mmol) in dry chloroform (3 ml) was added triethyl amine (44 µl, 0.314 mmol) at room temperature and the reaction mixture was stirred at room temperature for 10 hours under nitrogen atmosphere. The chloroform was removed under vacuum and residue was acidified with AcOH (0.314 mmol) and purified by flash column chromatography over silica using ethyl acetate in pet.ether (1:1) as eluent to afford separable title compounds anti-6b and syn-6b (74.0 mg, 60%) as colourless solid; $R_f$=0.5, (anti, major), 0.45 (syn, minor) in (ethyl acetate/pet.ether/AcOH, 1:1:0.1); $^1$H NMR (CDCl$_3$, 400 MHz) (anti-6b) δ 5.5 (1H, br. d, J=6.0 Hz, NH), 5.1 (1H, d, J=7.6 Hz, CHO), 4.58 (1H, br.s, CH), 3.42 (1H, m, CHS), 3.2-3.1 (2H, m, CH$_2$), 2.95-2.9 (1H, dd, J=8.8, 10.3 Hz, CHH), 2.4-2.3 (1H, dd, J=9.4, 9.7 Hz, CHH), 1.45; 1.26 (18H, s, 2x(CH$_3$)$_3$), 1.18, 1.0 (6H, s, 2xCH$_3$); $^{13}$C (CDCl$_3$; 100.6 MHz) δ 215.6, 177.9, 177.0, 174.6, 81.7, 80.7, 53.6, 49.9, 43.3, 43.0, 39.1, 33.4, 29.7, 28.3, 27.2, 23.1, 20.7, 18.6; (syn-6b) δ 5.45 (1H, br.s, NH), 5.3 (1H, d, J=3.5 Hz, CHO), 4.48 (1H, br. s, CH), 3.68 (1H, m, CHS), 3.2-2.95 (2H, m, CH$_2$), 2.8-2.7 (1H, dd, J=6.8, 6.7 Hz, CHH), 2.3-2.22 (1H, dd, J=12.0, 6.7 Hz, CHH), 1.46, 1.24 (18H, s, 2x(CH$_3$)$_3$), 1.12, 1.06 (6H, s, 2xCH$_3$); $^{13}$C (CDCl$_3$; 100.6 MHz) δ 216.5, 178.1, 173.2, 81.0, 79.0, 51.0, 43.2, 41.2, 39.4, 34.0, 29.7, 28.3, 27.4, 27.2, 23.1, 20.4, 18.0.

To a solution of enone (R)-5b (45.0 mg, 0.214 mmol) and 2-naphthalene thiol (38.0 mg, 0.24 mmol) in dry chloroform (3 ml) was added catalytic amount of triethyl amine at room temperature and the reaction mixture was stirred at room temperature for 24 hours under nitrogen atmosphere. The chloroform was removed under vacuum and residue was purified by flash column chromatography over silica using ethyl acetate in pet.ether (1:9) as eluent to afford separable title compounds anti-6c and syn-6c (64.0 mg, 81%) as colourless solid; $R_f$=0.45, (anti, major), 0.4 (syn, minor) in (ethyl acetate/pet.ether, 1:9); $^1$H NMR (CDCl$_3$, 400 MHz) (anti-6c) δ 7.95-7.5 (7H, m, ArH), 5.25 (1H, d, J=8.4 Hz, CHO), 3.8 (1H, m, CHS), 3.0-2.9 (1H, dd, J=8.6, 10.5 Hz, CHH), 2.3-2.4 (1H, dd, J=9, 10 Hz, CHH), 1.2 (9H, s, (CH$_3$)$_3$), 1.15, 1.01 (6H, s, 2xCH$_3$); $^{13}$C (CDCl$_3$; 100.6 MHz) δ 215.6, 177.9, 134.0, 133.0, 132.6, 130.5, 130.4, 129.2, 128.1, 127.9, 127.1, 126.9, 81.3, 50.4, 45.9, 43.2, 39.4, 27.5, 23.1, 19.0; (syn-6c) δ 7.9-7.45 (7H, m, ArH), 5.45 (1H, d, J=4.14 Hz, CHO), 4.05 (1H, m, CHS), 2.95-2.85 (1H, dd, J=8.1, 10.6 Hz, CHH), 2.35-2.45 (1H, dd, J=7.94, 11 Hz, CHH), 1.3 (9H, s, (CH$_3$)$_3$), 1.12, 1.08 (6H, s, 2xCH$_3$); $^{13}$C (CDCl$_3$; 100.6 MHz) 217.1, 177.6, 134.0, 132.8, 132.3, 131.1, 129.5, 129.2, 128.1, 127.8, 127.0, 126.7, 80.0, 51.4, 46.7, 42.9, 39.8, 27.8, 27.4, 23.5, 18.4; HRMS (ES+, Na): cacd. for [M+Na]$^+$ C$_{22}$H$_{26}$O$_3$SNa: 393.15; found: 393.1493.

(d) Preparation of (2R)-2-tert-butoxycarbonylamino-3-[(1S,2R)-2-(2,2-dimethylpropionyloxy)-3,3-dimethyl-4-oxocyclopentylsulfanyl]-propionic acid anti-6d (CTM-218) & (2R)-2-tert-butoxycarbonylamino-3-[(1R,2R)-2-(2,2-dimethylpropionyloxy)-3,3-dimethyl-4-oxocyclopentylsulfanyl]-propionic acid syn-6d

Example 9

Compounds in Accordance with the Invention, with Structures 2a-2u, were Prepared Using General Method A as Follows

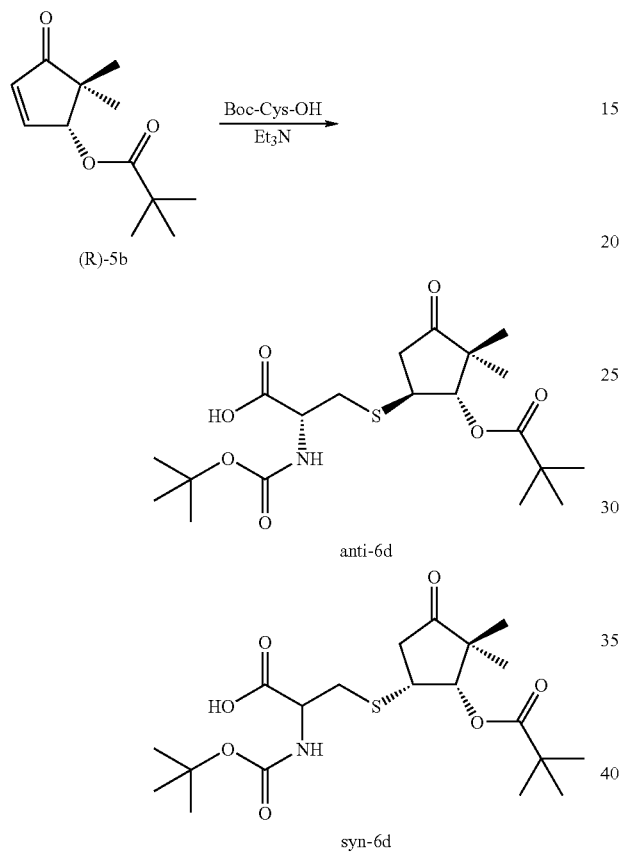

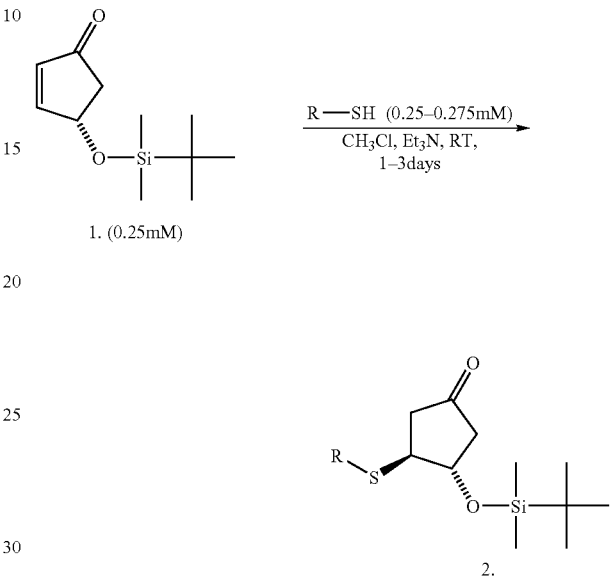

General Procedure: To a solution of enone (1) (0.25 mM) and Thiol (0.25-0.275 mM) in dry chloroform (5 ml) was added catalytic amount of triethyl amine (20 μl) at room temperature and the reaction mixture was stirred at room temperature for 1-3 days under nitrogen atmosphere. The chloroform was removed under vacuum and residue was purified by flash column chromatography over silica using ethyl acetate in hexane as eluent to afford the title compound 2.

To a solution of enone (R)-5b (45.0 mg, 0.214 mmol) and Boc-Cys-OH (52.0 mg, 0.235 mmol) in dry chloroform (3 ml) was added triethyl amine (30 μl, 0.235 mmol) at room temperature and the reaction mixture was stirred at room temperature for 24 hours under nitrogen atmosphere. The chloroform was removed under vacuum and residue was acidified with AcOH (0.235 mmol) and purified by flash column chromatography over silica using ethyl acetate in pet.ether (1:1) as eluent to afford separable title compounds anti-6d and syn-6d (60.0 mg, 65%) as colourless solid; $R_f$=0.5, (anti, major), 0.45 (syn, minor) in (ethyl acetate/pet.ether/AcOH, 1:1:0.1); $^1$H NMR (CDCl$_3$, 400 MHz) (anti-6d) δ 5.35 (1H, br.s, NH), 5.1 (1H, d, J=7.5 Hz, CHO), 4.56 (1H, br. s, CH), 3.38 (1H, m, CHS), 3.22-3.15 (2H, m, CH$_2$), 2.95-2.9 (1H, dd, J=8.9, 10.2 Hz, CHH), 2.38-2.3 (1H, dd, J=9.0, 10.0 Hz, CHH), 1.46, 1.26 (18H, s, 2x(CH$_3$)$_3$), 1.18, 1.0 (6H, s, 2xCH$_3$); $^{13}$C (CDCl$_3$; 100.6 MHz) δ 215.5, 177.9, 176.7, 174.8, 155.4, 82.2, 80.7, 53.0, 49.9, 43.0, 39.0, 33.9, 28.3, 27.1, 23.2, 20.6, 18.6.

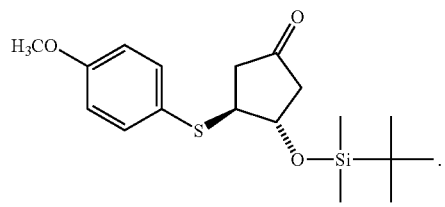

2a (CTM-169). $^1$H NMR (CDCl$_3$, 400 MHz) δ 7.44-6.9 (m, 4H, ArH), 4.33 (1H, m, CH—O), 3.82 (3H, s, OCH$_3$), 3.6 (1H, m, CH—S), 2.85-2.75 (2H, m, CH$_2$), 2.2-2.1 (2H, m, CH$_2$), 2.5 (3H, s, CH$_3$), 0.84 (9H, s, t-but), 0.04, –0.06 (6H, s, 2xCH$_3$); $^{13}$C (CDCl$_3$; 100.6 MHz) δ 215.64, 160.39, 135.22, 135.76, 124.12, 115.43, 115.22, 73.66, 68.67, 60.73, 55.78, 52.40, 45.78, 42.06, 40.42, 26.00, 21.38, 18.28, 14.56, –4.57, –4.65; HRMS (CI, NH$_3$): cacd. for [M+NH$_3$]$^+$ C$_{18}$H$_{32}$O$_3$SSiN: 370.18723; found: 390.18646.

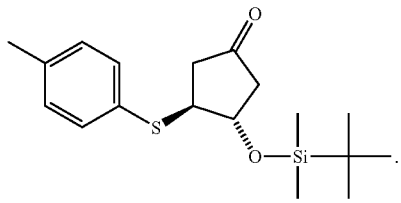

2b 2b (CTM-80). $^1$H NMR (CDCl$_3$, 250 MHz) δ 7.5-7.2 (4H, m, ArH), 4.4 (1H, m, CH—O), 3.8 (1H, m, CH—S), 3.0-2.80 (2H, m, CH$_2$), 2.3-2.1 (2H, m, CH$_2$), 2.5 (3H, s, CH$_3$), 0.84 (9H, s, t-but), 0.01, −0.4 (6H, s, 2xCH$_3$); HRMS (CI, NH$_3$): cacd. for [M+NH$_3$]$^+$ C$_{18}$H$_{32}$O$_2$SSiN: 354.19232; found: 354.19196.

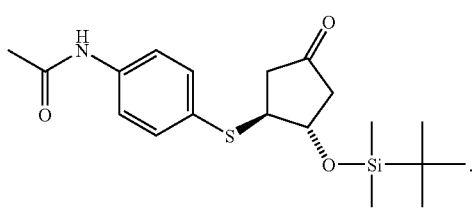

2c 2c (CTM-81). $^1$H NMR (CDCl$_3$, 400 MHz) δ 7.8 (1H, br.s, NH), 7.6-7.3 (4H, m, ArH), 4.4 (1H, m, CH—O), 3.7 (1H, m, CH—S), 2.9-2.75 (2H, m, CH$_2$), 2.25-2.15 (5H, m, CH$_3$, CH$_2$), 0.85 (9H, s, t-but), −0.01, −0.02 (6H, s, 2xCH$_3$); HRMS (CI, NH$_3$): cacd. for [M+NH$_3$]$^+$ C$_{19}$H$_{33}$O$_3$SSiN$_2$: 397.19812; found: 397.19836.

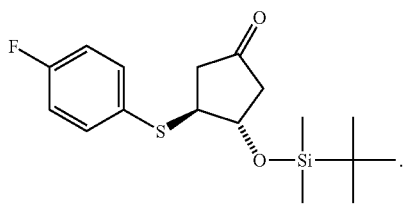

2d 2d (CTM-108). $^1$H NMR (CDCl$_3$, 250 MHz) δ 7.6-6.9 (4H, m, ArH), 4.3 (1H, m, CH—O), 3.7 (1H, m, CH—S), 2.8-2.6 (2H, m, CH$_2$), 2.3-2.1 (2H, m, CH$_2$), 0.8 (9H$^-$, s, t-but), −0.05, −0.1 (6H, s, 2xCH$_3$); HRMS (CI, NH$_3$): cacd. for [M+NH$_3$]$^+$ C$_{18}$H$_{32}$O$_2$SSiN: 354.19232; found: 354.19196.

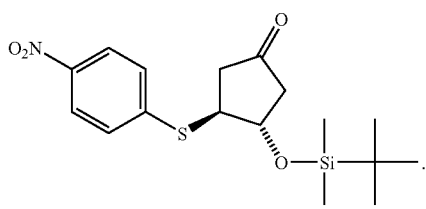

2e 2e (CTM-107). $^1$H NMR (CDCl$_3$, 250 MHz) δ 8.2-7.4 (4H, m, ArH), 4.4 (1H, m, CH—O), 3.9 (1H, m, CH—S), 3.1-2.80 (2H, m, CH$_2$, 2.3-2.1 (2H, m, CH$_2$), 2.5 (3H, s, CH$_3$), 0.84 (9H, s, t-but), 0.01,-0.04 (6H, s, 2xCH$_3$); HRMS (CI, NH$_3$): cacd. for [M+NH$_3$]$^+$ C$_{18}$H$_{32}$O$_2$SSiN: 354.19232; found: 354.19196.

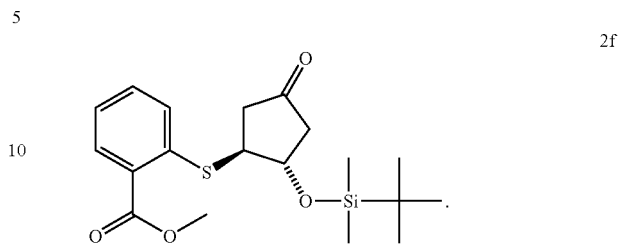

2f 2f (CTM-82). $^1$H NMR (CDCl$_3$, 250 MHz) δ 8.2-7.2 (4H, m, ArH), 4.5 (1H, m, CH—O), 3.9 (4H, m, CH—S, OCH$_3$), 3.1-2.80 (2H, m, CH$_2$), 2.4-2.1 (2H, m, CH$_2$), 0.9 (9H, s, t-but), 0.01, 0.05 (6H, s, 2xCH$_3$); HRMS (CI, NH$_3$): 398 [M+NH$_3$]$^+$, (7%), 186 [M−1]$^+$, (100%).

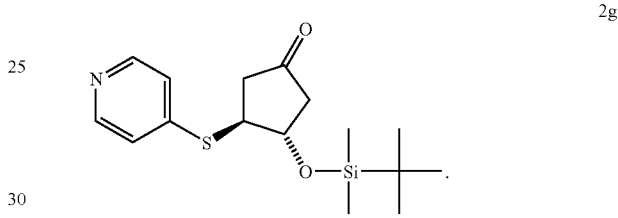

2g 2g (CTM-132). $^1$H NMR (CDCl$_3$, 250 MHz) δ 8.4-7.2 (4H, m, ArH), 4.5 (1H, m, CH—O), 3.9 (1H, m, CH—S), 3.1-2.70 (2H, m, CH), 2.3-2.15 (2H, m, CH$_2$), 0.9 (9H, s, t-but), 0.01, −0.05 (6H, s, 2xCH$_3$); HRMS (CI, NH$_3$).

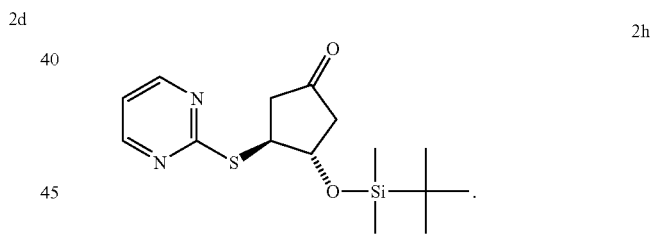

2h 2h (CTM-84). $^1$H NMR (CDCl$_3$, 250 MHz) δ 8.5-7.0 (3H, m, ArH), 4.5 (1H, m, CH—O), 3.9 (1H, m, CH—S), 3.1-2.60 (2H, m, CH$_2$), 2.4-2.1 (2H, m, CH$_2$), 0.9 (9H, s, t-but), 0.15, 0.05 (6H, s, 2xCH$_3$); HRMS (CI, NH$_3$): 325 [M+H]$^+$, (14.8%).

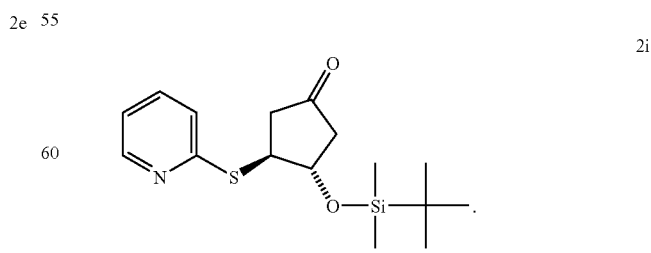

2i 2i (CTM-86). $^1$H NMR (CDCl$_3$, 250 MHz) δ 7.5-6.9 (4H, m, ArH), 4.7 (1H, m, CH—O), 4.5 (1H, m, CH—S), 2.8-2.6

(2H, m, CH₂), 2.6-2.3 (2H, m, CH₂), 0.9 (9H, s, t-but), 0.15, −0.05 (6H, s, 2xCH₃); HRMS (CI, NH₃): 324 [M+H]⁺, (5%).

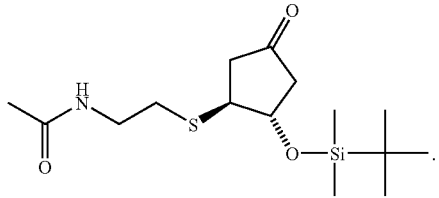

2j (CTM-83). ¹H NMR (CDCl₃, 250 MHz) δ 6.2 (1H, br.m, NH), 4.4 (1H, m, CH—O), 3.5 (2H, m, CH₂), 3.3 (1H, m, CH—S), 2.9-2.6 (4H, m, CH₂), 2.2-2.0 (2H, m, CH₂), 1.9 (3H, s, CH₃), 0.8 (9H, s, t-but), 0.1, 0.05 (6H, s, 2xCH₃); HRMS (CI, NH₃): 332 [M+H]⁺, (20.5%), 349 [M+NH₄]⁺, (32.4%).

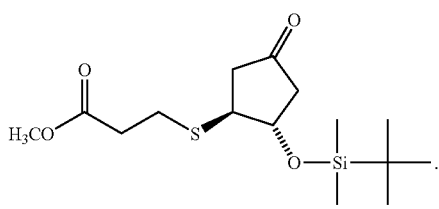

2k (CTM-88). ¹H NMR (CDCl₃, 250 MHz) δ 4.4 (1H, m, CH—O), 3.7 (3H, s, CH₃), 3.3 (1H, m, CH—S), 2.9-2.5 (6H, m, CH₂), 2.2-2.0 (2H, m, CH₂), 0.85 (9H, s, t-but), 0.1, 0.05 (6H, s, 2xCH₃); HRMS (CI, NH₃): 350 [M+NH₄]⁺, (32%).

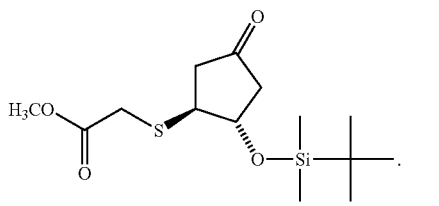

2l (CTM-87). ¹H NMR (CDCl₃, 250 MHz) δ 4.4 (1H, m, CH—O), 3.7 (3H, s, CH₃), 3.5-3.2 (3H, m, CH—S, CH₂), 2.9-2.6 (2H, m, CH₂), 2.2-2.0 (2H, m, CH₂), 0.85 (9H, s, t-but), 0.1, 0.05 (6H, s, 2xCH₃).

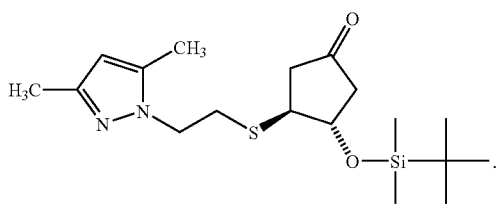

2m (CTM-109). ¹H NMR (CDCl₃, 250 MHz) δ 5.8 (1H, s, CH), 4.3-4.1 (3H, m, CH—O, CH₂), 3.1-2.9 (3H, m, CH—S, CH₂), 2.8-2.5 (2H, m, CH₂), 2.3-2.0 (8H, m, CH₃, CH₂), 0.85 (9H, s, t-but), 0.1, 0.05 (6H, s, 2xCH₃).

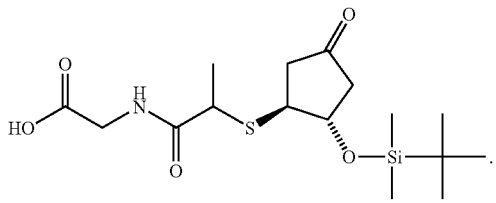

2n (CTM-110). ¹H NMR (CDCl₃, 400 MHz) δ 7.5 (1H, br.s, NH), 4.25 (1H, m, CH—O), 3.85 (2H, br.m, CH₂), 3.58, 3.45 (1H, m, CH—S), 3.3 (1H, m, CH—S), 2.8-2.5 (2H, m, CH₂), 2.2-2.05 (2H, m, CH₂), 1.4 (3H, m, CH₃), 0.76, 0.75 (9H, s, t-but), 0.02, 0.01, −0.01, −0.08 (6H, s, 2xCH₃); ¹³C (CDCl₃; 100.6 MHz) δ 215.5, 215.1, 173.8, 60.9, 48.0, 47.1, 46.9, 44.7, 44.0, 43.8, 26.1, 18.9, 18.7, 18.3, 14.5, −3.25, −4.3, −4.4, −4.44.

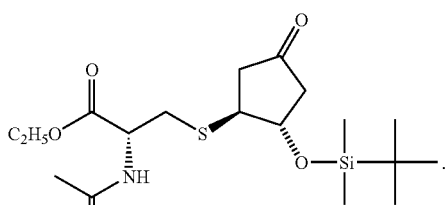

2o (CTM-131). ¹H NMR (CDCl₃, 250 MHz) δ 6.5 (1H, br.s, NH), 4.8 (1H, m, CH), 4.25 (3H, m, CH—O, CH₂), 3.3 (1H, m, CH—S), 3.2-2.6 (4H, m, CH₂), 2.2-2.0 (5H, m, CH₃CH₂), 1.3 (3H, m, CH₃), 0.85 (9H, s, t-but), 0.08, 0.05 (6H, s, 2xCH₃).

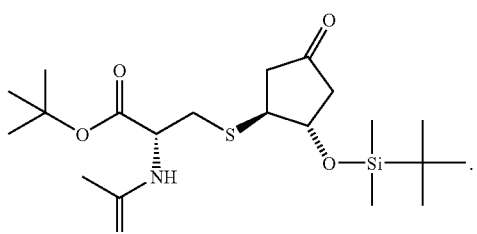

2p (CTM-106). ¹H NMR (CDCl₃, 250 MHz) δ 6.4 (1H, br.s, NH), 4.8 (1H, m, CH), 4.35 (1H, m, CH—O), 3.3 (1H, m, CH—S), 3.2-2.6 (4H, m, CH₂), 2.2-2.0 (5H, m, CH₃, CH₂), 1.5 (9H, m, t-but), 0.9 (9H, s, t-but), 0.15, 0.1 (6H, s, 2xCH₃).

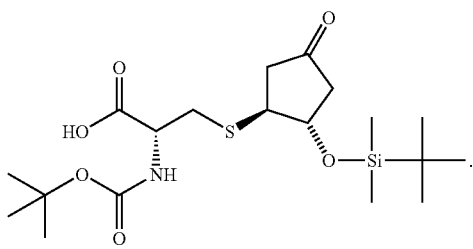

2q (CTM-145). $^1$H NMR (CDCl$_3$, 400 MHz) δ 5.4 (1H, br.s, NH), 4.6 (1H, br.m, CH), 4.4 (1H, m, CH—O), 3.4 (1H, m, CH—S), 3.2-3.0 (2H, m, CH$_2$), 2.9-2.62 (2H, m, CH$_2$), 2.2-2.1 (2H, m, CH$_2$), 1.47 (9H, m, t-but), 0.9 (9H, s, t-but), 0.03, −0.01 (6H, s, 2xCH$_3$); $^{13}$C (CDCl$_3$; 100.6 MHz) δ 214.6, 174.7, 155.8, 81.1, 75.1, 53.4, 49.1, 46.5, 43.2, 34.2, 28.6, 26.0, 25.9, 18.3, −3.28, −4.36, −4.4.

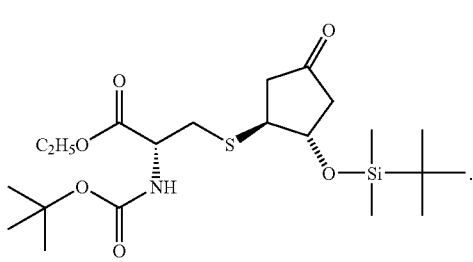

2r (CTM-184). $^1$H NMR (CDCl$_3$, 400 MHz) δ 5.29 (1H, br.d, J=6.2 Hz, NH), 4.53 (1H, m, CH), 4.32 (1H, m, CH—O), 4.2 (2H, m, CH$_2$), 3.32 (1H, m, CH—S), 3.13-2.94 (2H, m, CH$_2$), 2.85-2.62 (1H, m, CH$_2$), 2.17-2.08 (2H, m, CH$_2$), 1.43 (9H, s, t-but), 1.28 (3H, t, J=7.15 Hz, CH$_3$), 0.86 (9H, s, t-but), 0.09, 0.07 (6H, s, 2xCH$_3$), $^{13}$C (CDCl$_3$; 100.6 MHz) δ 214.34, 171.04, 155.49, 80.6, 75.11, 62.19, 60.71, 53.59, 49.38, 49.00, 46.4, 43.08, 34.64, 28.66, 26.03, 18.27, 14.52, −4.38, −4.43; HRMS (ES+): cacd for [M+Na]$^+$ C$_{21}$H$_{39}$NO$_6$SSiNa: 484.215; found: 484.2165.

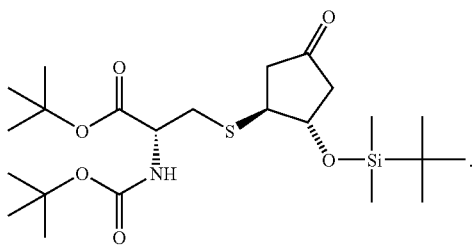

2s (CTM-183). $^1$H NMR (CDCl$_3$, 400 MHz) δ 5.28 (1H, d, J=6.36 Hz, NH), 4.45 (1H, m, CH), 4.35 (1H, m, CH—O), 3.35 (1H, m, CH—S), 3.10-2.95 (2H, m, CH$_2$), 2.88-2.65 (1H, m, CH$_2$), 2.18-2.1 (2H, m, CH$_2$), 1.48, 1.45 (18H, s, 2xt-but), 0.88 (9H, s, t-but), 0.11, 0.085 (6H, s, 2xCH$_3$), $^{13}$C (CDCl$_3$; 100.6 MHz) δ 214.5, 170.05, 155.5, 83.1, 80.4, 75.07, 60.71, 54.08, 49.18, 46.35, 43.12, 34.88, 28.69, 28.36, 26.04, 21.36, 18.28, 14.55, −4.34, −4.42; HRMS (ES+): cacd for [M+Na]$^+$ C$_{23}$H$_{43}$NO$_6$SSiNa: 512.2468; found: 512.2478.

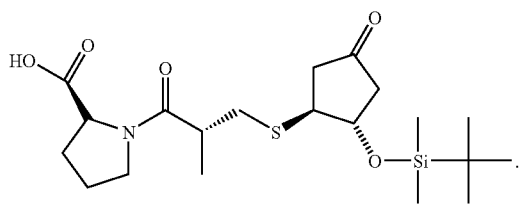

2t (CTM-182). HRMS (ES−): cacd for [M−H]$^-$ C$_{20}$H$_{34}$NO$_5$SSi: 428.1914; found: 428.1927.

2u (CTM-115). $^1$H NMR (CDCl$_3$, 400 MHz) δ 10.88 (1H, br. s, OH), 6.84 (1H, d J=7.5 Hz, NH), 4.77 (1H, dt J=7.5 & 5.3 Hz, CHNHAc), 4.28 (1H, dt J=5.5 & 2.9 Hz, CHOTBS), 3.29 (1H, dt J=7.5 & 3.5 Hz, CHSCys), 3.11 (1H, dd J=13.7 & 4.9 Hz, CHHS), 2.97 (1H, dd J=13.7 & 5.7 Hz, CHHS), 2.75 (1H, dd J=18.8 & 7.5 Hz, CHHCHSCys), 2.61 (1H, dd J=18.2 & 5.5 Hz, CHHCHOTBS), 2.12-2.02 (2H, m, CHH-CHSCys+CHHCHOTBS), 2.01 (3H, s, NC=OCH$_3$), 0.79 (9H, s, SiC(CH$_3$)$_3$), 0.03 (3H, s, SiCH$_3$), 0.00 (3H, s, SiCH$_3$); $^{13}$C (CDCl$_3$; 100.6 MHz) 214.9 (s), 172.9 (s), 171.6 (s), 74.4 (d), 52.0 (d), 48.4 (d), 45.9 (t), 42.6 (t), 33.2 (t), 25.5 (q), 22.5 (q), 17.7 (s), −4.9 (q), −5.0 (q).

Example 10

Preparation of CTM-165

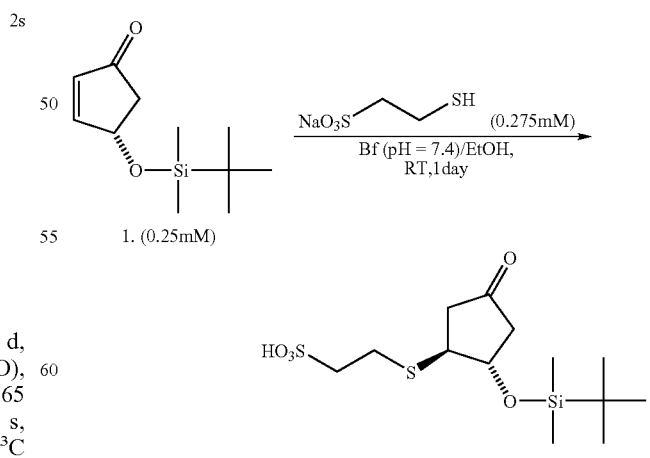

CTM-165: A solution of enone (1) (0.25 mM) and Thiol (0.275 mM) in Buffer (pH=7.4)(5.1 ml)/EtOH (0.9 ml) was stirred at room temperature for 1 day under nitrogen atmosphere. The solvent was removed under vacuum and residue was acidified with AcOH (0.275) mM and purified by flash column chromatography over silica using ethyl acetate in hexane as eluent to afford the tide compound 3 (CTM-165); $^1$H NMR (CDCl$_3$, 400 MHz) δ 4.6 (1H, br.s, CH—O), 4.3 (1H, br.m, CH—S), 3.5-2.2 (8H, m, CH$_2$), 0.9 (9H, s, t-but), 0.1, 0.08 (6H, s, 2xCH$_3$); $^{13}$C (CDCl$_3$; 100.6 MHz) δ 216.82, 216.5, 74.1, 72.6, 48.8, 48.5, 47.9, 46.5, 43.8, 43.2, 29.7, 25.9, 25.8, 18.2, 18.0, −4.54, −4.57, −4.74; HRMS (ES−): cacd. for [M$^-$], C$_{13}$H$_{25}$O$_5$S$_2$Si: 353.0913; found: 353.0898.

Activity of Compounds in Accordance with the Invention

Preferred compounds of the present invention have activity in one or more of the assays described in Examples 11 to 17 below.

Certain compounds of the present invention may be advantageous in avoiding the affect of lowering blood pressure that is associated with various prostaglandins. An assay for this is set out in Example 18 below.

Example 11

Effect of Inventive Compounds on the Reactivity of Transcription Factors HSF and NF-κB Methods: Human lymphoblastoid Jurkat T cells were grown at 37° C. in a 5% CO$_2$ atmosphere in RPM1 1640 medium (GIBCO BRL, Gaithersburg, Md.) supplemented with 10% fetal calf serum (FCS, Hyclone Europe Ltd, UK) 2 mM glutamine and antibiotics according to the method described by A. Rossi et al. (Proc. Natl. Acad. Sci. USA 94: 746-750, 1997). The test compounds were stored as a 100% ethanolic stock solution (100 mM) or in DMSO (100 mM) and diluted to the appropriate concentration in culture medium at the time of use. Cells were treated with different concentrations of test compound for 1 hour and then stimulated with 12-O-tetradecanoylphorbol-13-acetate (TPA, 25 ng/ml), which is a strong inducer of NF-κB. Control cells received an equal amount of control diluent. After 3 hours whole-cell extracts were prepared and subjected to analysis of DNA-binding activity by EMSA (Electrophoretic Mobility Shift Assay) for detection of HSF or NF-κB activation, according to the method described by A. Rossi et al. (Proc. Natl. Acad. Sci. USA 94: 746-750, 1997).

Specificity of protein-DNA complexes was verified by immunoreactivity with polyclonal antibodies specific for p65 (RelA) or for HSF-1, for NF-κB and HSF respectively. Quantitative evaluation of NF-κB and HSF-DNA complex formation was determined by Molecular Dynamics Phosphorimager (MDP) analysis and was expressed in arbitrary units, as described in A. Rossi et al. (J. Biol. Chem. 273: 16446-16452, 1998). The results from representative experiments are shown in FIGS. 1(b), 2(b), 3(b), 4(b), 5 and 6(b) for compounds CTM-50, CTM-49, CTM-36, CTM-30, CTC-130 and CTC-109, as identified above. These results show that all of these latter compounds are inhibitors of NF-κB.

Example 12

Effect of Inventive Compounds on the Replication of Sendai Virus

Methods: Monkey kidney 37RC cells were grown at 37° C. under the conditions described in Example 10 for T cells. The parainfluenza Sendai virus (SV) was grown in the allantoic cavity of 10-day-old embroynated eggs. Viral titre was expressed in haemagglutinating units (HAU) per ml; haemagglutinin titration was done according to standard procedures using human 0 Rh+ erythrocytes, as described in C. Amici et al. (J. Virol. 68: 6890-6899, 1994). Confluent monolayers of 37RC cells were infected with SV virus (5 HAU/10$^5$ cells) for 1 h at 37° C., and then treated with different concentrations of test compounds. Virus yield at 24 hours after infection was determined in the supernatant of infected cells by HAU titration. The results from representative experiments are shown in FIGS. 1(a), 2(a), 3(a), 4(a), and 6(a) for compounds CTM-50, CTM-49, CTM-36, CTM-30 and CTC-109, as identified above.

The ID$_{50}$ (the 50% inhibitory dose/concentration) values at 24 hours and the TD$_{100}$ (the dose or concentration at which the tested compound was 100% toxic to uninfected cells, determined visually by microscopy) for the tested compounds and the unsaturated analogues, CTC-1 (cyclopent-2-en-1-one) and CTC-8 (4-tert-butyldimethylsilyloxy-cyclopent-2-en-1-one), to compounds CTM-49 and CTM-36 are given below.

| Compound | ID$_{50}$/μM | TD$_{100}$/μM |
| --- | --- | --- |
| CTM-50 | 10 | >500 |
| CTM-49 | 20 | >500 |
| CTM-36 | 4 | >500 |
| CTM-30 | 3 | 50 |
| CTC-109 | 3 | 500 |
| CTC-1 | 90 | >500 |
| CTC-8 | 0.5 | 100 |

These latter results show that, whilst all of the compounds tested are inhibitors of Sendai virus replication, the ratio of the ID$_{50}$ to the TD$_{100}$ is greater for CTM-49 and CTM-36 (compounds in accordance with the invention) than it is for their analogues CTC-1 and CTC-8 (which lie outside of the scope of the present invention).

The results obtained for some further compounds in accordance with the invention that are described in Examples 8-10 are set out below:

| Compound | ID$_{50}$/μM | TD$_{100}$/μM |
| --- | --- | --- |
| CTM-68 | 1 | 9.8 |
| CTM-78 | 3 | 18.6 |
| CTM-80 | 1 | 50 |
| CTM-81 | 1 | 50 |
| CTM-82 | 1 | 50 |
| CTM-83 | 3 | 50 |
| CTM-84 | 1 | 10 |
| CTM-85 | 3 | 50 |
| CTM-86 | 2 | 10 |
| CTM-87 | 4 | 50 |
| CTM-88 | 10 | 50 |
| CTM-106 | 4 | 50 |
| CTM-107 | 0.3 | 10 |
| CTM-108 | 4 | 50 |
| CTM-109 | 4 | 50 |
| CTM-110 | 1 | 50 |
| CTM-115 | 50 | >500 |
| CTM-131 | 10 | 50 |
| CTM-132 | 0.2 | 10 |
| CTM-145 | 0.8 | 50 |
| CTM-165 | 1 | 50 |
| CTM-169 | 1.5 | 50 |
| CTM-182 | 5 | 100 |
| CTM-183 | 1.6 | 50 |
| CTM-184 | 1 | 50 |
| CTM-191 | 4 | 50 |

-continued

| Compound | ID$_{50}$/μM | TD$_{100}$/μM |
|---|---|---|
| CTM-192 | 2 | 50 |
| CTM-193 | 3 | 50 |

Example 13

Effect of Inventive Compounds on the Reactivity of Transcription Factors HSF and NF-κB (Second Method)

Method: HeLa cell clone 13B, stably transfected with a luciferase reporter plasmid controlled by the human hsp70 promoter, and HeLa κB-transformed cells, stably transfected with a luciferase reporter plasmid controlled by a synthetic NF-κB-STM construct, were maintained in DMEM medium supplemented with 10% FBS, L-glutamine (2 mM) and G418 (250 μg/ml) at 37° C. in a 5% $CO_2$ humidified atmosphere.

Cells were seeded at a density of $4 \times 10^4$ cells/well in 96-well plates. After 18-20 h, the medium was removed and cells were treated for 8 h with the test compounds (100 μl) at the appropriate dilutions in serum-free medium. For the NF-κB-dependent reporter gene assay, cells were stimulated with TPA (25 ng/ml) 2 h after exposure to the compounds.

After incubation, the medium was removed and cells were lysed in 10 μl of lysis buffer. The luciferase activity was determined by adding 100 μl of substrate and measuring the release of light using a Victor 1420 microplate reader (Wallac, Finland).

Production of HeLa Cell Clones Stably Transfected with NF-κB-LUC

The fragment Kpn I-BamH I from the pGL3 basic vector containing the luciferase gene (PROMEGA) was inserted in the pcDNA3 vector (INVITROGEN) digested with Bgl II-KpnI. (This digestion removes the CMV-promoter from pcDNA3.) The resulting new vector was digested with Kpn I-Hind III and a promoter containing a '5xNF-κB binding sites—TATA box' sequence was inserted upstream of the luciferase gene. This vector has been named STM.

To obtain stable HeLa cell lines expressing the luciferase gene under the control of NF-κB, HeLa cells were transfected (using lipofectamine plus GIBCO) with the STM-Pvu I linearized vector, and selected for 20 days with G418 (800 μg/ml). After selection, the resistant HeLa cell pool was controlled (in quadruplicate samples) for luciferase activity after stimulation with TNFα, IL-1 and TPA.

The respective luciferase activities were:

1) Control: 1369±149
2) TNFα: 6111±1231
3) IL-1: 11814±1151
4) TPA: 7181±444

Clones were selected.

The results obtained for 2-tert-Butoxycarbonylamino-3-[2-(tert-butyl-dimethyl-silanyloxy)-5-oxo-cyclohexylsulfanyl]-propionic acid methyl ester (CTM-68) and 2-tert-Butoxycarbonylamino-3-[3-(tert-butyl-dimethyl-silanyloxy)-5-oxo-cyclohexylsulfanyl]-propionic acid methyl ester (CTM-78), both of which belong to group E, were as follows:

|  | HSF; AC$_{200}$/μM | NF-κB; IC$_{50}$/μM |
|---|---|---|
| CTM-68 | 98 | 17 |
| CTM-78 | 45 | 22 |

The results obtained for some further compounds in accordance with the invention that are described in Examples 8-10 are set out below:

|  | HSF; AC$_{200}$/μM | NF-κB; IC$_{50}$/μM |
|---|---|---|
| CTM-80 | 60 | >100 |
| CTM-81 | 28 | 31 |
| CTM-82 | 35 | 54 |
| CTM-83 | 27 | 47 |
| CTM-84 | 28 | 28 |
| CTM-85 | 28 | 43 |
| CTM-86 | 20 | 36 |
| CTM-87 | 48 | 52 |
| CTM-88 | 60 | 65 |
| CTM-106 | 26 | >100 |
| CTM-107 | 21 | 47 |
| CTM-108 | 13 | >100 |
| CTM-109 | 29 | >100 |
| CTM-110 | 27 | >100 |
| CTM-131 | 70 | >100 |
| CTM-132 | 13 | 33 |
| CTM-165 | 26 | 50 |
| CTM-169 | 26 | 38 |
| CTM-182 | 60 | >100 |
| CTM-184 | 24 | 61 |
| CTM-191 | 18 | 25 |
| CTM-192 | 23 | 28 |
| CTM-193 | 26 | 32 |
| CTM-217 | 10 | 14 |
| CTM-218 | 15 | 22 |

The AC$_{200}$/μM for HSF is the concentration at which the tested compound doubled the HSF activity in this assay. The IC$_{50}$/μM for NF-κB is the concentration at which the tested compound halved the NF-κB activity in this assay. These results show the tested compounds to be powerful activators of HSF and that many are also powerful inhibitors of NF-κB.

Example 14

Alamar Blue Cytotoxicity Assay

HeLa cells were plated in 96-well microtiter plates in 100 μl culture medium ($4 \times 10^4$/well). After 20 hours, the cells were exposed to the test compounds at different dilutions and incubated for the next 8 h at 37° C. in a 5% $CO_2$ humidified atmosphere. After 6 h incubation, the Alamar Blue was added in an amount equal to 10% of the culture volume (10 μl). Two hours after the addition of the Alamar Blue, the fluorescence was measured using a Victor 1420 microplate reader.

The results for compounds CTM-68, CTM-78 and some further compounds in accordance with the invention that are described in Examples 8-10 were as follows:—

|  | LC$_{50}$/μM |
|---|---|
| CTM-68 | >800 |
| CTM-78 | >800 |
| CTM-80 | >800 |
| CTM-81 | 181 |

-continued

| | $LC_{50}/\mu M$ |
|---|---|
| CTM-82 | >800 |
| CTM-83 | >800 |
| CTM-84 | 556 |
| CTM-85 | 378 |
| CTM-86 | 96 |
| CTM-87 | 260 |
| CTM-88 | 477 |
| CTM-106 | 536 |
| CTM-107 | 169 |
| CTM-108 | >800 |
| CTM-109 | 267 |
| CTM-110 | >800 |
| CTM-115 | >800 |
| CTM-131 | >800 |
| CTM-132 | 220 |
| CTM-145 | >800 |
| CTM-165 | >800 |
| CTM-169 | >800 |

The $LC_{50}/\mu M$ is the concentration at which the tested compound killed half the cells in this assay. These results show that the tested compounds do not become significantly cytotoxic to HeLa cells until their concentration has very considerably exceeded that at which they were shown to activate HSF and, in many cases, inhibit the activity of NF-κB in Example 13.

Example 15

Neutral Red Assay

Cell viability was determined using the Neutral Red assay. 37RC cells were seeded at density of 6×10⁴ cells/well in 24-well plates and incubated for 24 h. Confluent 37RC monolayers were treated with the test compounds at different dilutions for 24 h at 37° C. After incubation, the medium was removed and the cells were incubated with RPMI medium containing 40 µg/ml Neutral Red dye (500 µl/well). After 2 h at 37° C., the monolayers were washed with phosphate-buffered saline (PBS) and then with a solution containing 1% $CaCl_2$ and 0.5% formaldehyde. After washing, a solution containing 1% acetic acid/50% ethanol was added to the monolayers (250 µl/well). After 10 min at room temperature, the absorbance was determined with a microplate reader (Victor 1420, Wallac) at 540 nm.

The $LC_{50}$ (the 50% lethal dose/concentration) values in this assay for compounds CTM-68 and CTM-78 and some further compounds in accordance with the invention that are described in Examples 8-10 are set out below:

| | $LC_{50}/\mu M$ |
|---|---|
| CTM-68 | 9.8 |
| CTM-78 | 18.6 |
| CTM-80 | 16 |
| CTM-81 | 17 |
| CTM-82 | 16 |
| CTM-83 | 27 |
| CTM-84 | 6.3 |
| CTM-85 | 10.6 |
| CTM-86 | 7 |
| CTM-87 | 38 |
| CTM-88 | 45 |
| CTM-106 | 28 |
| CTM-108 | 29 |
| CTM-109 | 33 |

-continued

| | $LC_{50}/\mu M$ |
|---|---|
| CTM-110 | 18 |
| CTM-115 | 228 |
| CTM-131 | 125 |
| CTM-132 | 2.6 |
| CTM-145 | 14 |
| CTM-165 | 21 |
| CTM-169 | 22 |
| CTM-182 | 54 |
| CTM-183 | 28 |
| CTM-184 | 25 |
| CTM-191 | 24 |
| CTM-192 | 22 |
| CTM-193 | 23 |

These results confirm that the anti-viral effect (see Example 12) of these compounds took place at a concentration well below that at which they were toxic to uninfected 37RC cells.

Example 16

Effect of Inventive Compounds on Infection with Influenza Virus

Human lung adenocarcinoma A549 cells are grown at 37° C. in RPMI-1640 medium, supplemented with 10% fetal calf serum (FCS, Gibco) and antibiotics. Influenza A virus A/WSN/33 (H1N1) (WSN virus) is grown in the allantoic cavity of 10-day-old embryonated eggs. Virus titers are determined by hemagglutinin titration, according to standard procedures (Pica F, Palamara A T, Rossi A, De Marco A, Amici C and Santoro M G: $\Delta^{12}$-Prostaglandin $J_2$ is a potent inhibitor of influenza A virus replication. *Antimicrob. Agents Chemother.*, 44: 200-204, 2000). Confluent A549 monolayers are infected with WSN virus (10 HAU/10⁵ cells) for 1 h at 37° C. After this time, viral inoculum is removed and cells are treated with different concentrations of inventive compound or ethanol-diluent. Viral yields are determined 24 and 48 h post infection (p.i.) and expressed as HAU/ml.

Example 17

MTT Assay

Cell viability is determined by the 3-(4,5-dimethylthiazol-2-yl)-2,5-diphenyltetrazolium bromide (MTT) assay. Uninfected A549 (7.5×10⁴ cells/well in 96 well plates) or 37RC cells (2.5×10⁴ cells/well in 96 well plates) are treated with different concentrations of inventive compound or ethanol diluent for 24 hours. After this time, 10 ml of a 0.5% MTT solution in PBS is added to the monolayers and the mixture is incubated for 2 h at 37° C. Reduced MTT (formazan) is extracted from cells by adding 100 µl of acidic isopropanol containing 10% Triton X-100, and formazan absorbance is measured in an ELISA microplate reader at two different wavelengths (540 and 690 nm).

Example 18

Assaying for Anti-Inflammatory Effect

Immune cells such as neutrophils and macrophages are activated in response to injury and infection. When activated they produce nitric oxide and superoxide radicals to kill foreign cells and cancer cells. They also produce a variety of cytokines and chemokines to cause further recruitment of immune cells in a cascade leading to the cardinal symptoms of inflammation; heat, redness, swelling, pain, and loss of function.

A key signalling step in the activation of the immune cells is the transcription factor nuclear factor κ B (NF-κB) (16). NF-κB regulates the transcription of a spectrum of pro-inflammatory genes such as IL-1, IL-2, TNF-α, ICAM-1, VCAM-1, and E-selectin as well as the inducible form of nitric oxide synthase (iNOS) and cyclo-oxygenase II.

Thus the activation of NF-κB occupies a critical position in the inflammatory cascade. A test compound can be tested for its effects on the induction of iNOS in a mouse macrophage model.

Mouse macrophages of the cell line RA W264.7 can be stimulated with gamma interferon and 0.1 U/ml of bacterial lipopolysaccharide (LPS) in 96-well plates (17). The induction of iNOS can be measured by determination of the levels of nitrite ($NO_2^-$) formed in the supernatant, using the Griess reagent.

It can be determined whether or not a test compound has an inhibitory effect on nitrite formation (preferably at submicromolar concentrations). The natural cyclopentenone prostaglandin PG-$J_2$ can be used for comparison. (IC50 values obtained for $PGJ_2$ and a test compound can be compared).

If the results of the experiment indicated that the induction of the pro-inflammatory iNOS genes by interferon gamma and LPS treatment is suppressed by a test compound, the most likely explanation is that the test compound is inhibiting the activation of the NF-κB pathway.

Example 19

Assaying to Determine Whether or not a Compound Lowers Blood Pressure

Most prostaglandins have strong effects on vascular smooth muscle, and win lower blood pressure in animals and humans. A compound can be tested for its effect on the blood pressure of the anaestheized rat. Prostaglandins $A_1$ and $E_1$ can be used for comparison.

Male Wistar rats were anaesthetized and test drugs can be infused intravenously. Blood pressure and heart rate can be recorded from the femoral artery.

Prostaglandins $A_1$ and $E_1$ cause dose-dependant falls in blood pressure in doses from 30 μg/kg/min. It can be determined whether or not a test compound affects blood pressure at various dosages. As a control, solvent alone can be used.

If a compound does not cause significant changes in blood pressure, it may be devoid of the generalised effects on smooth muscle characteristic of natural cyclopentenone prostaglandins.

Example 20

Calculated logP values

LogP values have been calculated for the following compounds

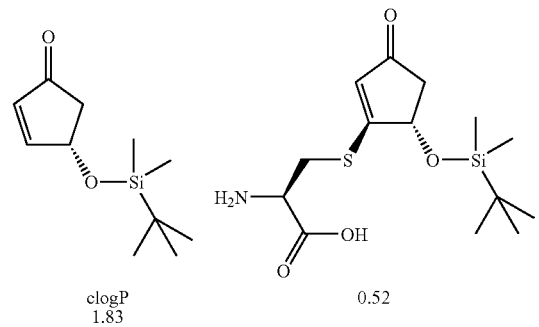

The first of these compounds is the equivalent cyclopent-2-en-1-one derivative to the second and third compounds, both of which are embodiments of the present invention. These results show the compounds in accordance with the invention can be significantly less lipophilic than their equivalent.

Figure 7:
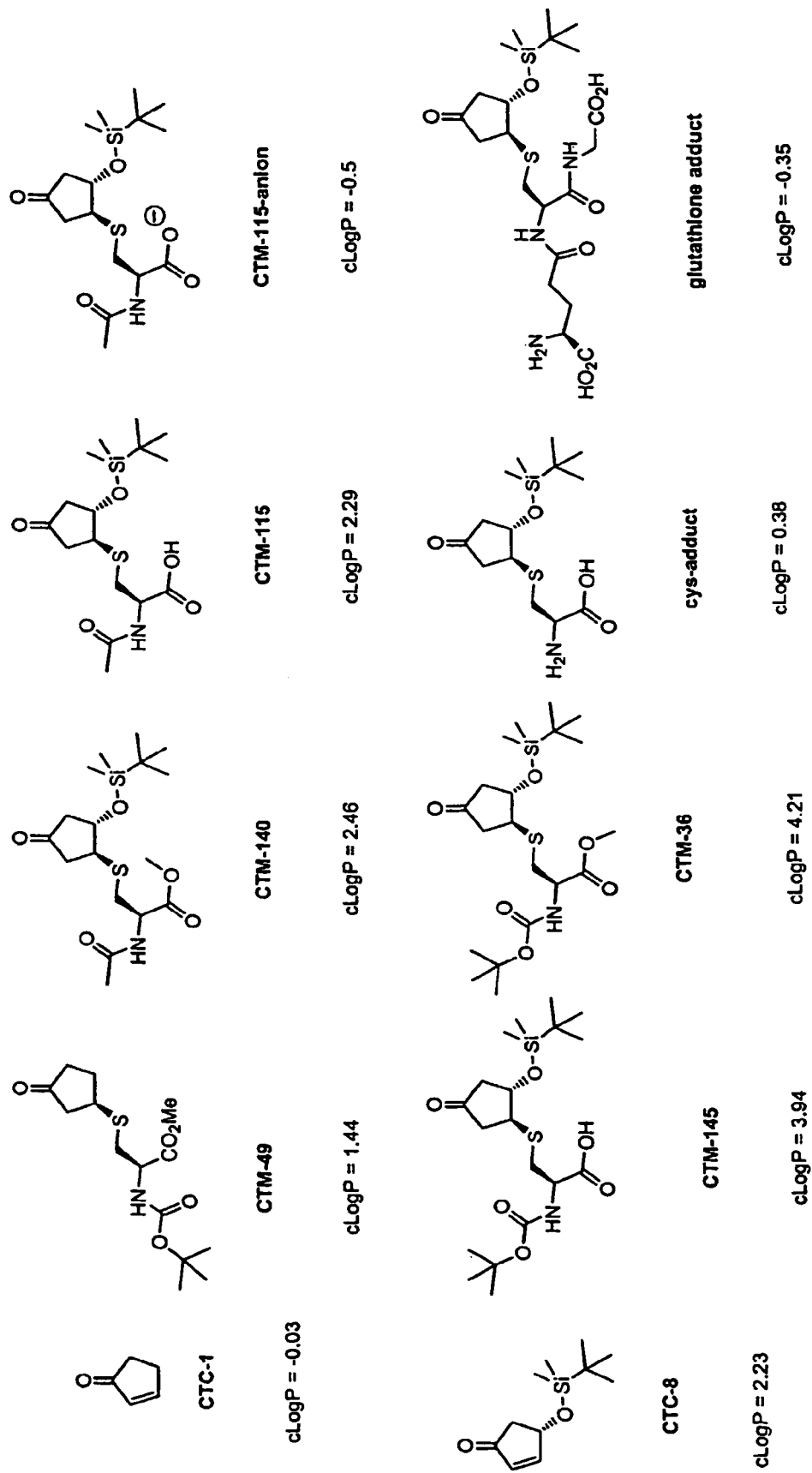

Some further cLogP values have been calculated using a different program (MacLogP) and are set out in FIG. 7. These results show the compounds in accordance with the invention can be significantly more or less lipophilic than the equivalent cyclopent-2-en-1-one derivative, depending upon the nature of the —SR group bound to their cyclopentanyl rings.

General Remarks

The foregoing description of the invention is merely illustrative thereof and it should therefore be appreciated that various variations and modifications can be made without departing from the spirit or scope of the invention as set forth in the accompanying claims.

Where preferred or optional features are described in connection with particular aspects of the present invention, they shall be deemed to apply mutatis mutandis to other aspects of the invention unless the context indicates otherwise.

All documents cited herein are hereby incorporated by reference, as are any citations referred to in said documents.

REFERENCES

1. Feige U, Morimoto R, Yahara I, Polia B S. *Stress-inducible Cellular Responses*. Birkhaüser Verlag, Basel Boston Berlin, 1996.
2. Marber M S, Walker J M, Latchman D S, 'Yellon D M. *J. Clin. Invest.* 93, 1087-1094, 1994.
3. Feinstein D L e al. *J. Biol. Chem.* 271, 17724-17732, 1996.
4. Amici C, Giorgi C, Rossi A, Santoro M G. *J. Virol* 68, 6890-6897, 1994.
5. Santoro M G, in *Stress-inducible Cellular Responses*. (Fiege U et al. eds, Birkhaüser Verlag, Basel Boston Berlin) pp. 337-357, 1996.
6. Santoro M G, Garaci 9, Amici C. *P.N.A.S. USA* 86, 8407-8411, 1989.
7. Amici C, Sistonen L, Santoro M G, Morimoto R I. *P.N.A.S. USA* 89, 6227-6231, 1992.
8. Santoro M G, Benedetto A. Carruba G, Garaci E, Jaffe B. *Science* 209, 1032-1034, 1980.
9. Santoro M G, *Trends Microbiol.* 5, 276-281, 1997.
10. Rozera C, Carattoli A, De Marco A, Amici C, Giorgi C, Santoro M G *J. Clin. Invest.* 97; 1795-1803, 1996.
11. Rossi A, Elia G, Santoro M G. *P.N.A.S. USA* 94,746-750, 1997.
12. Thanos D, Maniatis T. *Cell* 80, 529-532, 1995.
13. Rossi A, Elia G, Santoro M G. *J. Biol. Chem.* 271, 32192-32196, 1996.
14. Shield M J. *Pharmacol. Ther.* 65, 125-137, 1995.
15. Sinclair S B et al. *J. Clin. Invest.* 84, 1063-1067, 1989.
16. Baeuerle P A and Henkel T (1994). Function and Activation of NF-Kappa B in the Immune System. Annual Reviews of Immunology 12:141-179.
17. Colville-Nash P R et al. (1998). Inhibition of Inducible Nitric Oxide Synthase by Peroxisome Proliferator-Activated Receptor Agonists: Correlation with Induction of Heme Oxygenase 1. Journal of Immunology 161, 978-984.
18. K. J. Stone, R. D. Little, J O C, 1984, 49, 1849-1853.
19. A. Kawamoto, H. Kosugi, H. Uda, Chem. Lett., 1972, 807-810.
20. Moriguchi I, Hirono S, Liu Q, Nakagome Y, and Matsushita Y, (1992) Simple method of calculating octanol/water partition coefficient. Chem. Pharm. Bull. 40, 127-130.
21. Lipinski C, Lombardo F, Dominy B, Feeney P, (1997) Experimental and computational approaches to estimate solubility and permeability in drug discovery and development settings. Advanced Drug Delivery Reviews 23 (1997) 3-25.
22. Kondo, M.; Oya-Ito, T.; Kumagai, T.; Osawa, T.; Uchida, K. *J. Biolog. Chem.* 2001, 296, 12076-12083.
23. Silverman, R. B., In *The Organic Chemistry of Drug Design and Drug Action*; Academic Press; A Harcourt Science and Technology Company: San Diego, 1992, 336-338.
24. R. J. Flanagan, *Chemistry in Britain*, 2002, 28.
25. Meister, A., Anderson, M., E., *Ann. Rev. Biochem.* 1983, 52, 711-760.

The invention claimed is:

1. A pharmaceutical composition comprising a compound comprising a cyclopentanone group and having the formula:

(a) II or III

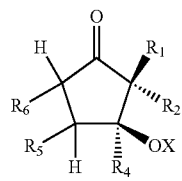

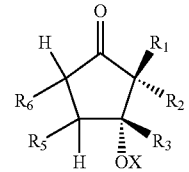

Wherein:—
$R_1$ and $R_2$ are, independently, hydrogen, halogen, substituted or unsubstituted alkyl, substituted or unsubstituted alkenyl, substituted or unsubstituted alkynyl, substituted or unsubstituted aminoalkyl, substituted or unsubstituted alkylthio, substituted or unsubstituted alkylsulfinyl, substituted or unsubstituted alkylsulfonyl, substituted or unsubstituted carbocyclic aryl, substituted or unsubstituted aralkyl, or substituted or unsubstituted heteroaromatic or heteroalicyclic;

$R_3$ and $R_4$ are hydrogen, $R_5$ is —SR, and R is a substituted or unsubstituted alkyl, alkenyl, alkynyl, aryl, aralkyl, aralkenyl, or aralkynyl group that, optionally, includes at least one heteroatom in its carbon skeleton;

$R_6$ is hydrogen or halogen, and X is:—

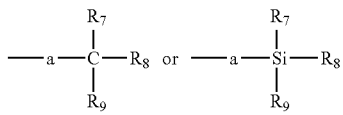

wherein $R_7$, $R_8$ and $R_9$ are, independently, hydrogen, halogen, substituted or unsubstituted alkyl, substituted or unsubstituted alkenyl, substituted or unsubstituted alkynyl, substituted or unsubstituted alkoxy, substituted or unsubstituted aminoalkyl, substituted or unsubstituted alkylthio, substituted or unsubstituted alkylsulfinyl, substituted or unsubstituted alkylsulfonyl, substituted or unsubstituted carbocyclic aryl, substituted or unsubstituted aralkyl, or substituted or unsubstituted heteroaromatic or heteroalicyclic, and "a" is absent or a hydrocarbyl linking group;

(b) VI:—

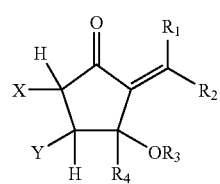

wherein:—
- $R_1$ is H, or a substituted or unsubstituted alkyl or alkenyl group containing 1 to 3 carbon atoms;
- $R_2$ is a substituted or unsubstituted alkyl, alkenyl, alkynyl, aryl, aralkyl aralkenyl, or aralkynyl group, optionally including at least one heteroatom in its carbon skeleton, and containing 1-12 carbon atoms;
- $R_3$ is a substituted or unsubstituted alkyl, alkenyl, alkynyl, aryl, aralkyl aralkenyl, or aralkynyl group, optionally including at least one heteroatom in its carbon skeleton, and containing 1-12 carbon atoms, or a silyl group;
- $R_4$ is hydrogen;
- X is hydrogen, halogen or an alkyl group containing 1-3 carbon atoms;
- Y is a group —SR; and
- R is a substituted or unsubstituted alkyl, alkenyl, alkynyl, aryl, aralkyl, aralkenyl, or aralkynyl group that, optionally, includes at least one heteroatom in its carbon skeleton;

(c) VII:—

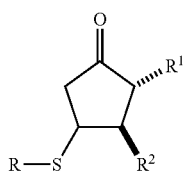

VII wherein $R^1$ is a saturated or unsaturated, branched or straight alkyl chain terminated with a COOX group and includes 4 to 15 carbon atoms, X is H or a $C_1$-$C_6$ alkyl group, $R^2$ is a straight chain $C_1$-$C_{20}$ saturated alkyl group, R is a substituted or unsubstituted alkyl, alkenyl, alkynyl, aryl, aralkyl, aralkenyl, or aralkynyl group that, optionally, includes at least one heteroatom in its carbon skeleton, and the ring carbon atoms are otherwise unsubstituted; or, (d) VIII:—

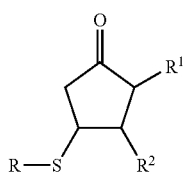

VIII wherein each of $R^1$ and $R^2$ is a saturated or unsaturated branched or straight chain alkyl group, both $R^1$ and $R^2$ together include between 4 and 12 carbon atoms, $R^1$ is unsubstituted, R is unsubstituted alkyl, alkenyl, alkynyl, aryl, aralkyl, aralkenyl, or aralkynyl group that, optionally, includes at least one heteroatom in its carbon skeleton, and the ring carbon atoms are otherwise unsubstituted,
and a pharmaceutically acceptable carrier.

2. A pharmaceutical composition as in claim 1, comprising a compound having a calculated or measured logP value that is at least 0.25, 0.5, 0.75, 1 or 1.25 higher or lower than the logP value for the equivalent cyclopent-2-en-1-one derivative in which a hydrogen atom replaces said —SR group, wherein the logP values for the compound and derivative are calculated or measured using the same technique.

3. A pharmaceutical composition as in claim 1, comprising a compound comprising a substituted or unsubstituted 3-(RS)-cyclopentan-1-one or 4-(RS)-cyclopentan-1-one.

4. A pharmaceutical composition as in claim 1 comprising a compound that is transformable into the equivalent cyclopent-2-en-1-one derivative, in which a hydrogen atom replaces said —SR group, by a reverse Michael reaction, or that is a pro-drug for said equivalent.

5. A pharmaceutical composition as in claim 1, comprising a compound comprising a plurality of —SR groups.

6. A pharmaceutical composition as in claim 5, comprising a compound comprising an additional —SR group bound to a substituent, itself bound to the cyclopentanone group.

7. A pharmaceutical composition as in claim 6 comprising a compound comprising an additional group —SR bound to the first carbon atom in a side chain carried by the ring carbon atom adjacent (α) to the carbonyl ring carbon atom.

8. A pharmaceutical composition as in claim 1, comprising a compound wherein R is an $R^X CH_2$-group and $R^X$ is hydrogen or a substituted or unsubstituted alkyl, alkenyl, alkynyl, aryl, aralkyl, aralkenyl, or aralkynyl group, that optionally includes at least one heteroatom in its carbon skeleton.

9. A pharmaceutical composition as in claim 1 or 8, comprising a compound wherein R or $R^X$ includes at least one hydrophilic group.

10. A pharmaceutical composition as in claim 9, comprising a compound wherein said hydrophilic group is or includes a hydroxyl, carbonyl, carboxyl, amino, amido, quaternary ammonium or thiolyl group.

11. A pharmaceutical composition as in claim 10, comprising a compound wherein R or $R^X$ provides the functionality of an amine, amide, peptide, ester, carboxylic acid, carboxylic acid salt, alcohol, aldehyde, ketone or thiol to said compound.

12. A pharmaceutical composition as in claim 1 or 8, comprising a compound wherein R or $R^X$ includes at least one lipophilic group and/or is lipophilic.

13. A pharmaceutical composition as in claim 12, comprising a compound wherein said lipophilic group is a substituted or unsubstituted alkyl, alkenyl, alkynyl, aryl, aralkyl, aralkenyl, or aralkynyl group that, optionally, includes at least one heteroatom in its carbon skeleton.

14. A pharmaceutical composition as in claim 13, comprising a compound wherein said lipophilic group is a substituted or unsubstituted phenyl or napthyl group, or an N-tert-butoxycarbonyl S-cysteinyl ester.

15. A pharmaceutical composition as in claim 1, comprising a compound wherein the group —SR is an S-cysteinyl or a substituted S-cysteinyl group.

16. A pharmaceutical composition as in claim 15, comprising a compound wherein the substituted S-cysteinyl group is a di- or tri-peptide group that includes an S-cysteinyl moiety.

17. A pharmaceutical composition as in claim 16, comprising a compound wherein the substituted S-cysteinyl group is an S-glutathionyl, an S-cysteinyl N-tert-butoxycarbonyl, an S-cysteinyl ester, an S-glutathionyl ester, or an S-cysteinyl N-tert-butoxycarbonyl group.

18. A pharmaceutical composition as in claim 1 comprising a compound having the formula (a) or (b):—

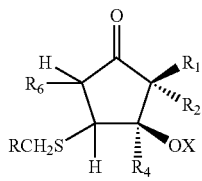

(a)

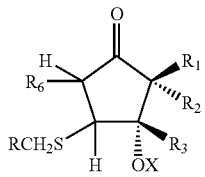

(b)

wherein: R is as defined in claim 1.

19. A pharmaceutical composition as in claim 1, said comprising a compound having the formula II or III, wherein $R_1$ and $R_2$ are hydrogen, or the formula IV, wherein X is hydrogen.

\* \* \* \* \*